United States Patent
Liang et al.

(10) Patent No.: US 11,188,738 B2
(45) Date of Patent: Nov. 30, 2021

(54) SYSTEM AND METHOD ASSOCIATED WITH PROGRESSIVE SPATIAL ANALYSIS OF PRODIGIOUS 3D DATA INCLUDING COMPLEX STRUCTURES

(71) Applicant: The Research Foundation for the State University of New York, Albany, NY (US)

(72) Inventors: Yanhui Liang, East Setauket, NY (US); Fusheng Wang, Lake Grove, NY (US); Hoang Vo, Centereach, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 144 days.

(21) Appl. No.: 16/481,744

(22) PCT Filed: Feb. 7, 2018

(86) PCT No.: PCT/US2018/017208
§ 371 (c)(1),
(2) Date: Jul. 29, 2019

(87) PCT Pub. No.: WO2018/148267
PCT Pub. Date: Aug. 16, 2018

(65) Prior Publication Data
US 2020/0005015 A1    Jan. 2, 2020

Related U.S. Application Data

(60) Provisional application No. 62/456,464, filed on Feb. 8, 2017.

(51) Int. Cl.
G06K 9/00       (2006.01)
G16H 30/20     (2018.01)
G06K 9/62       (2006.01)

(52) U.S. Cl.
CPC ....... *G06K 9/0014* (2013.01); *G06K 9/00201* (2013.01); *G06K 9/6272* (2013.01); *G16H 30/20* (2018.01)

(58) Field of Classification Search
None
See application file for complete search history.

(56) References Cited

U.S. PATENT DOCUMENTS

| | | |
|---|---|---|
| 2006/0190285 A1* | 8/2006 | Harris ............... G06Q 50/16 705/1.1 |
| 2009/0006395 A1* | 1/2009 | Ballester ............. G16B 35/00 |
| 2017/0018116 A1* | 1/2017 | Sun ...................... G06T 7/12 |

FOREIGN PATENT DOCUMENTS

WO    2018148267 A1    8/2018

OTHER PUBLICATIONS

3D Modelling. https://en.wikipedia.org/wiki/3D_modeling.
(Continued)

*Primary Examiner* — Fayyaz Alam
(74) *Attorney, Agent, or Firm* — Hoffmann & Baron, LLP

(57) ABSTRACT

A system associated with progressive spatial analysis of prodigious 3D data including complex structures is disclosed. The system receives minimum boundary information related to a first data object and a second data object, which are proximate neighbors. The system determines whether boundary data associated with a first data object is within an area delineated by minimum boundary information of first data objects. A first geometric structure associated with the first data object is generated based on respective decompressed data. A structural skeleton is determined using the first geometric structure to identify respective skeleton vertices. A geometric representation is generated based on the skeleton vertices associated with the first geometric structure. The system determines whether boundary data associated with the second data object is within the area delineated (Continued)

Spatial queries on complex 3D data.

by the minimum boundary information of the first data object. A centroid point of the second data object that intersects the geometric representation associated with the first object is identified. A location of the centroid point of the second data object with respect to the first data object is determined in order to identify a minimum distance between the first data object and the second data object.
A corresponding method and computer-readable device are also disclosed.

30 Claims, 50 Drawing Sheets

(56) References Cited

OTHER PUBLICATIONS

The Computational Geometry Algorithms Library (CGAL). http://www.cgal.org/.
ESRI 3D GIS. http://www.esri.com/products/arcgis-capabilities/3d-gis.
OFF Format. https://en.wikipedia.org/wiki/OFF_(le_format).
OpenTopography. http://www.opentopography.org/.
Spatial Index Library, http://libspatialindex.github.com.
Mchenry, Kenton, et al., "An Overview of 3D Data Content, File Formats and Viewers," National Center for Supercomputing Applications 1205 (2008): 22.
Aji, Ablimit, et al. "Hadoop-GIS: A High Performance Spatial Data Warehousing System Over MapReduce," Proceedings of the VLDB Endowment International Conference on Very Large Data Bases. vol. 6. No. 11. NIH Public Access, 2013.
Arge, Lars, et al., "A Unified Approach for Indexed and Non-Indexed Spatial Joins," In International Conference on Extending Database Technology, pp. 413-429. Springer, Berlin, Heidelberg, 2000.
Bercken, J., et al., "An Evaluation of Generic Bulk Loading Techniques," pp. 461-470, VLDB, 2001.
Brinkhoff, Thomas, et al., "Parallel Processing of Spatial Joins Using R-Trees," In Proceedings of the Twelfth International Conference on Data Engineering, pp. 258-265. IEEE, 1996.
Davidson, Aaron, et al., "Optimizing Shuffle Performance in Spark," University of California, Berkeley-Department of Electrical Engineering and Computer Sciences, Tech. Rep (2013).
Hoppe, Hugues, "Progressive Meshes," In Proceedings of the 23rd Annual Conference on Computer Graphics and Interactive Techniques, pp. 99-108, 1996.
Liang, Yanhui, et al., "Scalable 3D Spatial Queries for Analytical Pathology Imaging with MapReduce," In Proceedings of the 24th ACM SIGSPATIAL International Conference on Advances in Geographic Information Systems, pp. 1-4. 2016.
Maglo, Adrien, et al., "Progressive Compression of Manifold Polygon Meshes," Computers & Graphics 36, No. 5 pp. 349-359, 2012.
Peng, Jingliang, et al., "Technologies for 3D Mesh Compression: A Survey," Journal of Visual Communication and Image Representation 16, No. 6, pp. 688-733, 2005.
Tang, Mingjie, et al., "LocationSpark: A Distributed In-Memory Data Management System for Big Spatial Data," Proceedings of the VLDB Endowment 9, No. 13, pp. 1565-1568, 2016.
Vo, Hoang, et al., "SATO: A Spatial Data Partitioning Framework for Scalable Query Processing," In Proceedings of the 22nd ACM SIGSPATIAL International Conference on Advances in Geographic Information Systems, pp. 545-548. 2014.

Wang, Fusheng, et al., "A High-Performance Spatial Database Based Approach for Pathology Imaging Algorithm Evaluation," Journal of Pathology Informatics 4 (2013).
Wang, Kaibo, et al., "Accelerating Pathology Image Data Cross-Comparison on CPU-GPU Hybrid Systems," In Proceedings of the VLDB Endowment International Conference on Very Large Data Bases, vol. 5, No. 11, pp. 1543-1554. NIH Public Access, 2012.
Xie, Dong, et al., "Simba: Efficient In-Memory Spatial Analytics," In Proceedings of the 2016 International Conference an Management of Data, pp. 1071-1085. 2016.
You, Simin, et al., "Large-Scale Spatial Join Query Processing in Cloud," In 2015 31st IEEE International Conference an Data Engineering Workshops, pp. 34-41. IEEE, 2015.
Beckmann, Norbert, et al., "The R*-Tree: an Efficient and Robust Access Method for Points and Rectangles," In Proceedings of the 1990 ACM SIGMOD International Conference on Management of Data, pp. 322-331,1990.
Charles, Nikki, A., et al., "The Brain Tumor Microenvironment", Glia 60, No. 3, pp. 502-514, 2012.
Zhou,Xiaofang, et al., "Data partitioning for parallel spatial join processing", Geoinformatica 2, pp. 175-204 (1998).
Wang, Fusheng, et al., "High Performance Spatial Queries for Spatial Big Data: From Medical Imaging to GIS," Sigspatial Special 6, No. 3, pp. 11-18, 2015.
Toofanny, Rudesh D., et al., "Implementation of 3D Spatial Indexing and Compression in a Large-Scale Molecular Dynamics Simulation Database for Rapid Atomic Contact Detection," BMC Bioinformatics 12, No. 1: 334, 2011.
Takahashi, Tohru, Pathology of Organ Structure by Analysis and Interpretation of Images (second edition), SciPress, Tokyo , 2011.
Aji et al., "Hadoop GIS: A High Performance Spatial Data Warehousing System over MapReduce", The 39th International Conference on Very Large Data Bases, Aug. 26- 30, 2013, Riva del Garda, Trento, Italy, Proceedings of the VLDB Endowment, vol. 6, No. 11, pp. 1009-1020.
Xie et al., "Simba: Efficient In-Memory Spatial Analytics", SIGMOD'16, Jun. 26-Jul. 1, 2016, San Francisco, CA, USA.
Yu et al., "GeoSpark: A Cluster Computing Framework for Processing Large-Scale Spatial Data", SIGSPATIAL'15 Nov. 3-6, 2015, Bellevue, WA, USA.
Eldawy et al., "Spatial Hadoop: A MapReduce Framework for Spatial Data", Computer Science and Engineering, University of Minnesota, Minneapolis, MN, USA, 2015 IEEE International Conference on Data Engineering, Seoul, 2015 p. 1352-1363.
Liang et al., "Liver Whole Slide Image Analysis for 3D Vessel Reconstruction", Proc IEEE Int Symp Biomed Imaging, Apr. 2015; 2015 pp. 182-185.
Liang et al., "A 3D Primary Vessel Reconstruction Framework with Serial Microscopy Images", Navab, N, Hornegger, J, Wells, WM and Frangi, AF, (eds.) MICCAI 2015 Part III. Lecture Notes in Computer Science. 18th International Conference on Medical Image Computing and Computer-Assisted Interventions (MICCAI), Oct. 5-9, 2015, Munich, Germany. Springer International, pp. 251-259.
"iSPEED: an Efficient In-Memory Based Spatial Query System for Large-Scale 3D Data with Complex Structures", SIGSPATIAL'17, Nov. 7-10, 2017, Los Angeles Area, CA, USA.
Wang, Fusheng et al. "Hadoop-GIS: A high performance spatial query system for analytical medical imaging with MapReduce." {online} Center for Comprehensive Informatics, Technical Report, published Aug. 2011. {retrieved Apr. 9, 2018 (Apr. 9, 2018)}.
Written Opinion, International Search Report dated Apr. 26, 2018 for International Application No. PCT/US18/17208.

\* cited by examiner

Spatial queries on complex 3D data.

An example of 3D spatial proximity estimation of artery (red) and vein (blue).

The spatial distribution of $L$ in normal and abnormal livers.

Architecture overview

| Algorithm : Typical workflow of Spatial Query System |
|---|
| 1  A. Raw data staging in distributed file system; |
| 2  B. Pre-processing for compression and partitioning; |
| 3  C. In-memory storage of compressed data and indexes; |
| 4  D. for *cuboid in input_collection* do |
| 5      Task filtering with partitioned cuboid index; |
| 6      On-demand indexing for objects within cuboid; |
| 7      MBB based spatial query processing(filtering); |
| 8      On-demand data decompression; |
| 9      Geometry spatial query processing(refinement); |
| 10 E. Boundary objects handling (as needed); |
| 11 F. Post-query processing; |

FIG. 5

Hierarchical view of multi-level indexing

Decimation of an intermediate level of detail of the 3D blood vessel model. Top: the $L^i$ level of detail. Bottom: the $L^{i-1}$ level of detail with inserted edges depicted in blue and faces with a removed vertex in green.

The compressed file structure with a compressed nucleus illustrating different LODs.

Simplification of spatial objects with complex structures.

Structural Index. (a) Vessel skeleton. The dots are skeleton vertices. (b) A vessel structure. (c) Illustration of AABB tree on a subset of vessel facets. Tree is constructed via a bottom-up approach.

Illustration of boundary objects. The green nucleus $O$ is a boundary object, and it is duplicated to cuboids $C_1$ and $C_2$ as $O_1$ and $O_2$.

Illustration of buffered boundary objects. The light shaded area is the added buffer for the vessel $V$ in cuboid $C_1$. $V$ is a boundary object with the buffer, and duplicated to cuboids $C_1$ and $C_2$ as $V_1$ and $V_2$.

A General Framework of 3D Spatial Data Processing in MapReduce

I1. Raw data staging

I2. Data compression (parallelized) → in-memory storage

I3. Spatial partitioning and indexing → in-memory storage

A. Block based filtering with global indexes

B. For each *cuboid* in *input_collection* system performs (in parallel)
    a. Query task grouping based on cuboid indexes
    b. On-demand indexing for objects in the cuboid
    c. Cuboid based spatial query processing C. Boundary-crossing object handling D. Storage of query results

FIG. 14A

Pre-processing of data for 3D spatial queries.

Spatial join workflow

Algorithm 3: Spatial join query algorithm

Input: *MBBs_1*: MBBs of dataset1 in cuboid C,
*MBBs_2*: MBBs of dataset2 in cuboid C 1   *MBB_array* = init_array(*MBBs_1*);
2   $R^*$-*tree_index* = construct_$R^*$-tree(*MBBs_2*);
3   for *MBB_i* ∈ *MBB_array* do
4       *compressed_geom1* = load_from_memory(*object_i_ID, memory_seg_ID*);
5       *geom1* = decompress_3D_geometry(*compressed_geom1, level_LOD*);
6       if *mbb_intersects(MBB_i, $R^*$-tree_index)* then
           /* obtain 3D geometry       */
7            *compressed_geom2* = load_from_memory(*obj_i_ID, memroy_seg_ID*);
8            *geom2* = decompress_3D_geometry(*compressed_geom2, level_LOD*);
9            if *geom_intersects(geom_1, geom_2)* then
10               report_intersection(*geom_1, geom_2*);
11               obtain_measurement(*geom_1, geom_2*);
12            end
13       end
14 end

FIG. 15C

Algorithm 4: Spatial nearest neighbor query algorithm

Input: *MBBs_v*: MBBs of blood vessels in cuboid C,
*MBBs_n*: MBBs of nuclei in cuboid C 1 *MBB_arrayV* = init_array(*MBBs_v*);
2 *skeleton_vertices* = init_array();
3 for *MBB_Vi* $\in$ *MBB_arrayV* do
4   *compressed_geomV* = load_from_memory(*vessel_i_ID, memory_seg_ID*);
5   *geomV* = decompress_3D_geometry(*compressed_geomV, level_LOD*);
6   (*skeleton_vertices_i* = extract_skeleton(*geomV*);
7   *skeleton_vertex$_s$et*.push((*skeleton_vertices_i, vessel_id_i*));
8 end
9 *voronoi_3d* = build_voronoi_diagram(*skeleton_vertex_set*);
10 *MBB_arrayN* = init_array(*MBBs_n*);
11 for *MBB_Ni* $\in$ *MBB_arrayN* do
12   *point_Ni* = extract_centroid(*MBB_Ni*);
13   *skeleton_vertex, vessel_id* = find_voronoi_site(*point_Ni, voronoi_3d*);
14   report_nearest_neighbor(*vessel_id*);
15   compute_distance(*point_Ni, vessel_id*);
16 end

FIG. 16B

Algorithm 5: Spatial proximity estimation algorithm

Input: *MBBs_v*: MBBs of vessels in cuboid C,
*MBBs_n*: MBBs of nuclei in cuboid C 1 *MBB_array_v* = init_array(*MBBs_v*);
2 *AABBs_set* = init_set();
3 for *MBB_v_i* ∈ *MBB_array_v*1 do
4     *compressed_geom_v* = load_from_memory(*v_i_ID, memory_seg_ID*);
5     *geom_v* = decompress_3D_geometry(*compressed_geom_v*, *lower_level_LOD*);
6     *AABBs_v* = extract_AABB(*geom_v*);
7     *AABBs_set*.insert((*AABBs_v, v_i_ID*));
8 end
9 $R^*$-*tree_index_v*1 = construct_$R^*$-tree(*AABBs_set*);
10 *MBB_array_n* = init_array(*MBBs_n*);
11 *dists* = init_array(*MBBs_n*);
12 for *MBB_n_i* ∈ *MBB_array_n* do
13     *point_i* = extract_centroid(*MBB_n_i*);
14     *nn_v* = find_nearest_neighbor($R^*$-*tree_index_v, MBB_n_i*);
15     *compressed_geom*1 = load_from_memory(*v_i_ID, memory_seg_ID*);
16     *geom* = decompress_3D_geometry(*compressed_geom, high_level_LOD*);
17     *AABB-tree_index_v* = build_AABB-tree(*geom*);
18     *dist* = compute_AABB-tree_distance(*point_n_i, geom*);
19     *dists*.push(dist);
20 end

FIG. 17C

Example 3D Spatial Join

Evaluation of level of detail in data compression

| 3D Object | dataset | Hausdorff distance |
|---|---|---|
| 3D Vessel | 1X | 0.079 ± 0.91% |
|  | 3X | 0.085 ± 0.88% |
|  | 5X | 0.091 ± 0.83% |
| 3D Cell | 1X | 0.152 ± 0.52% |
|  | 3X | 0.131 ± 0.61% |
|  | 5X | 0.157 ± 0.57% |

Evaluation results with Hausdorff distance metric

| Dataset | 1X | 3X | 5X |
|---|---|---|---|
| Number of slides | 56 | 168 | 280 |
| Number of 3D nuclei | $1.4 \times 10^6$ | $4.1 \times 10^6$ | $6.8 \times 10^6$ |
| Number of 3D vessels | 5,200 | 14,100 | 22,320 |
| Dataset size | 90GB | 272GB | 460GB |

3D dataset for performance study

Spatial join with 460GB data

Memory usage of spatial join query execution

CPU utilization of spatial join query execution

Spatial join: 3D Query System vs. Hadoop-GIS 3D

Nearest neighbor query: 3D Query System vs. Hadoop-GIS 3D

Spatial proximity estimation: 3D Query System vs. Hadoop-GIS 3D

Execution time on different LODs

Error rate on different LODs

Scalability of 3D Query System on spatial join

Scalability of 3D Query System on nearest neighbor query

Scalability of 3D Query System on spatial proximity estimation

SYSTEM AND METHOD ASSOCIATED WITH PROGRESSIVE SPATIAL ANALYSIS OF PRODIGIOUS 3D DATA INCLUDING COMPLEX STRUCTURES

CROSS-REFERENCE TO RELATED APPLICATION(S)

This application is the U.S. National Phase of International Patent Application No. PCT/US18/17208, filed on Feb. 7, 2018, which claims the benefit of U.S. Provisional Application No. 62/456,464, filed on Feb. 8, 2017, the specifications of which are incorporated by reference herein in their entirety for all purposes.

STATEMENT OF GOVERNMENT RIGHTS

This invention was made with government support under grant numbers 1661434 and 1541063 awarded by the National Science Foundation. The government has certain rights in the invention.

FIELD OF THE DISCLOSURE

The present disclosure relates to a system and method associated with progressive spatial analysis of prodigious 3D data including complex structures. Even more particularly, the present invention relates to a system and method for implementation of novel 3D spatial queries including user definable compression levels, resulting in greater accuracy as applicable to digital pathology and diagnostic related analysis of complex biological structures, such as vessels and cell nuclei.

BACKGROUND

Three-dimensional (3D) spatial data is being produced at an unprecedented rate and scale over the last decade, due to the proliferation of cost effective and ubiquitous positioning technologies. Analyzing a large amount of 3D spatial data to derive values and guide decision making has become essential to business success and scientific discoveries. In the mining and exploration industry, 3D models of large scale spatial geosciences data are utilized to provide accurate and reliable geographic information for mineral exploration and environmental assessments. Investors and analysts rely on such data to challenge assumptions, confirm theories and make informed, data-led decisions regarding the potential success of a project.

3D spatial data has been used in numerous industrial applications, such as CAD, urban planning, 3D mapping, 3D navigation, terrain modeling, mineral exploration and environmental assessments. Managing and analyzing large amounts of 3D spatial data to derive values and guide decision-making, have become essential to achieve business success and scientific discoveries. The rapid growth of 3D spatial data is driven not only by industrial applications, but also scientific applications that are increasingly data intensive, computationally complex and processing intensive.

The rapid development of data acquisition technologies, such as 3D remote sensing instruments and high-resolution tissue slide scanners, has enabled more efficient approaches to capture extremely large spatial data to support and further advance various areas of scientific research. In the biomedical domain, 3D digital pathology imaging has proliferated in the past decade. Compared to traditional two-dimensional (2D) imaging, examination of 3D high resolution images of tissue specimens enables novel, more effective and accurate methods of screening for disease, classifying disease states, understanding disease progression and evaluating the efficacy of therapeutic strategies. 3D pathology image analysis offers a means of carrying out quantitative and reproducible measurements of micro-anatomical features with high resolution pathology images or large whole slide image datasets. Using a set of serial pathology images, 3D micro-anatomic objects such as blood vessels and nuclei are reconstructed through 3D image segmentation and modeling, represented with 3D mesh models, and structural features can also be extracted from these objects.

In the past decade, digital pathology has emerged as a powerful approach to assist disease diagnosis and advance biomedical research, which has been recently approved by FDA. As 2D projected appearances of 3D pathologic objects highly depend on the locations and angles of the cutting planes randomly selected during tissue slide preparation process, 3D spatial relationships could be misrepresented after such projection. Recently, 3D digital pathology imaging is made possible through slicing tissue block into serial sections. The information-lossless 3-D tissue space represented by microscopy imaging volumes holds significant potential to enhance studies of both normal and disease processes.

Quantitative 3D pathology imaging requires that 3D micro-anatomic objects such as blood vessels, cells and nuclei, be derived, together with their associated features using 3-D registration, segmentation and reconstruction. The next step is generally to explore spatial relationships among a massive number of such 3D objects, to discover spatial patterns, and their correlations with disease progression. For example, in brain tumor studies, it is desired to measure the distances from cells to their nearest neighboring tumor vessels. As another example, it is desired to implement a containment query to identify only cells of interest contained in a blood vessel or within certain distance(s) from the vessel.

The explosion of 3D data presents a number of challenges in the 3D pathology imaging and/or biomedical field(s). Digital scanners can produce microscopy images at an extremely high resolution. A typical 2D microscopy image may contain 100,000×100,000 pixels, with a million micro-anatomic objects. A typical 3D tissue volume may generate hundreds of slices, and contain tens of millions of 3D biological objects with each object represented with hundreds to thousands of mesh facets. A typical study may involve hundreds of patients and contain hundreds of tissue volumes. Such unprecedented scale of 3D objects in analytical pathology studies, poses significant challenges on data processing, leading to tremendous I/O, communication, and computational related costs, as well as related latencies in speed and other inefficiencies.

3D biological objects may include complex structures, such as bifurcated vessels. While minimal bounding boxes (MBBs) have been successfully used in traditional spatial indexing, MBBs are not effective to represent such complex 3D objects for distance-based spatial queries, such as nearest neighbor search. Therefore, there is a requirement for different indexing approaches for 3D biological objects. In practice, 3D objects are commonly represented with multiple resolutions with different Level of Detail (LOD). For example, Google Earth uses LOD mechanisms to allow efficient 3D region renderings for map visualization(s). In digital pathology, it is desired to quickly visualize rough 3D shapes of blood vessels to explore spatial relationships, and exploring 3D structure details for fine calculation of vessel features. LOD in higher resolution provides more accurate results for spatial computations, but could significantly increase data volume and computation cost. Thus, there is a desire for a 3D spatial querying system that balances accuracy and computational costs.

Furthermore, 3D spatial queries involve computationally intensive geometric operations for quantitative measurements and identifications of topology relationships. When analyzing spatial joins of large datasets, while minimal bounding boxes (MBBs) can be used to quickly filter 3D object pairs that do not intersect, spatial refinement could be a complex, intensive and time consuming operation to determine if intersection exists for polyhedron pairs of 3D objects. Moreover, queries that require quantitative spatial measurements such as computation of intersected volumes of objects with LODs at high resolution, geometric computation could impact the query cost. Thus, it is desirable to implement an efficient 3D spatial querying system with optimized I/O, while simultaneously providing high scalability by implementing large scale distributed computing resources.

The unique challenges presented by large scale complex 3D spatial queries demand a highly efficient and scalable 3D querying system that can mitigate potential high I/O and tangential communication costs from exchange of extreme data sizes, exploit indexing techniques suitable for complex objects, ease computational costs, and provide high scalability. Recently, several systems have been proposed to support large scale 2D spatial queries with distributed computing, but such systems lack critical components for 3D support. For example, known commercial systems such as Oracle Spatial only supports simple 3D objects, such as cuboid, frustum or their variations and are not known to support complex structured 3D objects.

Therefore, it is desirable to implement a system and method associated with an effective and scalable in-memory based spatial query system (and/or engine) for large-scale 3D data including complex structures. It is desirable for a system and method that achieve low latency, storing data in memory using effective progressive compression for each 3D object with successive levels of detail. It is further desirable to implement a system and method that minimizes search space and computational costs, pre-generates global spatial indexes in memory and employs on-demand indexing at run-time. In order to achieve such goals, such system and method exploits structural indexing for complex structured objects in distance based queries. It further provides a 3D spatial query engine that can be invoked on-demand to run many instances in parallel that can be implemented with, for example, with MapReduce, among other systems. It is further desirable to implement a system and method that builds in-memory indexes and decompresses data on-demand, with minimal memory footprint. It is further desirable to implement a system and method that is associated with 3D spatial joins and 3D spatial proximity estimation that significantly improves the performance, efficiency, and time-latencies over traditional non-memory based spatial query systems.

Therefore, it is desirable to implement an efficient and scalable in-memory based spatial query processing system for large scale 3D data that achieves low latency by storing data in memory in a highly compressed form using an effective progressive compression approach that compresses each 3D object individually with successive levels of detail. It is further desirable to implement an efficient and scalable in-memory based spatial query processing system that minimizes search space and computational cost, provides global spatial indexing in memory through partitioning at subspace level and partitioned cuboid level. It is further desirable to implement an efficient and scalable in-memory based spatial query processing system that provides an in-memory 3D spatial query engine, which can be invoked on-demand for running multiple instances in parallel. It is further desirable to implement an efficient and scalable in-memory based spatial query processing system that at run time, can dynamically decompress only required 3D objects at the specified level of detail, and create necessary spatial indexes in-memory to accelerate query processing, such as on-demand object-level indexing and structural indexing on complex structured objects. It is further desirable to implement an efficient and scalable in-memory based spatial query processing system that supports multiple spatial queries, including but not limited to spatial joins, nearest neighbor, and spatial proximity estimation, and that can be easily extended to other spatial queries.

IT is further desirable to implement an efficient and scalable in-memory based spatial query processing system that has the ability to process and thereby, explore massive 3D spatial biological objects. The 3D data compression approach makes it possible to significantly reduce data size to have them in memory at very low memory footprint with effective compression and on-demand decompression, which leads to much reduced I/O and communication cost for query processing.

IT is further desirable to achieve a system and method that models 3D objects with multiple levels of detail for spatial queries, thereby providing options for users to decide and tailor their goals for faster queries or higher accuracy to meet application specific requirements.

IT is further desirable to achieve a system and method that provides multi-level in-memory spatial indexing to reduce search space and accelerate queries. This can be achieved by implementation of unique structural indexing for searching with complex structured objects, which significantly improves query performance as compared to traditional MBB based indexing.

IT is further desirable to achieve a system and method that performs on-demand in-memory based 3D spatial queries using an engine that fully takes advantage of multi-level indexing and data decompression for processing multiple types of spatial queries, which can be implemented with a particular computing paradigm.

IT is further desirable to implement a system and method that achieves significant benefits on efficiency and scalability of spatial queries over traditional non-memory based spatial query systems.

IT is further desirable to implement a system and method that effectively performs spatial queries by additionally permitting the user system to specify a level of detail (LOD) resolution that is customizable based on performance results, in order to achieve optimal query results during compression and spatial query processing (for example, greater accuracy, speedier execution time and lower memory usage) when performing any of the disclosed spatial queries and processes.

SUMMARY

In accordance with an embodiment or aspect, the present technology is directed to a system and method associated with progressive spatial analysis of prodigious 3D data including complex structures. The system comprises a 3D spatial query engine that includes a computing device.

In accordance with an embodiment or aspect, disclosed is the system and method that includes the computing device perform operations including receiving minimum boundary information related to a first data object and receiving minimum boundary information related to a second data object, the first data object and the second data object being proximate neighbors. The system and method further includes determining whether boundary data associated with the first data object is within an area delineated by minimum boundary information of first data objects and generating a first geometric structure associated with the first data object based on respective decompressed data associated with the first data object. The system and method further includes determining a structural skeleton using the first geometric structure associated with the first data object in order to identify its respective skeleton vertices; and generating a geometric representation based on the skeleton vertices associated the first geometric structure. The system and method further includes determining whether boundary data associated with the second data object is within the area delineated by minimum boundary information of the first data object; and identifying whether a centroid point of the second data object intersects the geometric representation associated with the first object. The system and method further includes determining a location of the centroid point of the second data object with respect to the first data object in order to identify a minimum distance between the first data object and the second data object.

In yet a further disclosed embodiment, the system and method further comprises iteratively receiving and processing minimum boundary information related to multiple first data objects and multiple second data objects. The system and method yet further includes that the first data object is a blood vessel and the second data object is one of a cell and a nucleus. The system and method further includes that the first data object is a first biological structure and the second data object is a second biological structure. The system and method yet further includes that the progressive spatial analysis comprises a determination of a nearest distance between at least one nucleus and a nearest blood vessel. In yet another embodiment, the system and method is disclosed, in which generating a first geometric structure associated with the first data object based on its decompressed data further comprises compressing the first data object according to a specified level of detail (LOD). The system and method further including that the specified level of detail (LOD) being varied to refine determination of minimum distance, based on an evaluation of compression of the first data object as associated with the progressive spatial analysis thereof.

In yet a further disclosed embodiment, disclosed is a system and method associated with progressive spatial analysis of prodigious 3D data including complex structures. The system and method comprises a 3D spatial query engine including a computing device that performs operations including receiving minimum boundary information related to first data objects, receiving minimum boundary information related to second data objects; and initializing an array with the minimum boundary information related to the first data objects. The disclosed system and method further includes determining whether minimum boundary information associated with one of the first data objects is related to an area delineated by the minimum boundary information in the array. The disclosed system and method further includes determining whether a first area delineated by the minimum boundary information associated with the one of the first data objects intersects an area delineated by a second area delineated by the minimum boundary information associated with one of the second data objects. The disclosed system and method further includes generating a first geometric structure associated with the one of the first data objects based on respective decompressed data associated with the one of the first data objects; and generating a second geometric structure object associated with the one of the second data objects based on respective decompressed data associated with the one of the second data objects. The disclosed system and method further includes determining whether a first geometric region defined by the first geometric structure intersects a second geometric region defined by the second geometric structure; and determining a spatial measurement of an intersecting region defined by an intersection of the first geometric region with the second geometric region. The disclosed system and method further includes identifying a first intersecting object and a second intersecting object associated with the intersecting region and respective volume information associated with the intersecting region.

In yet a further disclosed embodiment, the progressive spatial analysis of the disclosed system and method further comprises determining a minimum distance between the one of the first data objects and a nearest second data object based on a tree-based analysis of their respective minimum bounding information. The disclosed system and method may further comprise determining nearest distances between the first objects and the second objects based on a spatial proximity estimation distance analysis associated with extracted bounding geometries of a surface mesh of first data objects with respect to nearest second data objects.

In accordance with yet another disclosed embodiment, the progressive spatial analysis of the disclosed system and method, further comprises defining a first polygon based on the minimum boundary information associated with a first object and defining a second polygon based on minimum boundary information associated with one or more of nearest second objects of the first object. The disclosed system and method may further comprise generating a buffered boundary that surrounds the first polygon determined by the minimum boundary information associated with the first object; and determining an intersection between respective first polygon of the first data object and the second polygon associated with the one or more of nearest second objects. The disclosed system and method may further comprise duplicating the first object so that a first duplicate of the first data object resides within the first polygon; and the second duplicate resides outside a boundary of the second polygon associated with the one or more of the nearest neighbor objects; and determining a minimum distance between the first duplicate of the first data object and the one or more of the nearest neighbor second objects.

IN accordance with yet another disclosed embodiment, a computer readable device is disclosed storing instructions that, when executed by a processing device, performs operations. The operations include receiving minimum boundary information related to a first data object; and receiving minimum boundary information related to a second data object, the first data object and the second data object being proximate neighbors. Further disclosed operations include determining whether boundary data associated with the first data object is within an area delineated by the minimum boundary information of the first data object; and generating a first geometric structure associated with the first data object based on respective decompressed data associated with the first data object. Further disclosed operations include determining a structural skeleton using the first geometric structure associated with the first data object in order to identify its respective skeleton vertices; and generating a geometric representation based on the skeleton vertices associated the first geometric structure. Further disclosed operations include determining whether boundary data associated with the second data object is within the area delineated by minimum boundary information of first data objects; and identifying whether a centroid point of the second data object intersects the geometric representation associated with the first object. Further operations include determining a location of the centroid point of the second data object with respect to the first data object in order to identify a minimum distance between the first data object and the second data object.

IN accordance with yet another disclosed embodiment, a computer readable device is disclosed storing instructions that, when executed by a processing device, performs operations. The operations include receiving minimum boundary information related to first data objects, and receiving minimum boundary information related to second data objects. Further disclosed operations of the embodiment include initializing an array with the minimum boundary information related to the first data objects; and determining whether minimum boundary information associated with one of the first data objects is related to an area delineated by the minimum boundary information in the array. Yet further disclosed operations of the embodiment include determining whether a first area delineated by the minimum boundary information associated with the one of the first data objects intersects an area delineated by a second area delineated by the minimum boundary information associated with one of the second data objects. Yet further disclosed operations of the embodiment include generating a first geometric structure associated with the one of the first data objects based on respective decompressed data associated with the one of the first data objects; and generating a second geometric structure associated with the one of the second data objects based on respective decompressed data associated with the one of the second data objects. Yet further disclosed operations of the embodiment include determining whether a first geometric region defined by the first geometric structure intersects a second geometric region defined by the second geometric structure; and determining a spatial measurement of an intersecting region defined by an intersection of the first geometric region with the second geometric region. Yet further operations include identifying a first intersecting object and a second intersecting object associated with the intersecting region and respective volume information associated with the intersecting region.

IN accordance with yet another disclosed embodiment, a computer readable device is disclosed storing instructions that, when executed by a processing device, performs operations. The operations include defining a first polygon based on the minimum boundary information associated with a first object and defining a second polygon based on minimum boundary information associated with one or more of nearest second objects of the first object. Further disclosed operations of the embodiment include generating a buffered boundary that surrounds the first polygon determined by the minimum boundary information associated with the first object; and determining an intersection between respective first polygon of the first data object and the second polygon associated with the one or more of nearest second objects. Further disclosed operations of the embodiment include duplicating the first object so that a first duplicate of the first data object resides within the first polygon, and the second duplicate resides outside a boundary of the second polygon associated with the one or more of the nearest neighbor objects. Further disclosed operations of the embodiment include determining a minimum distance between the first duplicate of the first data object and the one or more of the nearest neighbor second objects.

These and other purposes, goals and advantages of the present application will become apparent from the following detailed description read in connection with the accompanying drawings.

BRIEF DESCRIPTION OF THE DRAWINGS

Some embodiments or aspects are illustrated by way of example and not limitation in the figures of the accompanying drawings in which:

FIG. 5 illustrates an embodiment of workflow of the 3D spatial query system in which a step-by step algorithm delineates each step of the workflow.

FIG. 14A is an illustration providing the general framework of 3D spatial query data processing, in accordance with an embodiment of the disclosed system and method.

FIG. 15C illustrates an example spatial join query algorithm, in accordance with an embodiment of the disclosed system and method.

FIG. 16B shows an algorithm associated with the Nearest Neighbor (NN) query, in accordance with an embodiment of the disclosed system and method.

FIG. 17C shows an algorithm associated with the spatial proximity estimation, in accordance with an embodiment of the disclosed system and method.

Figure 1A:
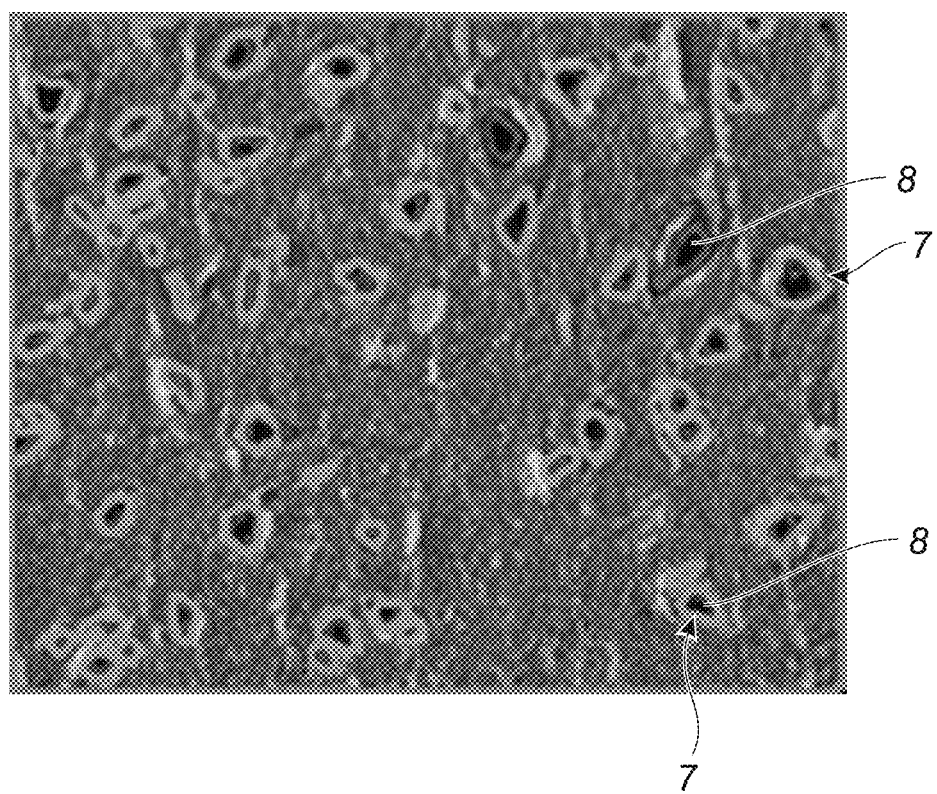
FIG. 1A illustrates a sample digital pathology image including complex objects subject to image analysis using 3D spatial query, in accordance with an embodiment of the disclosed system and method.

It is to be appreciated that elements in the figures are illustrated for simplicity and clarity. Common but well-understood elements, which may be useful or necessary in a commercially feasible embodiment, are not necessarily shown in order to facilitate a less hindered view of the illustrated embodiments.

DETAILED DESCRIPTION

A system and method of performing on-demand in-memory based progressive spatial queries associated with 3D data complex structures are disclosed herein. The disclosed system and method implements data compression, multi-level indexing and data decompression for processing multiple types of spatial queries on prodigious 3D data including complex 3D data, and in certain embodiments, complex data related to biological structures as vessels and cells.

In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

The disclosed system and method including a 3D data compression approach makes it possible to significantly reduce data size to operate the data in memory at very low memory footprints with effective compression and on-demand decompression, which leads to much reduced I/O and communication cost for query processing. The disclosed system and method is directed to modeling 3D objects with multiple levels of detail for spatial queries, which provides options for users to determine their goals during processing which results in speedier queries and/or higher accuracy to meet application specific requirements.

Further disclosed is a multi-level in-memory spatial indexing to reduce search space and accelerate queries. In particular, unique structural indexing techniques are disclosed for searching using complex structured objects, which significantly improves query performance compared to traditional MBB based indexing.

Further disclosed is an on-demand in-memory based 3D spatial query engine that fully takes advantage of multi-level indexing and data decompression for processing multiple types of spatial queries, which can be implemented for example, using MapReduce or other distributed computing paradigms.

Preliminary studies do demonstrate that the disclosed system and method achieves significant benefits on efficiency and scalability of spatial queries over traditional non-memory based 3D spatial query systems.

It is known in pathology and related analysis of complex 3D data structures, that common biological objects extracted from pathology images include nuclei or cells, fats, blood vessels, ducts, and others. While nuclei have relatively simple shapes, blood vessels and ducts could have complex structures, such as bifurcations with multiple branches. The spatial relationships and distribution patterns among these objects play a critical role for understanding of tumor microenvironment and investigations of disease progression. The disclosed system and method helps facilitate this critical role in understanding tumor microenvironment and investigations of disease progression.

3D image analysis of whole slide image volumes produces large amount of quantifications such as 3D spatial objects and features. In a typical 3D analytical pathology imaging pipeline, selected biopsies are sectioned into thin slices and mounted on physical glasses. These slides are then scanned into digital images to form 3D image volumes. With the image volume, micro-anatomic objects of interest such as blood vessels and cells are reconstructed in 3D models. Finally, the 3D objects as well as their extracted features are managed and queried by a spatial data management system.

Models for 3D object representation, such as a mesh based approach can be implemented using polyhedral modeling. In an embodiment of the disclosed system and method, 3D objects are represented for example, in geometry definition file format OFF. The mesh model with OFF specifies both the geometry (shapes, sizes and absolute positions) and topology (relationships among elements).

The advent and proliferation of spatial data exploration has resulted in a greater need for more effective feature queries and spatial queries. The disclosed system and method implements novel 3D spatial queries. In particular, three representative data and compute-intensive 3D spatial queries are implemented: (1) spatial joins/cross-matching, (2) nearest neighbor query; and (3) spatial proximity estimation which will be described in greater detail hereinbelow.

3D Spatial Join or Cross-matching overlay problem is an example embodiment of a spatial query that involves identifying and comparing 3D objects from different observations or analyses. In 3D pathology imaging, spatial cross-matching is often used to compare and evaluate 3D image segmentation or reconstruction results, iteratively develop high quality image analysis algorithms, and consolidate multiple analysis results from different approaches to generate more confident results. Spatial cross-matching can also support spatial overlays to combine information of massive spatial objects between multiple layers or sources of spatial data, such as remote sensing of 3D datasets from different satellites. In addition, spatial cross-matching can also be used to explore temporal changes of 3D topographic maps between historical snapshots.

FIG. 1A is a sample digital pathology image including complex objects of different types (7, 8). Often time digital pathology requires analysis of nuclear morphological and functional features that can carry prognostic value. Certain pathologic hallmarks are analyzed. Such analysis is implemented in the form of spatial analytics in order to study progression of cells including for example, tumor progression and such analytics helps in understanding the dynamics of disease, by analysis of, for example, tumor microenvironments. Such spatial analysis is relationship based. Hence, the system identifies only cells of interest contained within or within certain distances of certain blood vessel(s), for example. Spatial join is used to compare two spatial datasets to find spatial relationships. Certain analysis is distance based spatial density, nearest neighbor and proximity estimation. Spatial density computes 3D histograms of cell density in space. Nearest neighbor finds the closes vessel for each cell. Proximity estimation analyzes distributions of different types of objects. Global patterns are also useful such as spatial clusters or spatial point patterns for digital pathology image analysis of complex structures. In particular is disclosed the spatial relationships among derived 3D biological objects and determination of correlations across spatial patterns of the respective biological objects, disease progression and corresponding genomic signatures. 3D data compression, storage, indexing and querying methods are implemented in order to achieve useful and concrete analysis of 3D digital images. Biological structures often present as complex 3D structures and representations associated with bifurcations in the blood vessels, for example. Such complex structures present with multiple levels of details (LOD) as shown and described hereinbelow in FIG. 8B. Such complex 3D structures necessarily present high computational complexity and require complex geometric computation to generate concrete and useful results for further pathologic analysis, observations and determinations.

The disclosed memory-based 3D spatial data management query system and method takes advantage of memory to store data and indexes, and minimize I/O inefficiencies, communication and related costs. It supports effective and scalable spatial queries and analytics using various paradigms and infrastructures. The query system supports effective progressive compression for individual 3D objects. The disclosed query system effectively implements in-memory based data storage and indexing solutions. Multi-level spatial indexing and on-demand 3D spatial query pipelines scalable for various paradigms (for example, Hadoop) are supported.

Figure 8A:
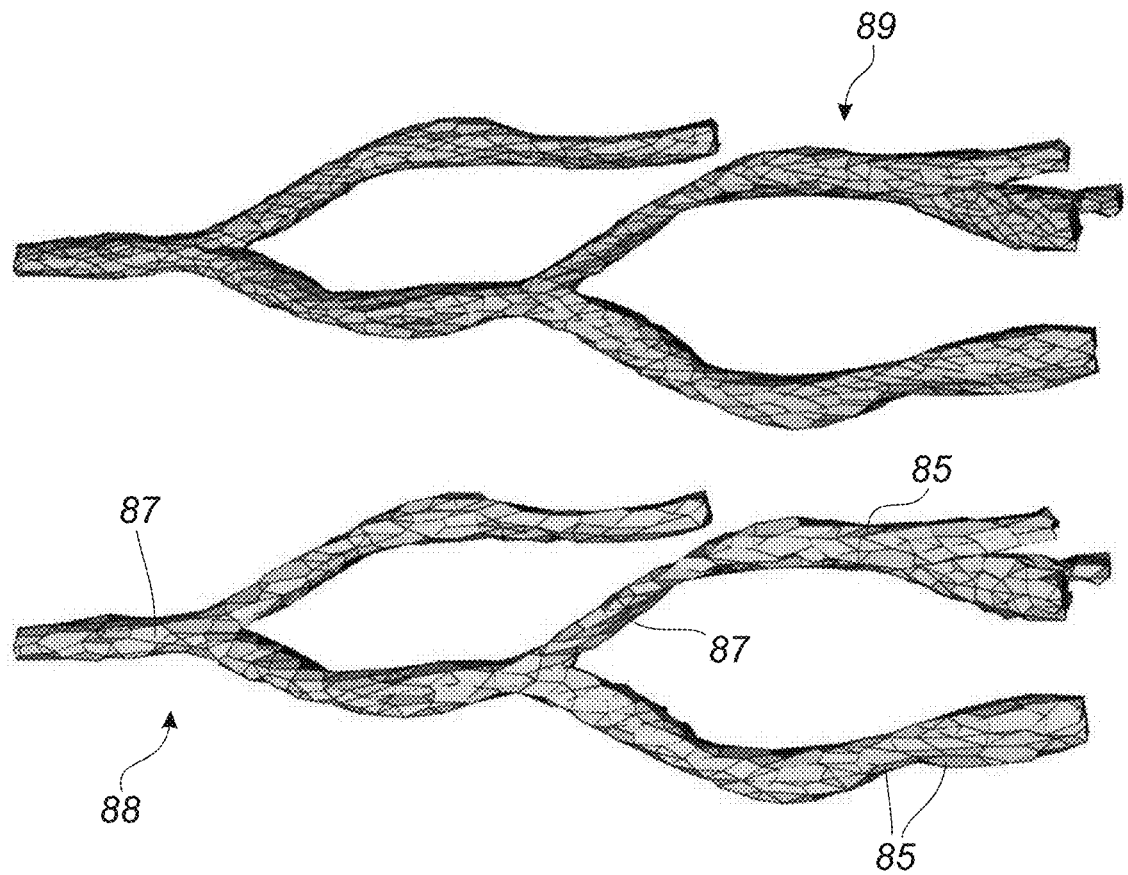
FIG. 8A is an illustration of decimation of an intermediate level of detail (LOD) of the 3D blood vessel model in accordance with an embodiment of the disclosed system and method.
Figure 8B:
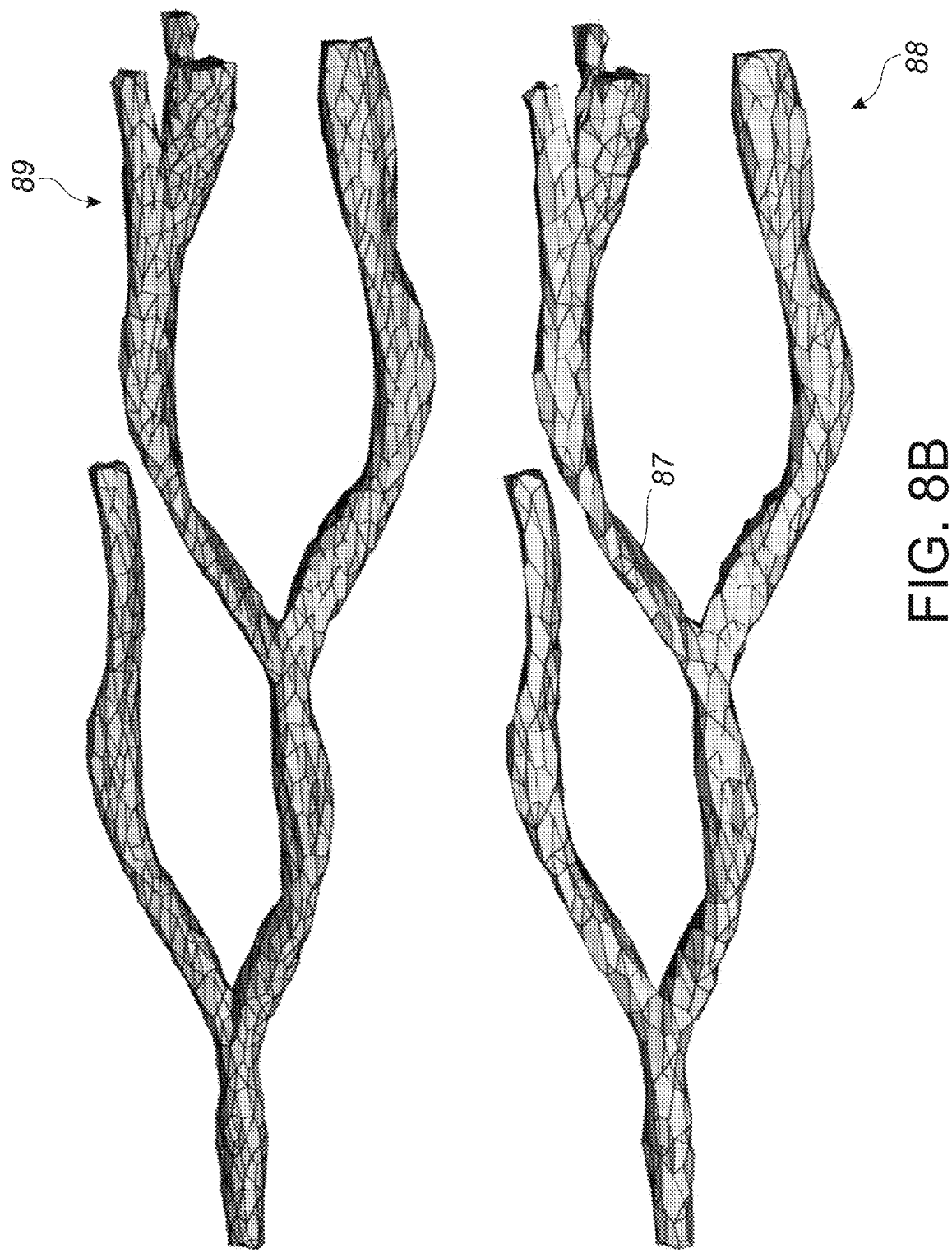
FIG. 8B is an enlarged view of an illustration of decimation of an intermediate level of detail of the 3D blood vessel model, as shown in FIG. 8A, in accordance with an embodiment of the disclosed system and method.

In practice, 3D objects are commonly represented with multiple resolutions with different Level of Detail (LOD) of blood vessels 3 as shown in FIG. 8B. The left rendering 89 illustrates a $L^i$ level of detail of a 3D blood vessel model. The right blood vessel rendering 88 illustrates the $L^{i-1}$ level of detail with inserted edges depicted in differing shades of faces with a removed vertex in darker shades. For instance, Google Earth uses a LOD mechanism to allow efficient 3D region rendering for map visualization. In digital pathology, a practitioner quickly visualizes rough 3D shapes of blood vessels to explore spatial relationships, and another explores 3D structure details for finer calculation of vessel features. LOD in higher resolution provides more accurate results for spatial computations, but could significantly increase data volume and computation cost. Thus, the disclosed 3D spatial querying system and method balances accuracy and computational costs.

Figure 1B:
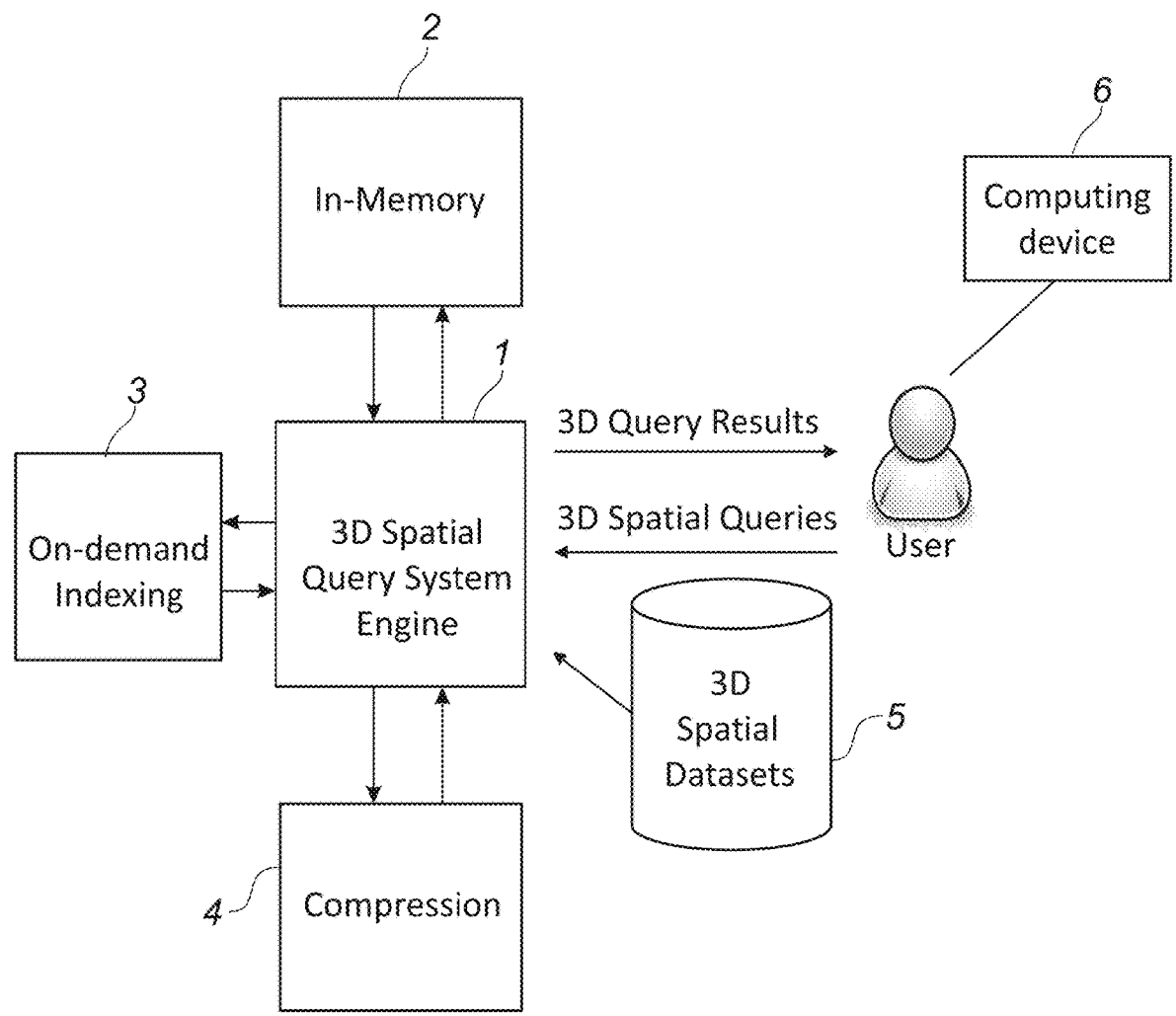
FIG. 1B is an overview of the 3D spatial query system, in accordance with an embodiment of the disclosed system and method.

Shown in FIG. 1B, is an embodiment illustrating an overview of the spatial query system and method associated with analysis of complex 3D structures, such as blood vessels and cell structures, two different object types as shown in FIG. 1A. A system and method of perform on-demand indexing 3 and in-memory 2 based 3D spatial queries associated with complex structures, such as blood vessels and cells are disclosed herein. In particular, the disclosed system and method implements data compression 4, multi-level on-demand indexing 3, and data decompression for processing multiple types of spatial queries using the 3D spatial query system engine 1, including queries associated with complex 3D data structures that in some embodiments is stored as 3D spatial datasets 5. The embodiment implements two types of structural indexing: skeleton based and hierarchical tree based, which significantly accelerate distance based queries compared to traditional MBB type indexing. The contemplated embodiment of the spatial query system provides a core engine 1 to support multiple types of spatial queries generated by computing device 6. The various kinds of spatial queries include: spatial join, nearest neighbor search, and spatial proximity estimation. Such spatial queries can be easily extended to others such as containment query. Described in greater detail hereinbelow, are the details of the 3D spatial query process and the workflow in each spatial query pipeline.

In one disclosed embodiment of a 3D spatial query is the 3D Nearest Neighbor Query. Nearest neighbor query (NN) is a well-studied problem that arises in numerous fields of applications. In particular with regard to 3D pathology image analysis, pathologists are interested in objects with spatial patterns as they present biologically meaningful correlations and prognostic values for the practitioners and research facilities. In clinical research, it is known that tumor areas often form groups of cells close to blood vessels for more nutrition and oxygen. Thus, one example query of interest to pathologists is that for each cell, the nearest 3D blood vessel is determined, and a return of the distance value between the cell and nearest 3D blood vessels is determinable. The example, 3D nearest neighbor query, can also support the determination of the closest post office in a 3D map navigation, or discover the top k nearby targets in 3D gaming by k-nearest neighbor search.

Figure 2:
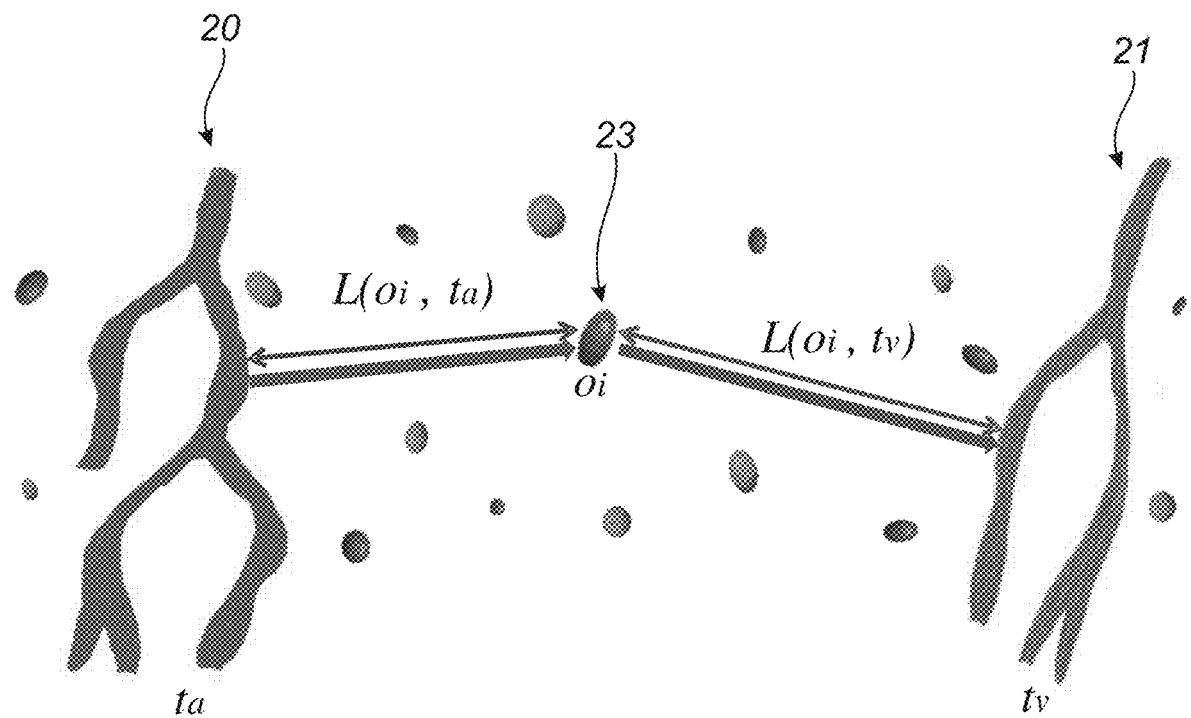
FIG. 2 is a diagram illustrating an example of 3D spatial proximity estimation of artery (dark) and vein (light).

In another embodiment of the disclosed 3D spatial query and system, is spatial proximity estimation, which aims to explore inter-objects distribution in 3D space based on distances between neighboring objects. In 3D digital pathology, spatial proximity estimation provides the quantitative expression of vascular spatial patterns for disease progression assessment. For example, the disclosed system and method determines at the behest of a liver pathologist, that for each cell in liver tissue, the shortest path of the cell 23 to its neighboring artery vessel 20 is desired and the shortest path to its neighboring vein vessel 21 as shown in FIG. 2. The disclosed system and method then computes the average and standard deviation (dispersion) of the full path that adds the two paths $L(o_i, t_a)$ and $L(o_i, t_v)$ as shown in FIG. 2.

Specifically, an example embodiment of such 3D spatial proximity estimation is shown in FIG. 2, with respect to neighboring complex structures, for example shown, arteries 20 and veins 21. Illustrated is a 3D spatial proximity estimation of artery 20 (left vessel in red) and a vein 21 (right vessel in blue) of neighboring cells 23. The neighboring cell 23 is used as a reference point in space to connect the blood vessels and veins that are closest to each other spatially. The query system computes the distribution between the two neighboring structures using close distances of cells to the structures in space. Since the structures have various aberrations, the points on each structure that generates the shortest distance between a neighboring cell, Oi 23 in space, is used as the reference point to essentially compute the shortest distance and connect the two structures (20, 21) by computed distance values, $L(o_i, t_a)$ and $L(o_i, t_v)$. The nearest neighbor query is described in greater detail with respect to FIGS. 16A-16C, as described hereinbelow.

In a disclosed embodiment, the 3D spatial query is implemented by using a set of basic objects $o_i$, and multiple types (a to m) of target objects $t_a, t_b, \ldots, t_m$. For each basic object $o_i$ (e.g., a cell) and each type of target objects $t_j$ (e.g., artery or vein), the corresponding shortest distance ($L(o_i, t_j)$) is computed by a computing device or processor, and the sum of the shortest path $\Sigma(o_i, t_j)$, j=a to m is further determined. Then for all cells, the mean and standard deviation of $\Sigma L(o_i, t_j)$ are computed as the spatial proximity measurement among target objects $t_j$. In summary, spatial proximity estimation is a special query that relies on extensive nearest neighbor search for massive number of objects for aggregation and related statistical analysis.

Figure 3:
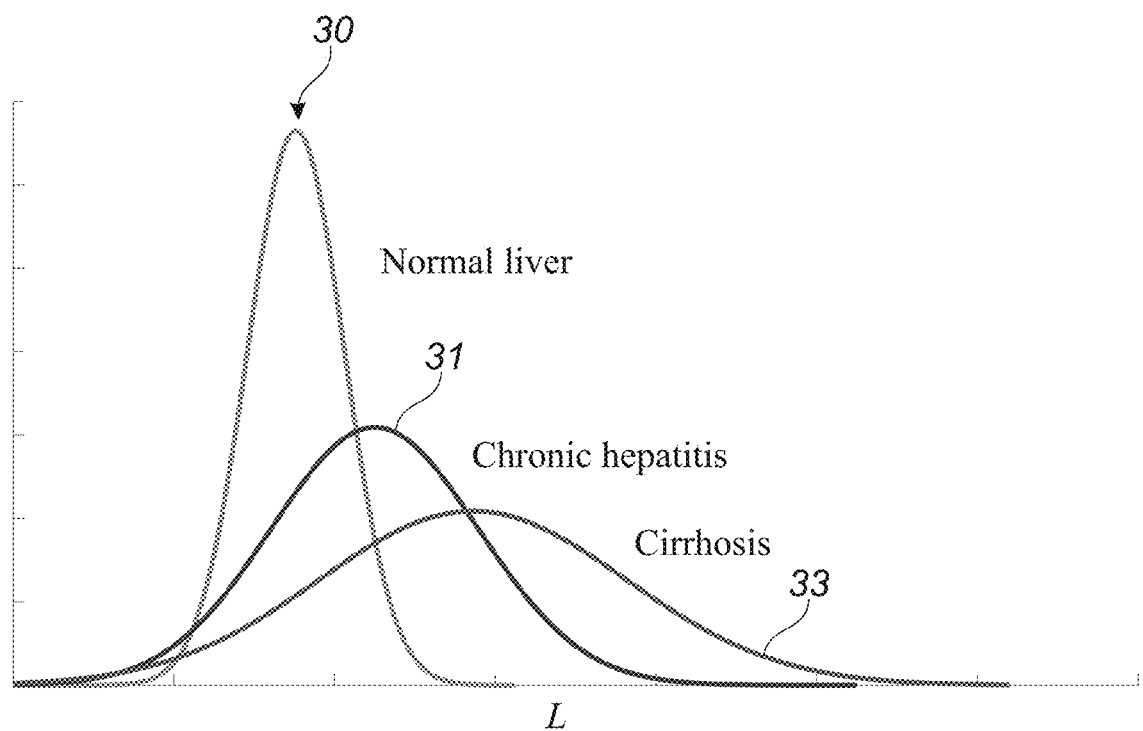
FIG. 3 illustrates in graph form, the spatial distribution of distance L between the cells, and the respective vessel or artery in normal and abnormal livers.

In digital pathology, spatial proximity estimation can further demonstrate different spatial distribution patterns of vasculature in different organs. Liver and lung present isodistant patterns, while renal cortex present as contiguous distribution. For liver, spatial proximity estimation supports quantitative progression assessment of normal livers over chronic hepatitis to cirrhosis, as the dispersion describes how much the vasculature is deviated from its normal state as shown in FIG. 3. FIG. 3 illustrates in graph, the spatial distribution of distance L as determined by the 3D spatial query system or engine, between the cells, and the respective vessel or artery in normal and abnormal livers. The sum of Ls for each cell, provides a histogram of distribution of 3D spatial proximity estimations. The abnormal liver indicated by curve 33, is indicative of cirrhosis and is further indicative of liver cancer. The normal liver distribution pattern is shown as curve 30. Chronic hepatitis is shown by curve 31. The respective dispersion of the slopes is shown by curves 30, 31 and 33, with curve 30 being normal and curve 33 being abnormal.

Among other benefits of the disclosed 3 D spatial query system and method (in-memory spatial query system for three dimensional spatial data) is to mitigate potential high I/O and communication costs, exploit indexing techniques for complex objects to accelerate queries, and provide high scalability to run on large computer clusters or computing clouds.

Figure 4:
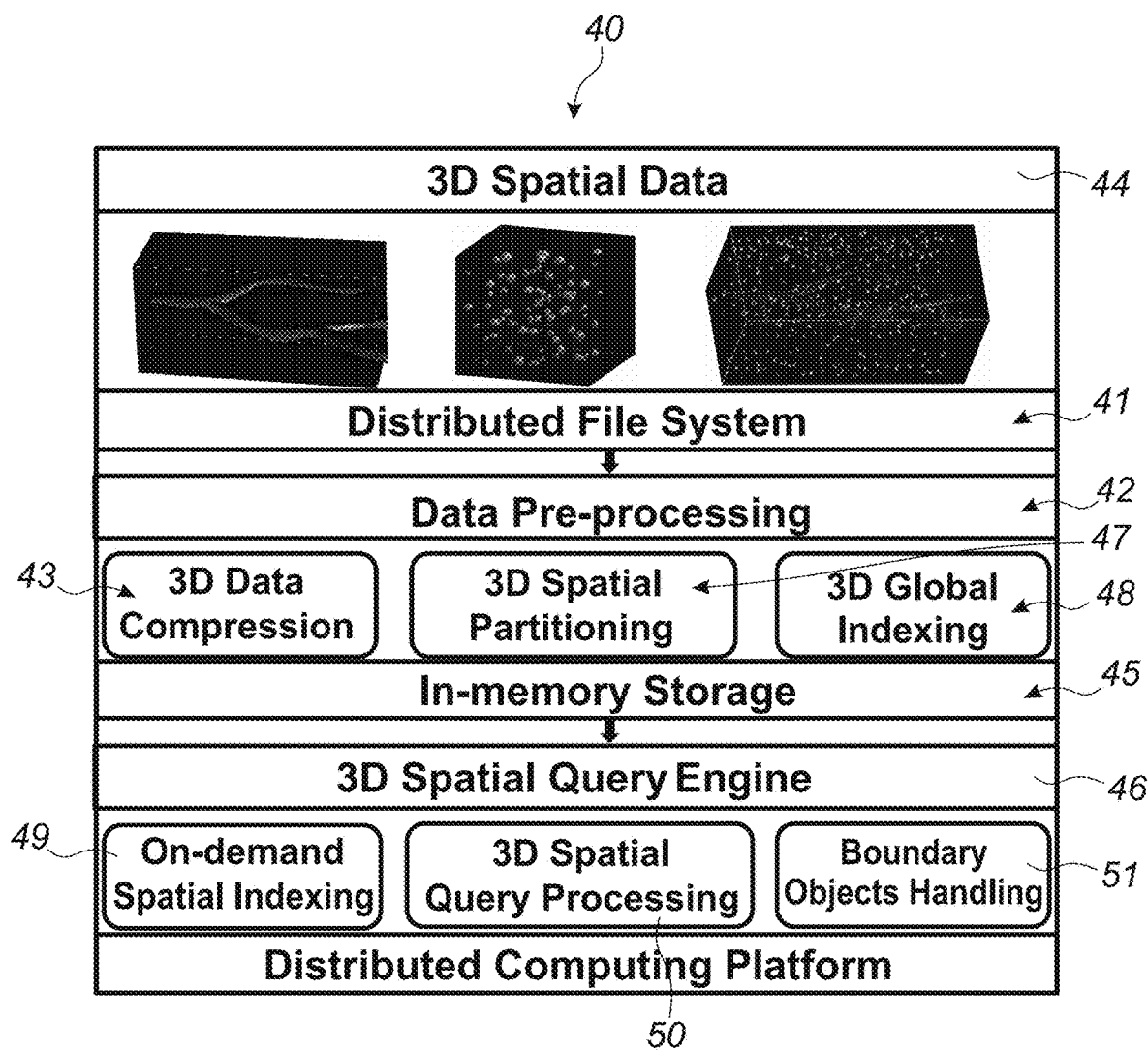
FIG. 4 is an architectural overview of the disclosed system and method of 3D spatial query of 3D complex data.

The architectural overview 40 of an embodiment of the disclosed system and method is shown in FIG. 4. After the raw 3D spatial data 44 is staged in a distributed file system 41 such as for example, HDFS, a data pre-processing step 42 is performed for data compression 43, 3D spatial partitioning 47 and 3D global indexing 48. The 3D spatial query system (and/or engine) 40 implements an effective progressive compression approach 43 that compresses each 3D object individually with successive levels of detail (LODs). After compression 43, each compressed 3D geometric object is stored in memory 45, and a master object index 48 is generated to track the MBB and in-memory location of each compressed complex data object.

Pre-processing 42 also provides spatial data partitioning 47 to generate partitioned cuboids which form the unit of parallel respective query tasks. Partitioning 47 generates in a disclosed embodiment, two level global spatial indexes 48: partitioned cuboid index to represent the MBB of all cuboids, and a subspace index to group neighboring cuboids into large subspaces to form a higher level spatial index. Since generally MBBs are implemented, these indexes are small enough to be stored in memory 45.

In addition to the compressed data and global indexes pre-stored in memory, the system also creates on-demand spatial indexes 49 in memory during query processing by the 3D spatial query engine 46. The index 49 is used, in certain embodiments, to accelerate the queries. On-demand spatial indexing 49 includes an object-level index which is based on the MBBs of all objects within a single partition (cuboid), and a structural index for individual complex structured objects, such as blood vessels. Therefore, the 3D spatial query engine implements on-demand spatial indexing 49, 3D spatial query processing and boundary objects handling 51 protocols to implement various queries of 3D complex structures. In the disclosed embodiment, the proposed multi-level spatial indexing 49 includes the global indexing and the on-demand local indexing.

The disclosed system provides an on-demand in-memory three dimensional spatial query engine to run query tasks. The spatial query engine can be invoked on-demand to run many instances in parallel. For each query task, the IDs and MBBs of the 3D objects contained in the partitioned cuboid are identified with the master object index, and the 3D spatial query system creates an in-memory index such as an R*-tree for query processing. Note that in the disclosed embodiment, the index only contains MBBs, thus its size is relatively small in terms of memory storage.

A typical spatial query such as spatial join, normally starts with an MBB index (object-level spatial index) based filtering to identify potential object pairs with the specified spatial relationship. Only at the refinement or spatial measurement step, are the original geometries required for geometric computations such as for example, computing if two polyhedrons intersect or have an intersecting volume. The spatial query system obtains compressed 3D objects from memory, and decompresses the objects based on a specified level of detail (LOD) and transmits the objects to the query engine. A typical query task runs on a single core and has a sequential processing pipeline, and only a very small number of objects are loaded at a time, which generally uses a small amount of memory space.

The disclosed embodiment further provides for parallel querying pipelines for multiple spatial query types, with partitioned datasets as the basis for parallelization. Query parallelization can be implemented through distributed computing paradigms, such as for example, Hadoop. As there may be objects crossing boundaries during data partitioning, each query pipeline will provide additional results and a respective normalization task to amend the results as may be required.

Figure 6:
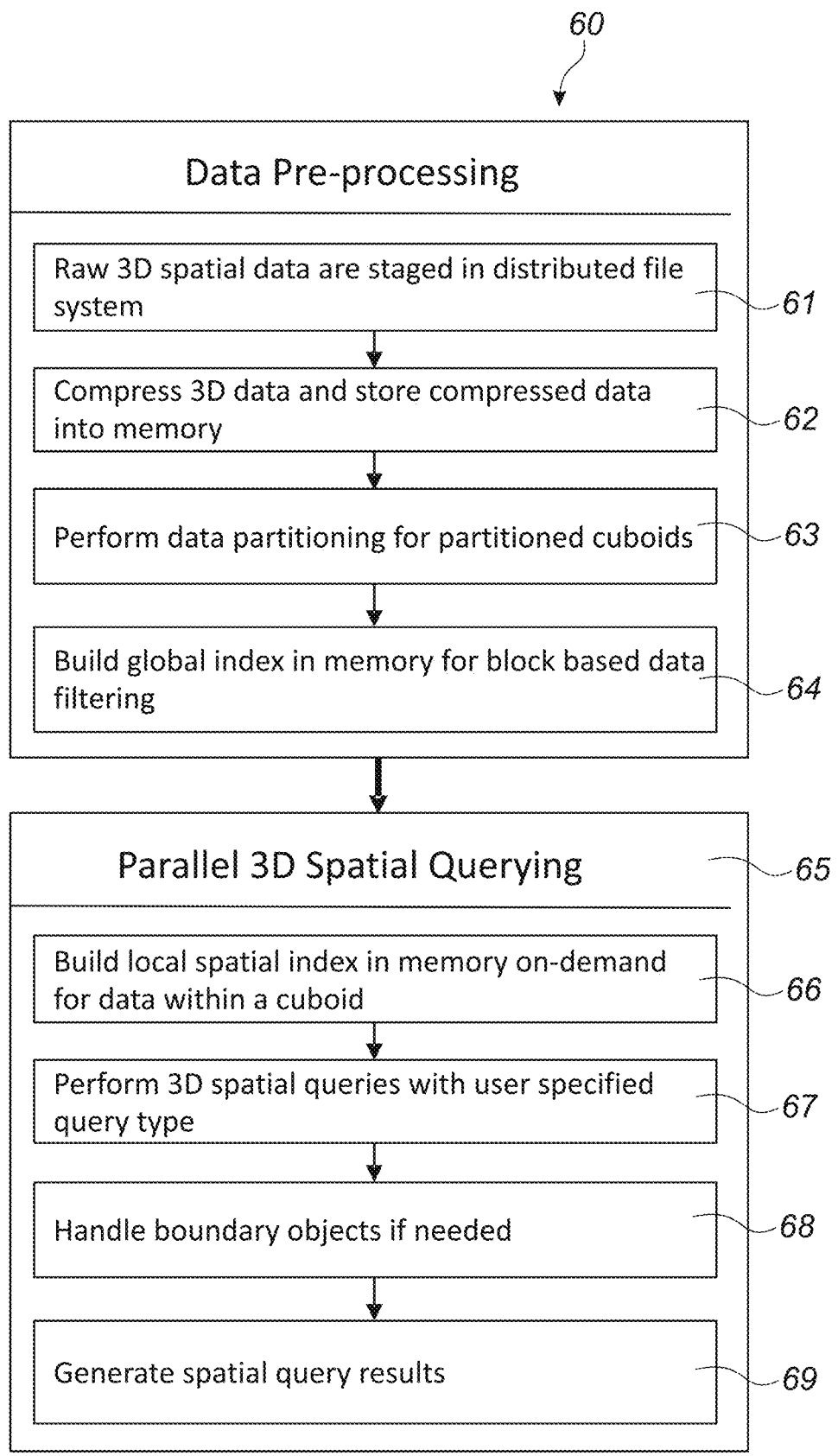
FIG. 6 is a flowchart of an embodiment workflow of the 3D spatial query system as also shown in delineated steps of FIG. 5.

A typical workflow of the 3D spatial query system is presented in FIG. 5 in which a step-by step algorithm indicated each step of the workflow is delineated. In step A of FIG. 5, the 3D spatial objects are staged in a distributed file system, as also shown in FIG. 6. The system at step 61, performs staging of raw 3D spatial data into a distributed file system. Then data compression and spatial partitioning are performed as part of pre-processing 60, FIG. 6 and Step B of FIG. 5. Step C of FIG. 5 next stores the compressed data and global indexes into memory, as also illustrated in step 62 of FIG. 6. Step D of FIG. 5 executes partitioned cuboid based spatial query processing in parallel on distributed computing platforms, as further shown in step 63, FIG. 6. In parallel 3D spatial query processing shown in step 65, FIG. 6, 3D objects within one cuboid are first identified by the system using a task filtering process including partitioned cuboid index(es), as shown in element 64, FIG. 6. However, for objects within the same cuboid, an object-level index is built on demand in step 66. The spatial queries starts with an MBB filtering step 67, and the desired actual geometries are decompressed during the refinement step. Step E of FIG. 5 performs boundary objects handling if needed, and as further shown in step 68, FIG. 6. Step F, FIG. 5 provides post-query processing such as final results of aggregation. The result(s) of the spatial querying is generated in step 69 of FIG. 6.

It is noted that 3D spatial data is often represented with high precision models, leading to complex meshes and large sizes. In order to reduce I/O and communication cost for query processing, the disclosed embodiment implements an effective progressive compression approach to compress each 3D object individually with successive levels of details (LODs). At the same time, the MBB of each object is extracted and a master object index is created in order to record the MBB and the location of each object. Both the highly compressed geometry data and the master object index are stored in memory with limited memory footprint for efficient data processing with significantly improved computational efficiencies than known systems. Example embodiment(s)s of compression techniques employed by the 3D spatial querying system and method are described hereinbelow with respect to FIG. 19A and FIGS. 22-22B, including user specification of level of detail (LOD) for implementation by the 3D spatial query system during compression.

In practice, a speedier response is a significant requirement of spatial queries which may be implemented in various applications, such as exploratory studies on massive amounts of spatial data with a large set of parameters and algorithms, and decision making in healthcare applications. Spatial partitioning and indexing are two fundamental techniques to support scalable and efficient spatial queries in most distributed database systems.

In order to achieve scalability, the system provides spatial partition level parallelism which in certain embodiments is mapped into various parallel computing paradigms such as, for example, MapReduce. Specifically in a 3D space embodiment, by partitioning the input data into partitioned cuboids, the data contained in each cuboid can be stored and manipulated by the processing unit which permits an increased level of parallelism and hence improves overall throughput.

Once any cuboids are generated, processing tasks are not dependent on any others including third party users and/or systems components for exchanging information, thereby significantly reducing any idle CPU time. Using a proper data partitioning mechanism in accordance with the disclosed system and method, I/O costs can be notably decreased by limiting the tasks to scanning partitions containing relevant data to the query.

Various partitioning methods are available and can be selected based on data characteristics such as data skew and query types. For digital pathology, the distributions of biological objects such as cells, are relatively homogenous compared to geo-spatial data. Therefore, in one embodiment, a fixed-grid based partitioning approach is suitable for handling partition on distributions of biological objects.

Figure 7:
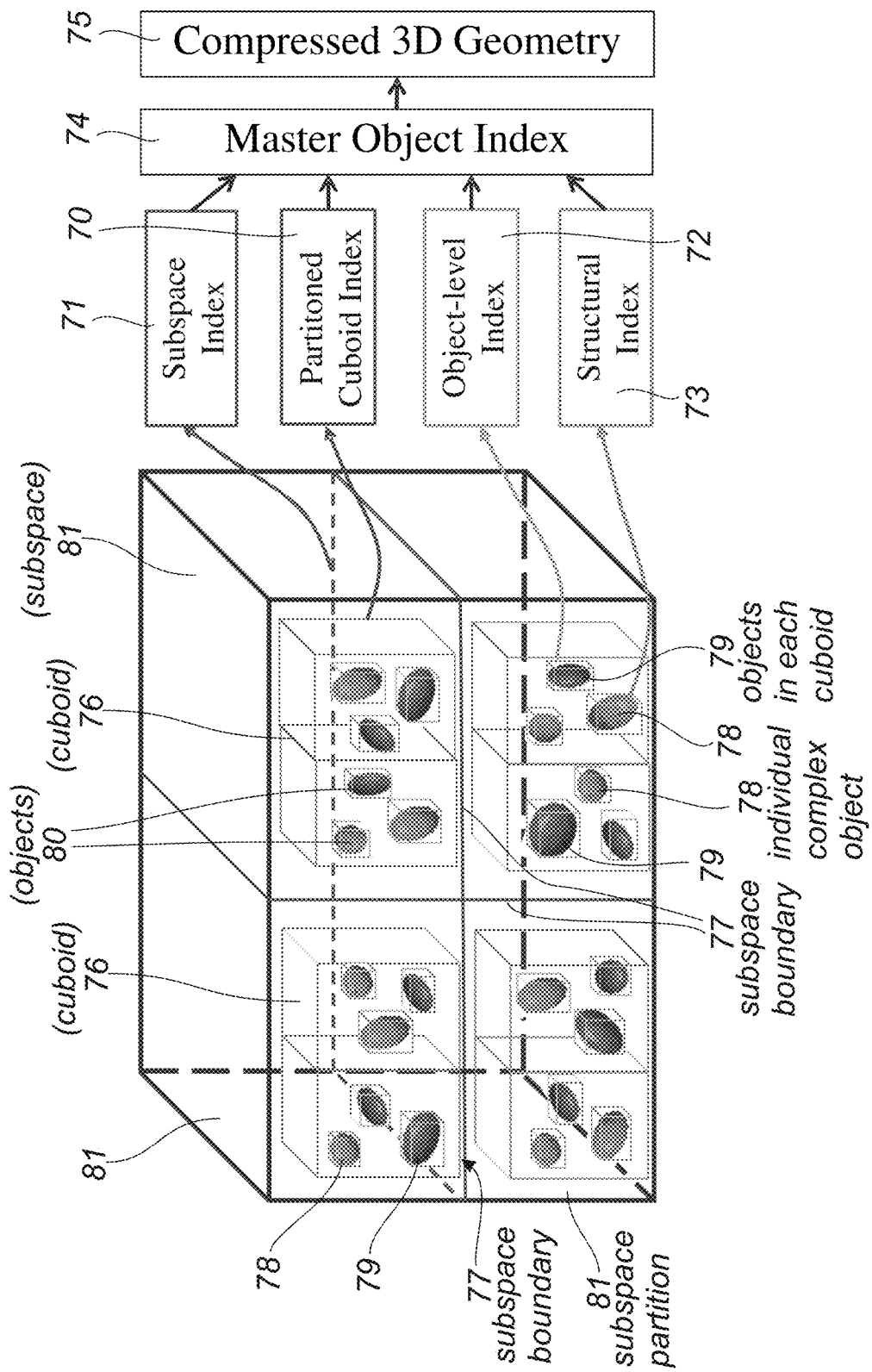
FIG. 7 illustrates a hierarchical view of multi-level indexing in accordance with an embodiment of the disclosed system and method.

In accordance with a disclosed embodiment, the partitions are used to form two levels of global spatial indexes: partitioned cuboid indexing based on the partitioned cuboids, and subspace indexing based on aggregation of neighboring cuboids, as shown in FIG. 7. In particular, illustrated in FIG. 7 is a hierarchical view of multi-level indexing.

Hence, global spatial indexing is based on partitions. The partitions can be used to form two levels of global spatial indexes: partitioned cuboid indexing based on the partitioned cuboids; and subspace indexing based on aggregation of neighboring cuboids.

Partitioned cuboid index is used to manage the containment relationships between each partitioned cuboid 76 and its containing objects 80. A "cuboid_id" is generated for each cuboid 76 during a spatial partitioning phase based on its corresponding MBB (minimal bounding box). As objects in a partitioned cuboid 76 forms the unit of parallelization tasks, "cuboid_id" can be used as a key to group 3D objects contained in this cuboid 76, which serves as effective task-level computational filtering.

The subspace index 71 is generated by the disclosed computing or processing system and method, on subspaces 81 which are sub-divided out based on the partitioning of cuboids 76 which surround respective objects 80 being analyzed. Type 1 objects are shown bounded by MBB 78 and a type 2 object 79 bounded by another MBB 79, which in turn are bounded by cuboids 76. Each object is enclosed by its own MBB as shown. A subspace 81 is a higher level 3D box that is generated on top of (or larger than but surrounding) respective partitioned cuboids 76, which in turn are generated on top of (or larger than but surrounding) respective first object type 79 MBBs and second object type 78 MBBs, in a systematically dividing format of 3D spatial subdivisions. Subspace indexing 71 is a coarse partitioning that systematically groups multiple neighboring cuboids 76 into a subspace 81, also as shown by dotted line and subspace boundary lines 77 formed around cuboids 76, which create a subspace partition 77 for each subspace 81, as shown in FIG. 7. Thus, a subspace spatial index 71 is created to maintain relationships between subspaces 81 and the containing partitioned cuboids 76 (also indexed in the partitioned cuboid index 70) based on MBBs. Subspace indexing 71 can be used to effectively support window based queries by filtering irrelevant subspaces not relevant to the query.

An R*-tree is implemented in a disclosed embodiment of the 3D query system and method, in particular, for two-level global spatial indexing. As data is read-only with no further updating occurring, the indexing process is optimized by bulk-loading techniques, including setting the page utilization ratio as for example, at 100% in order to minimize the number of generated pages. FIG. 7 shows a hierarchical view of the indexes (70-74) generated by the disclosed 3D spatial proximity system and method, including a master object index 74 which indexes the massive compressed 3D geometry 75 that includes complex objects; the subspace index 71; the partitioned cuboid index 70; the object-level index 72; and the structural index 73.

Besides the partitioned cuboid 70 and subspace 71 indexes, an object-level spatial index 72 is generated in an embodiment of the disclosed system and method, for objects contained in each cuboid 76, and a structural index 73 is created for individual complex objects 78, such as blood vessels, which are discussed in greater detail hereinbelow. These spatial indexes have finite, limited sizes, and are stored in memory either at pre-processing phase (partitioned cuboid and subspace indexes) or on-demand (object-level and structural indexes). The master object index 74 is a non-spatial index which maintains the MBBs and acts as a pointer or index to respective in-memory locations of each 3D object (in particular, the compressed 3D geometry 75).

In yet a further embodiment of the disclosed 3D spatial query system and method, an in-memory three dimensional spatial query engine operates as a standalone, and is extended and customized to support multiple spatial queries. The system creates on-demand object-level indexing and/or structural indexing in order to accelerate spatial queries. The system can be parallelized with decoupled spatial query processing on individual partitions, to support multiple querying pipelines with optimal access methods, and provides result normalization to handle boundary objects. In particular, the system performs on-demand in-memory indexing for object-level indexing (for many objects contained in a partitioned cuboid) and structural indexing (for individual complex objects such as for example, blood vessels).

Implementations of the in-memory spatial query engine can be accomplished with for example C++ program, and can also implement open source libraries. In order to support 3D geometric computations, the Computational Geometry Algorithms Library (CGAL) can be adopted in certain implementations. SpatialIndex, for example, can be extended for 3D R*-Tree support in certain implementations of the spatial query engine.

Massive 3D data with complex structures generated from scientific studies, provides significant research challenges on spatial data management and analytics. The disclosed embodiment of the in-memory based system supports high performance 3D spatial queries on large scale complex structured datasets. The system achieves efficiency and scalability on supporting multiple spatial query types with 3D data compression and in-memory storage, multi-level spatial indexing, parallel query processing, and graceful boundary and buffered objects handling, which could not be accomplished by prior systems.

In a disclosed embodiment of the 3D spatial query system, the 3D data is compressed using the disclosed 3D data compression process including algorithm(s) which facilitates more efficient in-memory data storage.

3D mesh compression has been studied in a range of applications such as simulation, CAD and imaging, to reduce data sizes and alleviate the burden of network communication(s). The disclosed system implements a progressive polyhedron mesh compression algorithm and compresses individual 3D objects prior to indexing the 3D objects into memory. The compression generates successive levels of detail for a 3D mesh in order to meet different accuracy requirements.

As shown in FIG. 8A and a further enlarged view thereof, as shown in FIG. 8B, is an illustration of the outcome of performing decimation of a 3D blood vessel model. The 3D blood vessel model includes decimation including an intermediate level of detail. The vessel diagram 89 depicts a level of detail indicated as L. The vessel diagram 88 illustrates level of detail indicated as $L^{i-1}$, with inserted edges depicted in different shaded edges, and with a removed vertex indicated in a darker shade 87 for those particular facets.

In an embodiment, the compression process consists of three steps: Decimation: simplifies compression using a mesh Level of Detail indicated as LOD $L^i$ in order to generate $L^{i-1}$. The system progressively removes vertices and adds new edges 87 to the mesh. Patch and Edge Encoding step encodes the decimated meshes by producing three symbol lists to record the connectivity and geometry of the new mesh. For the LOD $L^i$, symbol list F indicates if a face has a removed vertex or not. $R^i$ records the residuals of any patches with a removed vertex 85. $E^i$ encodes which edges have or have not been inserted. Entropy Coding is a third step in which the three symbol lists are further compressed by the range coder.

Figure 9:
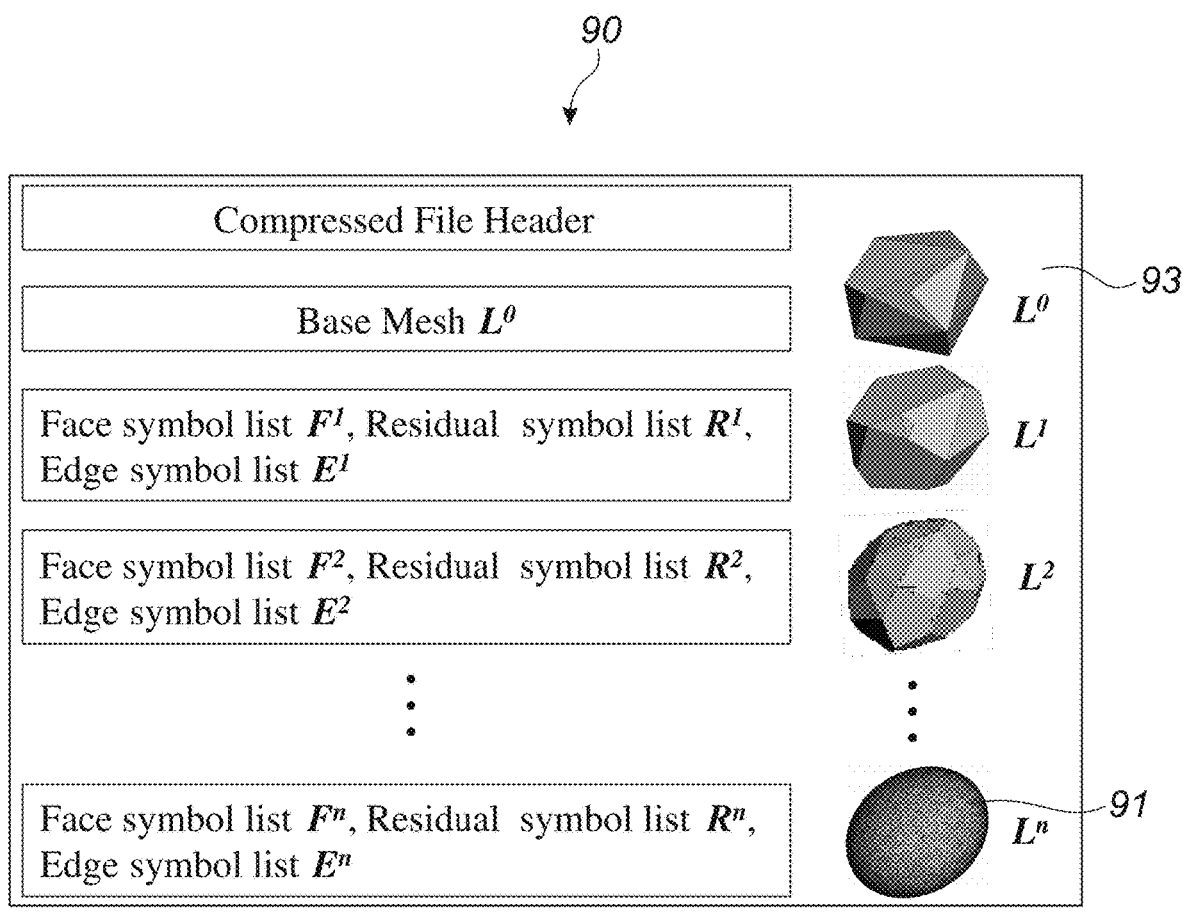
FIG. 9 is an illustration of the compressed file structure with a compressed nucleus illustrating different LODs.

One or more methods are used to prove the rate-distortion performance by a wavelet decomposition and an adaptive quantization technique. During data compression, the new mesh LOD $L^{i-1}$ contains about 30% less vertices compared the LOD $L^i$, and the base mesh $L^0$ is the lowest LOD. FIG. 9 is an illustration of the compressed file structure with a compressed nucleus illustrating different LODs as a result of the compression process. The compressed file structure 90 with a compressed nucleus 91 illustrating different LODs is shown in FIG. 9. The nucleus with the lowest level of detail which is the base mesh $L^0$ for nucleus 93. During data compression, indicated as $L^1$ the vertices are progressively removed with n being incremented and progressing to $L^n$. The LODs diminish and the final geometry of the nucleus model contains diminished vertices as depicted in compressed nucleus 91.

It is observed that as the data compression algorithm is not lossless, high compression rates could incur potential structure distortion. Spatial queries are performed on both the compressed data and the raw data for query results comparison, and on average the error rate is about 0.21% for spatial join query. As spatial data is generated from image analysis algorithms which themselves can manifest errors, since spatial queries involve massive number of 3D objects, for statistical purposes such precision loss is negligible in practice.

High caliber and effective compression enables data storage in memory, and the compression ratio depends on the structure complexity of the mesh object. Generally once compression is accomplished, the size of the base mesh $L^0$ is less than 1% of the total file size of the raw data, and the size of the whole compressed file with multiple LODs (for example, 10 levels in the setup) is only about 3% of the raw file size. For a typical 3D volume in digital pathology of 1 TB in size, the final size after compression is approximately 30 GB, which fits well into the memory of a computing cluster node.

While each 3D object is compressed individually, a master object index is created to track the MBB and the in-memory location of each object. The format of each record in the master object index is defined, as indicated hereinbelow as:

<object_id, dataset_id, object_class, MBB, offset, length>

The object_id is a unique ID for each object within the dataset with dataset_id and object class indicating object class such as nuclei or different vessel types. The offset and length indicate the byte offset and length of the object in the memory respectively. As an example, one record in the master object index on a nucleus dataset is (7, 1, 0, 177.317, 655.321, 187.249, 305.106, 782.82, 291.479, 4990, 807) where 7 and 1 mean the 7th nucleus object in dataset 1; 0 indicates the object_class of the nucleus; the following six numbers (177.317, 655.321, 187.249, 305.106, 782.82, 291.479) represent the MBB coordinates of the nucleus as ($x_{min}$, $y_{min}$, $z_{min}$, $x_{max}$, $y_{max}$, $z_{max}$); 4990 is the offset of current nucleus in the master object index, and 807 is the length of the compressed data. Both offset and length are indicated in bytes, in the example embodiment.

As each record contains only a few numeric fields, the master object index is small in size and can be stored in memory. For a typical 3D pathology volume of 1 TB data size, the master object index is generally about 1.2 GB in size.

In accordance with an embodiment of the in-memory based 3D spatial query engine that effectively implements the above-described compression techniques, the engine creates and implements, on-demand object-level indexing and structural indexing for spatial query acceleration, uses multiple querying pipelines with optimal access methods, and generates results including normalization to handle boundary objects effectively for various 3D pathology applications.

As described in connection with FIG. 7, object-level spatial indexing indexes all objects in each partitioned cuboid to support indexed based spatial queries. For example, joining objects from two cuboids can be supported through R-Tree based indexing techniques. While traditional SDBMSs (spatial database management systems) pre-create indexes, such indexes are fixed and generally require lots of space. Instead, the disclosed in-memory based 3D spatial query engine implements an on-demand based indexing approach by creating suitable indexes for the current query at runtime. This provides much flexibility and reduces storage, with very small overhead. The data and computation intensive spatial queries such as for example spatial join, require nominal overhead for index building on modern hardware.

Figure 10:
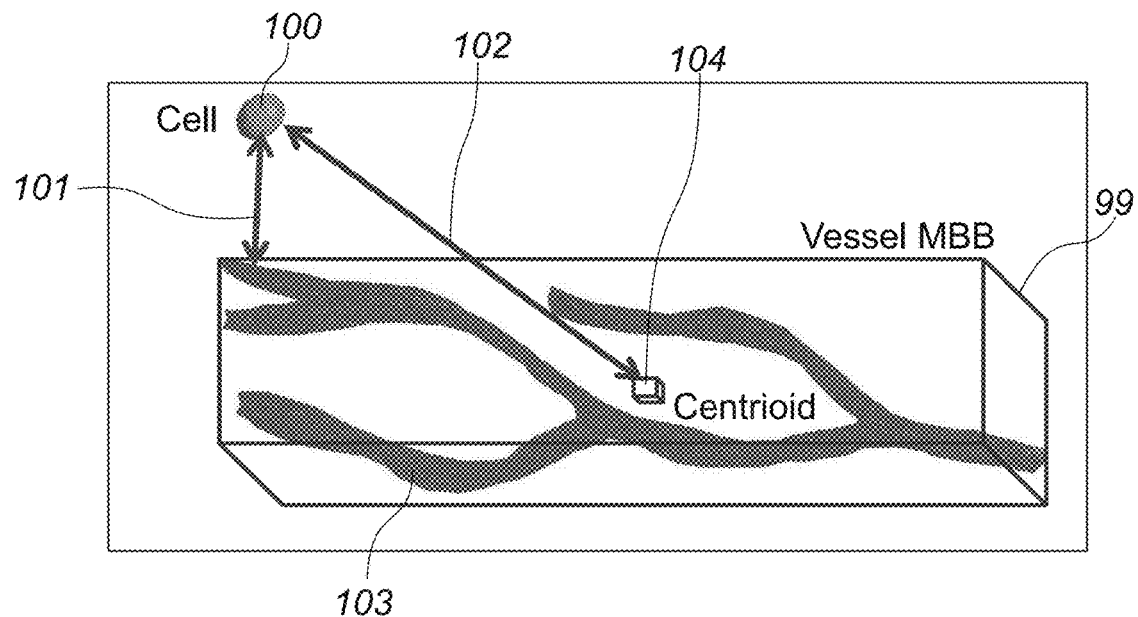
FIG. 10 is an illustration of the simplification of spatial objects with complex structure which generates computational inaccuracies in known systems.

For distance-based spatial queries such as nearest neighbor and spatial proximity estimation, traditional approaches always represent spatial objects with points for computation efficiency. This simplification is suitable for 3D objects with regular shape or simple structures, and approximate query results are needed. However, for complex structured objects such as blood vessels with bifurcations and branches within a MBB 99, point simplification results in erroneous query results with distance computation, as shown in FIG. 10. The actual shortest distance between the cell 100 and the vessel object 103 is designated by the line 101. However, if the vessel object 103 is simplified as its centroid 104, the distance is computed as shown in line 102, which is in effect not accurate.

In distance based queries such as FIG. 10, accurate distances between objects are required, and calculation of such accurate distances needs to traverse every component of the 3D objects. As one 3D object may contain thousands of primitives like vertices or facets, a naive MBB based brute-force traversal approach would be extremely expensive and computationally inefficient and inaccurate. Therefore, in accordance with an embodiment of the disclosed system and method, at least two novel structural indexing approaches are used to accelerate distance based spatial queries: topological skeleton based indexing and hierarchical Axis-Aligned Bounding Box (AABB) tree based indexing, such as illustrated in FIGS. 11A-11C.

Figures 11A, 11B, 11C:
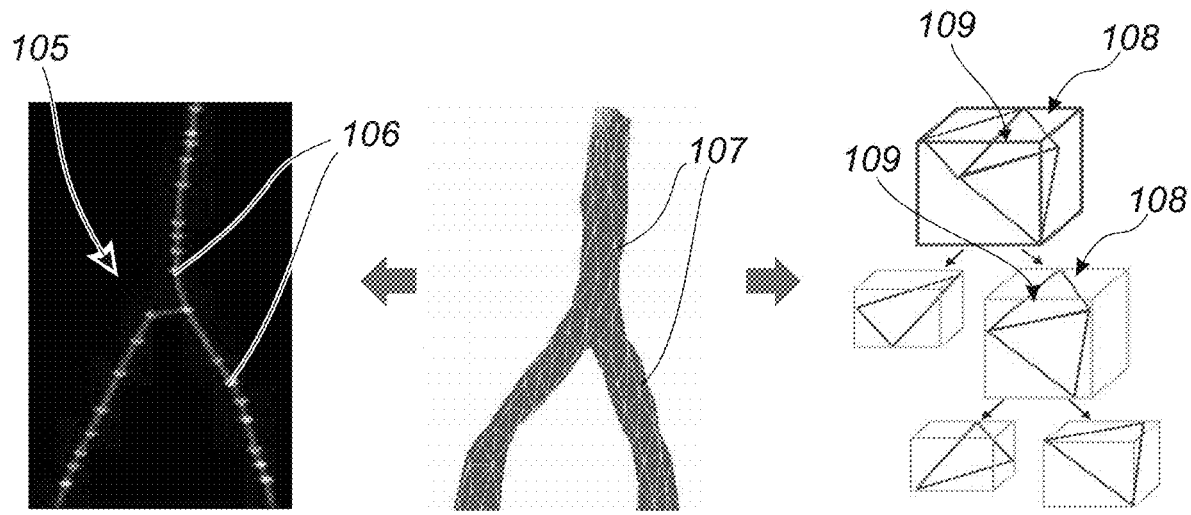
FIGS. 11A-C provide an illustration of structural indexing techniques applied to complex objects as vessel structures, in accordance with an embodiment of the disclosed system and method.

Skeleton based indexing as shown in FIG. 11A uses skeletons 110 of the vessel or other complex 3D object. The skeletons are effective shape abstractions used to capture the essential topology of the complex structures. Skeletons 105 of the blood vessels are extracted using for example, Mean Curvature Skeleton (MCS) algorithms. Each blood vessel is then represented by its skeleton vertices 106. FIG. 11A shows the extracted skeleton 105 for the vessel structure including respective mesh facets 107 as shown in FIG. 11B. The 3D dots shown in FIG. 11A are each of the skeleton vertices 106. The skeletons 105 capture the inherent 3D structure topology of the complex structure, and hence provide more meaningful nearest neighbor query results as compared to prior applications that implement single point simplifications.

Hence, the shortcomings of traditional approaches for distance based queries which simplify spatial objects with points or MBBs, are overcome by the disclosed system and method. The simplifications in prior systems are not effective in querying complex structured 3D objects, such as vessels. Moreover, the disclosed system and method provides two in-memory on-demand structural indexing techniques that accelerate and are effective for spatial queries on complex structures: topological skeleton based indexing, and hierarchical Axis-Aligned Bounding Box 108 (AABB) tree based indexing, as shown in FIG. 11C. In particular, shown in FIG. 11C is an illustration of AABB tree 108 on a subset of vessel facets 109. Skeleton based indexing is implemented in nearest neighbor querying, as discussed in greater detail hereinbelow with regard to FIGS. 16A-16C.

When implementing spatial proximity estimation queries, accurate distances between objects (e.g., cell and vessel) need to be computed. Rather than iterating on every primitive of a vessel structure, the disclosed system and method in accordance with an embodiment, builds a hierarchy on the AABB tree shown in FIG. 11C using its primitives (facets) 107 in order to minimize the traversal search space on the complex structured vessel shown in FIG. 11B. Test implementations indicate that with use of AABB tree indexing, the distance-based spatial queries are significantly accelerated.

Therefore, in accordance with an embodiment of the disclosed system and method, spatial proximity estimation is used for spatial queries, but necessitates precision in determining accurate distance calculation between objects. In particular, precise distances between each cell and its nearest complex structure, for example, a neighboring blood vessel, are required to be computed in order to estimate the spatial proximity of blood vessels. In addition, in order to minimize the search space of a complex structure object query or traversal, the disclosed system and method builds a hierarchy using the AABBs of its primitives (facets) of the complex structure, as shown in FIG. 11C. Using an AABB tree, an internal KD-tree can be optionally constructed to further accelerate the distance queries.

FIG. 11C is an illustration of an AABB tree on a subset of vessel facets. The tree is constructed using a bottom-up approach. The AABB tree component offers a static data structure and algorithms to perform efficient intersection and distance queries against sets of finite 3D geometric objects. The set of geometric objects stored in the data structure are queried for intersection detection, intersection computation and distance. The intersection queries can be of any type, provided that the corresponding intersection predicates and constructors are implemented in the traits class. The distance queries are limited to point queries. Examples of intersection queries include line objects (rays, lines, segments) against sets of triangles, or plane objects (planes, triangles) against sets of segments. An example of a distance query consists of finding the closest point from a point query to a set of triangles.

Note that this component is not always suited to the problem of finding all intersecting pairs of objects. Another component of intersecting sequences of multi-dimensional iso-oriented boxes may be used to find all intersecting pairs of iso-oriented boxes.

In other disclosed embodiments, the AABB tree data structure takes as input an iterator range of geometric data, which is then converted into primitives. From these primitives a hierarchy of axis-aligned bounding boxes (AABBs) is constructed and used to speed up intersection and distance queries. Each primitive gives access to both one input geometric object (so-called datum) and one reference id to this object. A typical example primitive wraps a 3D triangle as datum and a face handle of a polyhedral surface as the id. Each intersection query can return the intersection objects (e.g., 3D points or segments for ray queries) as well as the id (for example, the face handle) of the intersected primitives. Similarly, each distance query can return the closest point from the point query as well as the id of the closest primitive. In another example, the AABB primitive wraps a facet handle of a triangle polyhedral surface as id and the corresponding 3D triangle as geometric object. From a point query the squared distance is computed with the closest point determined, as well as the closest point and primitive id. The latter returns a pair composed of a point and a face handle.

Therefore, using two novel structural indexing approaches to accelerate distance based spatial queries: 1) topological skeleton based indexing (as shown in FIGS. 11A and 11B); and 2) hierarchical axis-aligned bounding box (AABB) tree based indexing, as shown in FIG. 11C, distance based queries of complex data structures can be accomplished effectively and with accelerated computational efficiencies not present in prior art systems.

Figure 11D:
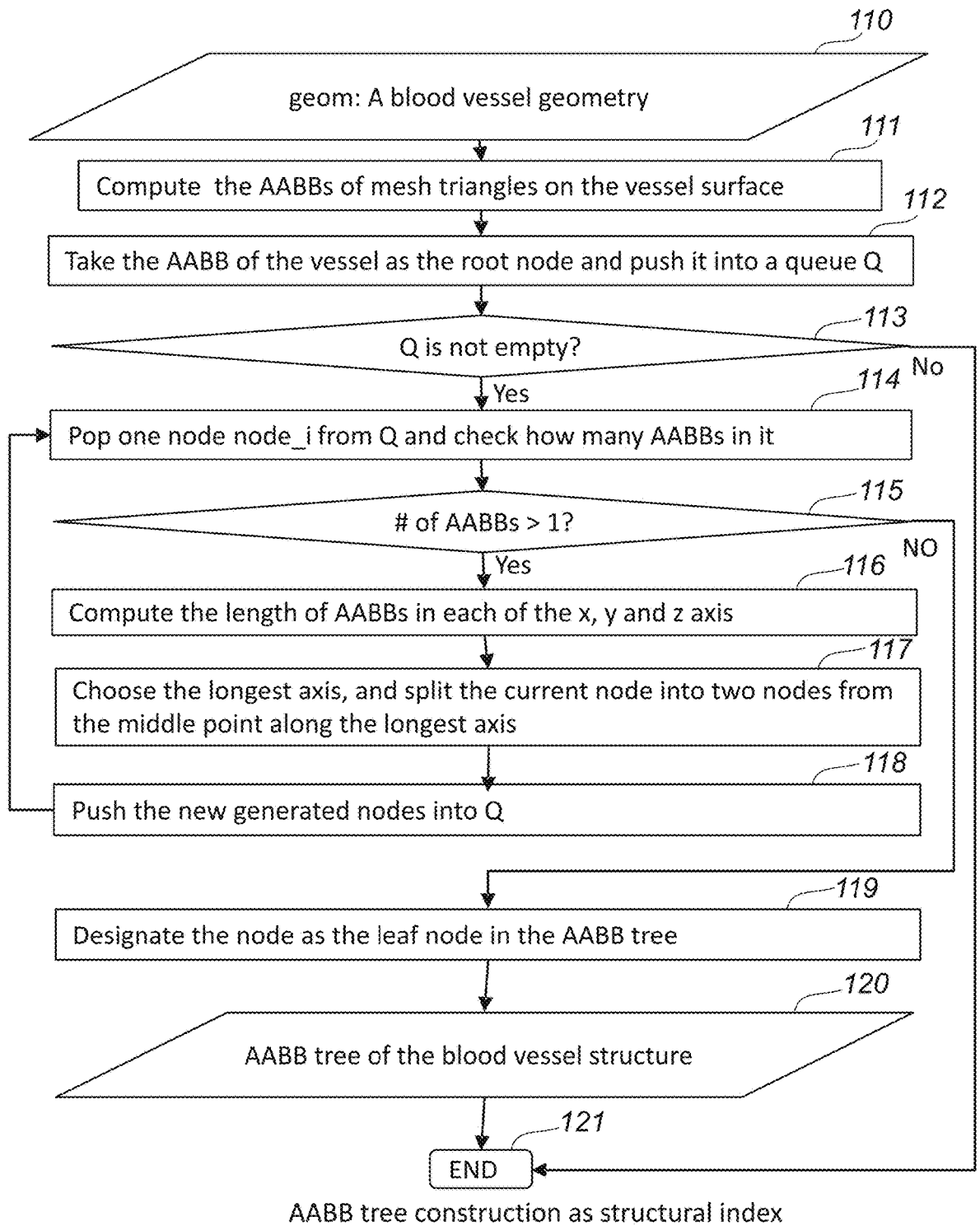
FIG. 11D illustrates a flowchart of an exemplary method of spatial proximity estimation using structural indexing techniques applied to complex objects as vessel structures as shown in FIGS. 11A-11C, and using the extracted inherent 3D structure topology of the complex structures to implement AABB based indexing technique to compute precise distance calculations between objects, in accordance with an embodiment of the disclosed system and method.

FIG. 11D illustrates a flowchart of the respective steps that are implemented in order to accomplish skeleton based indexing to capture and extract essential topologies of complex structures such as blood vessels. The skeleton vertices of the extracted skeleton of the vessel structure shown in FIGS. 11A and 11B, capture the inherent 3D structure topology, and be used to determine accurate distance calculations between the objects by implementation of AABB-tree based indexing, as illustrated in FIG. 11D. In accordance with an embodiment of the disclosed method, FIG. 11D illustrates a flowchart of application of the AABB tree on a subset of vessel facets as extracted from the vessel structure shown in FIG. 11B. Hence, spatial proximity estimation of neighboring complex 3D objects can be accomplished.

In order to construct the AABB tree, the AABBs of each of the mesh triangles that are extracted from the vessel structure as shown in FIG. 11B, are generated. Beginning with step 110 of FIG. 11D, respective blood vessel geometry is input into the system for processing. In particular, the mesh triangles 107, as shown in FIG. 11B comprise the blood vessel geometry, and are generated as input in step 110 for processing by the 3D query system. Next in step 111, the system computes the AABBs of each of the mesh triangles 107, as shown for example in FIG. 11C. Such mesh triangles 107 were previously extracted as described by a mesh of triangular geometry on the vessel surface, as shown in FIG. 11B, and AABBs 114 are then generated for each corresponding triangular mesh 107 on the vessel surface. The AABBs are generated as boxes 108 that surround each of the 3D triangles 109 of vessel as shown in FIG. 11C. Next, in step 112, the AABBs of the entire vessel is provided as the root node and pushed into a queue (Q). Proceeding to the next step 112, the system next uses the AABB of the vessel as the root node, and pushes it into a queue (Q). The system next determines if the queue (Q) is empty in step 113. If the queue (Q) is determined to be empty in step 113, the system proceeds to step 121, at which point the process ends at step 121. In step 113, as long as the queue is determined not to be empty, one node from the queue is popped in step 114, and a check is then performed to determine how many AABBs are in the particular node_i in step 114. Therefore, if the queue is not empty as determined in step 113, the system next pops one node from node_i from the queue (Q), and proceeds to check the number of AABBs that are contained in the node_i in step 114.

Figure 11E:
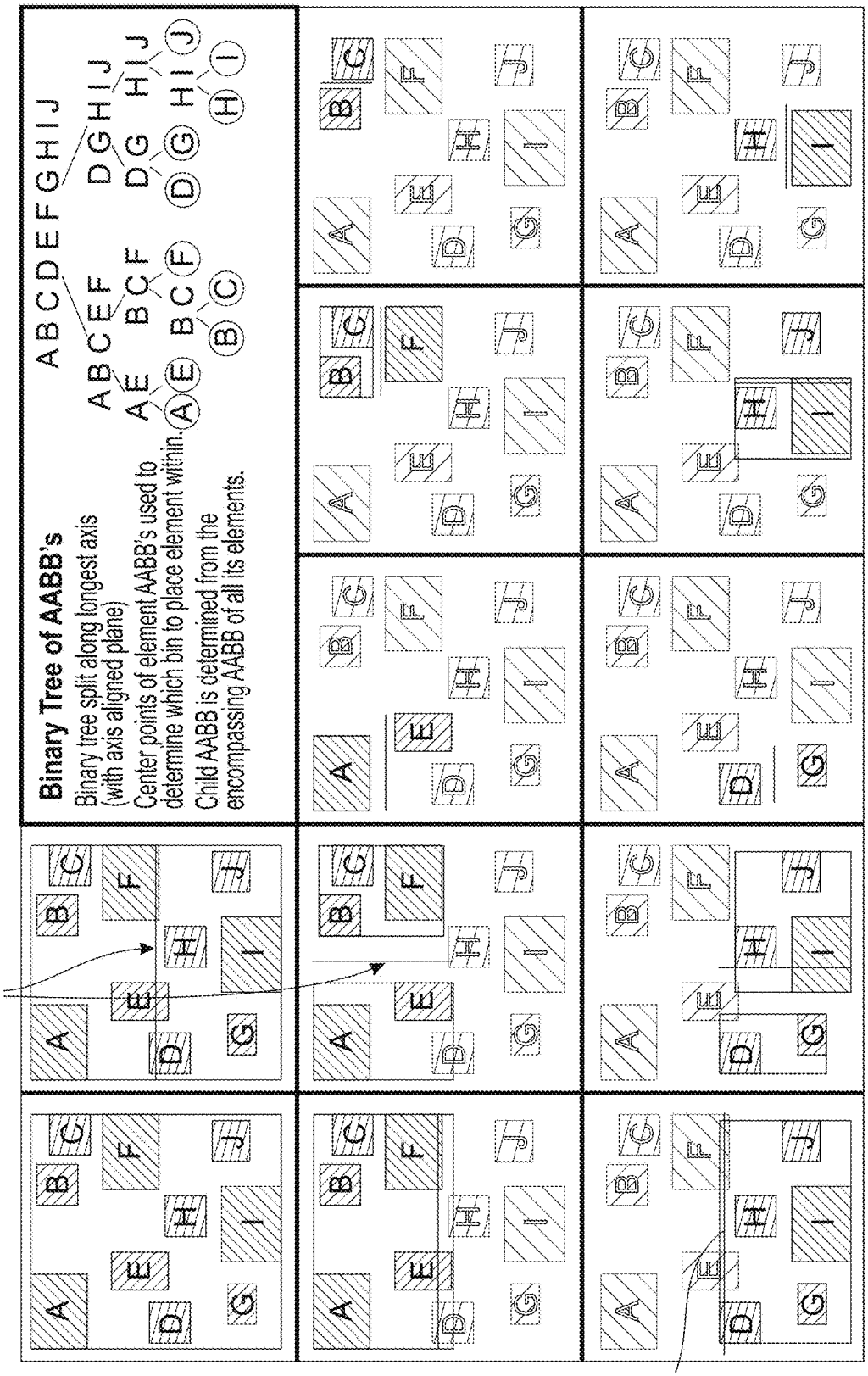
FIG. 11E is an illustration of the formations of binary tree of AABBs as applied to FIGS. 11A-D, in accordance with an embodiment of the disclosed system and method.

Next the system determines whether the number of AABBs is greater than 1, in step 115. If the node contains more than one AABB as determined in step 115, the system deems it as the internal node and performs a split along the longest axis into two child nodes (also as shown in FIG. 11E, axis line 122). Hence, the system next determines the length of AABBs in each of the x, y, z axis for the triangular geometry in step 116. If the number of AABBs are not greater than 1 as determined in step 115, the system will designate node_i as the leaf node of the AABB tree in step 119, and proceed to step 120, which is described further hereinbelow. If the number of AABBs are indeed greater than 1 as determined in step 115, the system next computes the length of the AABBs along each of the x, y, and z axis in step 116, hence, selecting the longest axis, and then splits the current node into two new generated nodes from the middle point along the longest path in step 117 (as also shown for example, in FIG. 11E, axis line 122). The system next proceeds to push the new generated nodes into the queue in step 118 for further checks. The system next proceeds back to step 114 to pop another node node_i from the queue, and performs an iterative check of how many AABBs are in the node in steps 115-118, performed iteratively. Once the number of AABBs are not greater than 1 in step 115, the system proceeds to the next step 119, in which the system designates the node as the leaf node in the AABB tree, in step 119. Therefore, if the node contains only one AABB, it is designated as the leaf node. After the system completes processing all the nodes stored in the queue, the AABB tree can be constructed. Hence, the output of the system is the AABB tree of the blood vessel structure as shown in step 120. The AABB tree construction is a structural index which is implemented in embodiments of the disclosed query system for analysis of the subject 3D complex structure being analyzed for topological, spatial and other characteristics and/or anomalies, by the disclosed query system.

Figure 11F:
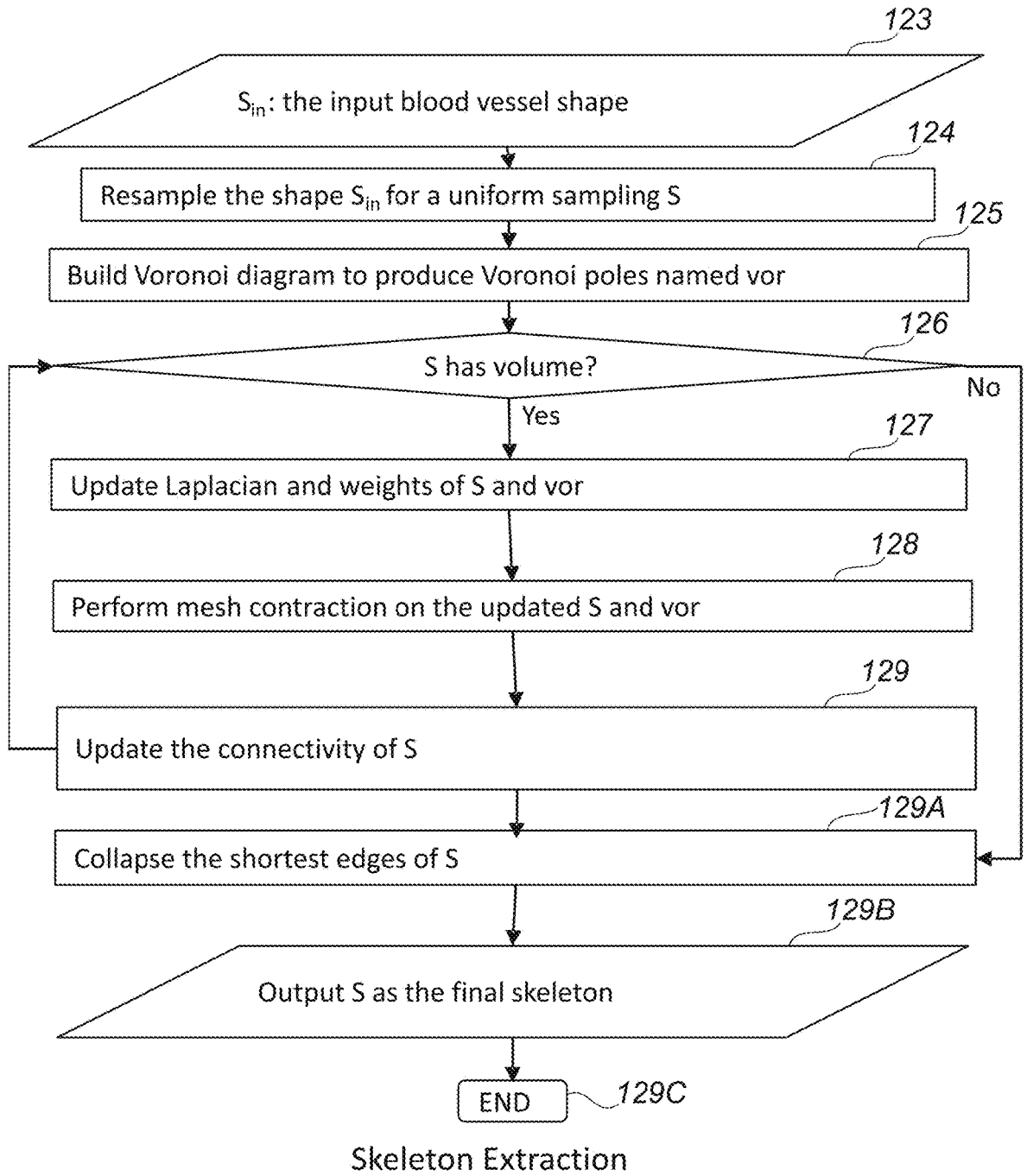
FIG. 11F is a flowchart illustrating the process of skeleton extraction associated with a complex 3D structure, in accordance with an embodiment of the disclosed system and method.

Referring to the structural indexing process as shown and described hereinabove with respect to FIGS. 11A-11C, further illustrated is an embodiment of the structural indexing process that includes extraction of the skeleton of the complex 3D structure (example, blood vessel) under analysis. Starting with step 123, in FIG. 11F, is an input of the blood vessel shape $S_{in}$ into the system. The system next resamples the shape $S_{in}$ for a uniform sampling S in step 124. Such surface sampling is performed so that the Voronoi poles lie on the respective media axis. In an example embodiment, in order to determine Voronoi poles, a plane is partitioned into regions based on distance to points in a specific subset of the plane. That set of points (called seeds, sites, or generators) is specified beforehand, and for each seed there is a corresponding region consisting of all points closer to that seed than to any other. These regions are called Voronoi cells. The Voronoi diagram is formed based on a set of points and is dual to its Delaunay triangulation. The positive and negative Voronoi poles of a cell in a Voronoi diagram are certain vertices of the diagram.

Hence, in step 125, a Voronoi diagram is created to generate and identify respective Voronoi poles, which are named, vor. Next in step 126, the system determines whether S still possesses volume. If so the Laplacian and weights of S and vor are updated in step 127. Then the system performs mesh contraction on the updated S and vor in step 128. As long as S still has volume as determined in step 126, the Laplacian and weights of S and vor are updated, and the mesh contraction in step 128 is performed, in order to reduce triangles on the mesh surface of the complex structure. If S does not possess volume in step 126, then the system advances to step 129A, in which it collapses the shortest edges of S. Otherwise, steps 127-129 are iteratively performed for updated S, the Laplacian and weights of S and vor are updated, and the mesh contraction of updated S and vor in step 128 is performed, in order to reduce triangles on the mesh surface of the complex structure. A new volume of S is then generated for further volume checking in step 126. An iterative process of steps 126-129 is performed until S no longer is determined to have any volume (i.e. volume=0 value) in step 126. At such point, the system proceeds to step 129A to collapse the shortest edges of S. The edge ends are designated as skeleton vertices (also as shown in FIG. 11A as dots, are the vertices 106. In step 129B, the system next outputs S as the final skeleton at which point the process ends in step 129C.

Essentially in order to extract the skeleton of the vessel structure, the system initially performs surface sampling 124 so that the Voronoi poles vor lie on the media axis 125. As long as shape S still has volume, the Laplacian and weights of S and vor are updated in steps 126 and 127. Then a mesh contraction is performed in step 128 to reduce triangles on the respective mesh surface. The connectivity of S is next updated in step 129 in order to generate a new S for volume checking. Once the volume of S is zero, the shortest edges of S are collapsed in step 129A, and the final skeleton is then identified in step 129B. The edge ends are then output and used as skeleton vertices in the respective embodiment of the query system. The above-described processes and/or methodologies associated with FIGS. 11D and 11F for the disclosed 3D query system and method, are contemplated to be performed in certain embodiments, by the computing system (300) described hereinbelow, and in greater detail with reference to FIG. 24.

Figure 12:
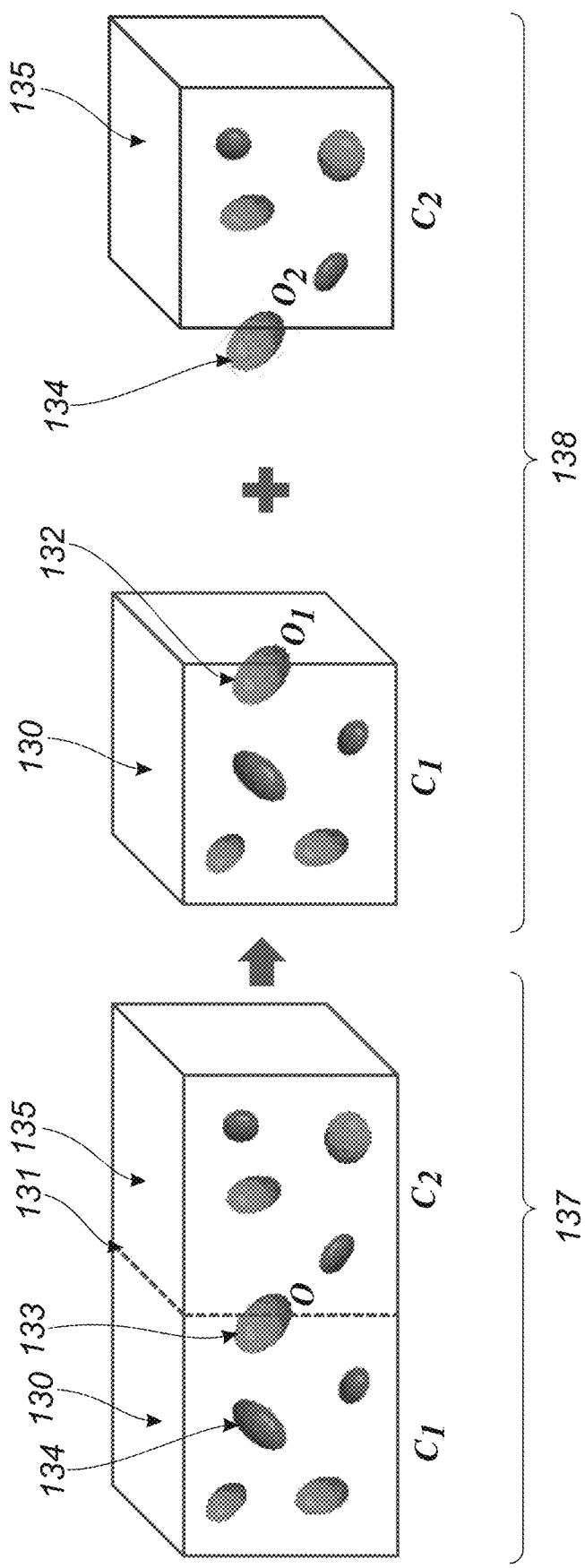
FIG. 12 is an illustration of boundary objects handling, in accordance with an embodiment of the disclosed system and method.

In accordance with another disclosed embodiment of the complex 3D spatial query system and method, is an implementation of analysis using boundary objects handling as shown for example, in FIG. 12. A partitioned cuboid is the basic parallelization unit for spatial queries. However, in cuboid based partitioning, some spatial objects may lie on cuboid boundaries and must be dealt with accordingly based on their position on one or more boundaries of the cuboid. Such objects are defined as boundary objects. In general, the fraction of boundary objects is inversely proportional to the size of the cuboid. As a respective cuboid size is decreased, the percentage of boundary objects increases (inversely proportioned with regard to the respective cuboid size). In accordance with an embodiment of the disclosed query system and method, two types of boundary objects are generally identified: 1) the normal boundary objects identified in spatial join query, as shown in FIG. 12; and 2) the buffered boundary objects determined using a distance based query method as shown for example, in FIG. 13A.

The normal boundary object is some spatial object of which its spatial extent crosses multiple cuboid boundaries, such as the nucleus O 133, as shown in FIG. 12. The cell O 133 crosses cuboid C1 130 and C2 135, and is therefore identified as a boundary object as it crosses both cuboids across a boundary line 131, as shown in FIG. 12. In practice, the normal boundary objects may impact the query results for example, in spatial join, and requires an appropriate level of analysis and correction to process such boundary objects.

In order to handle any issues stemming from such boundary objects, one approach is simply to discard it when only approximate query results are required. In such case, the results are interpreted statistically, and not affected by the tiny fraction of any such normal boundary objects. Whereas in many other practical applications, accurate and consistent query results are demanded since such boundary objects can lead to potential incorrect results when precision is mandated in the query. In such cases, normal boundary objects are remedied by a "multiple assignment, single join" approach as illustrated in FIG. 12. In order to return a complete query result, in accordance with a disclosed embodiment of the complex 3D spatial query system and method shown in FIG. 12, original cell or nucleus O 133, is duplicated as $O_1$ 132 and $O_2$ 134, and is next assigned to the two partitioned cuboids $C_1$ 130 and $C_2$ 135. Therefore, the system first duplicates the boundary objects 133 that intersect at partition line 131 (as shown in left portion 137 of FIG. 12). The system then assigns the duplicates to the multiple intersecting cuboids (130, 135) as shown in right portion 138 of FIG. 12. Then each cuboid is processed independently during query execution (with parallelization in certain embodiments). The query results are then generated with potential duplicates. The system next performs normalization on the query results by a filtering process such as elimination of any resulting duplicate records that are generated as a result of the boundary objects handling process.

Figure 13A:
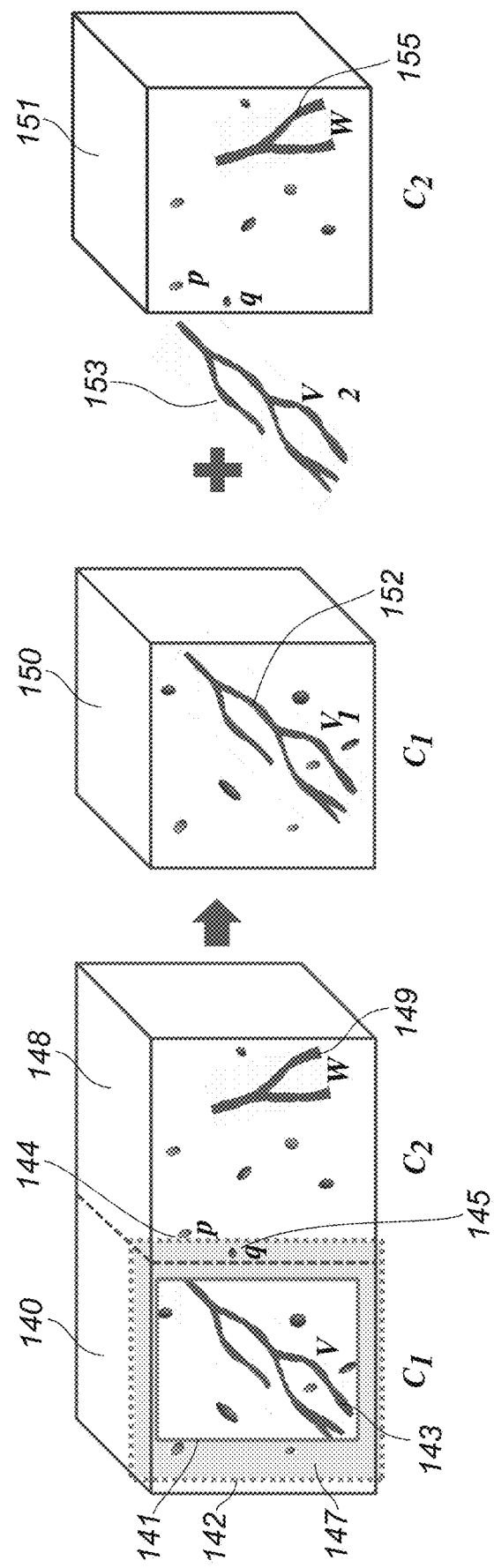
FIG. 13A is an illustration of buffered boundary objects process associated with complex 3D structures, in accordance with an embodiment of the disclosed system and method.

In accordance with an embodiment of the disclosed system and method, is a novel implementation of a system query of complex structures, using a buffered boundary object process that is associated with handling a query associated with boundary objects including a buffered boundary surrounding one or more complex structures. Buffered boundary objects are defined as an object that include one or more complex structures that also cross the cuboid boundaries when a buffer is added to the cuboid in which the complex structure resides and is bounded within by boundary lines 142, which creates a buffer 147. As shown in FIG. 13A, the complex 3D structure, the blood vessel V 143, is bounded by a buffer 147 as formed by dotted line 142 at each boundary line of buffer 147, that surrounds and encloses vessel V 143 about its own vessel V boundary lines 141. Buffered boundary objects are generated in distance based queries such as for example, nearest neighbor search or proximity estimation, in which accurate distance(s) would be required in order to generate more precise query results.

In particular, in the example embodiment shown in FIG. 13A, the nearest blood vessel (the example complex structure) for both nuclei p 144 and nuclei q 145, is blood vessel, V 143 (rather than farther vessel W 149 in C2 148). Blood vessel V 143 is contained within the boundary lines of cuboid $C_1$ 140. Although nuclei p 144 and nuclei q 145 do exist within the boundaries of same cuboid $C_2$ 148, the nearest blood vessel is determined by the system as blood vessel, V 143 rather than blood vessel, W 149. If a cuboid based query is performed without considering vessel V as a buffered boundary object, the query result would be erroneous. Therefore, each complex structured object (blood vessels in the shown example in FIG. 13) contained in two or more partitioned cuboids, a bounding box buffer is added to the MBB of the complex structured object, the blood vessel V. A light shaded buffer area 147 surrounding vessel V in cuboid $C_1$ 140, is generated as shown in FIG. 13. Next the system checks if the bounding box of buffer 147 crosses any other cuboids' boundaries. If the vessel V 143, which is now bound by bounding box of the buffer 147, becomes a boundary object with the added buffer 147 (i.e. now buffer surrounding vessel V 143 in FIG. 13 is on the boundary of $C_1$ and $C_2$), it is designated and treated as a normal boundary object, but the system also implements "multiple assignment" approach during query processing. During such "multiple assignment approach", vessel V 143 is duplicated as $V_1$ 152 and $V_2$ 153 across multiple cuboids $C_1$ and $C_2$ (150, 151) respectively, as shown in FIG. 13. Then the same process of distance based query processing is implemented as described hereinabove with respect to FIG. 12, as if there are no boundary objects.

The normalization step is not generally required for buffered boundary objects implementation, as there is no duplicate in the query results since each nucleus is uniquely identified as a 3D point within cuboids in distance based queries. For each complex structured object, the buffer size relies on the object size, and is set as the maximum MBBs of blood vessels in the example embodiment.

Figure 13B:
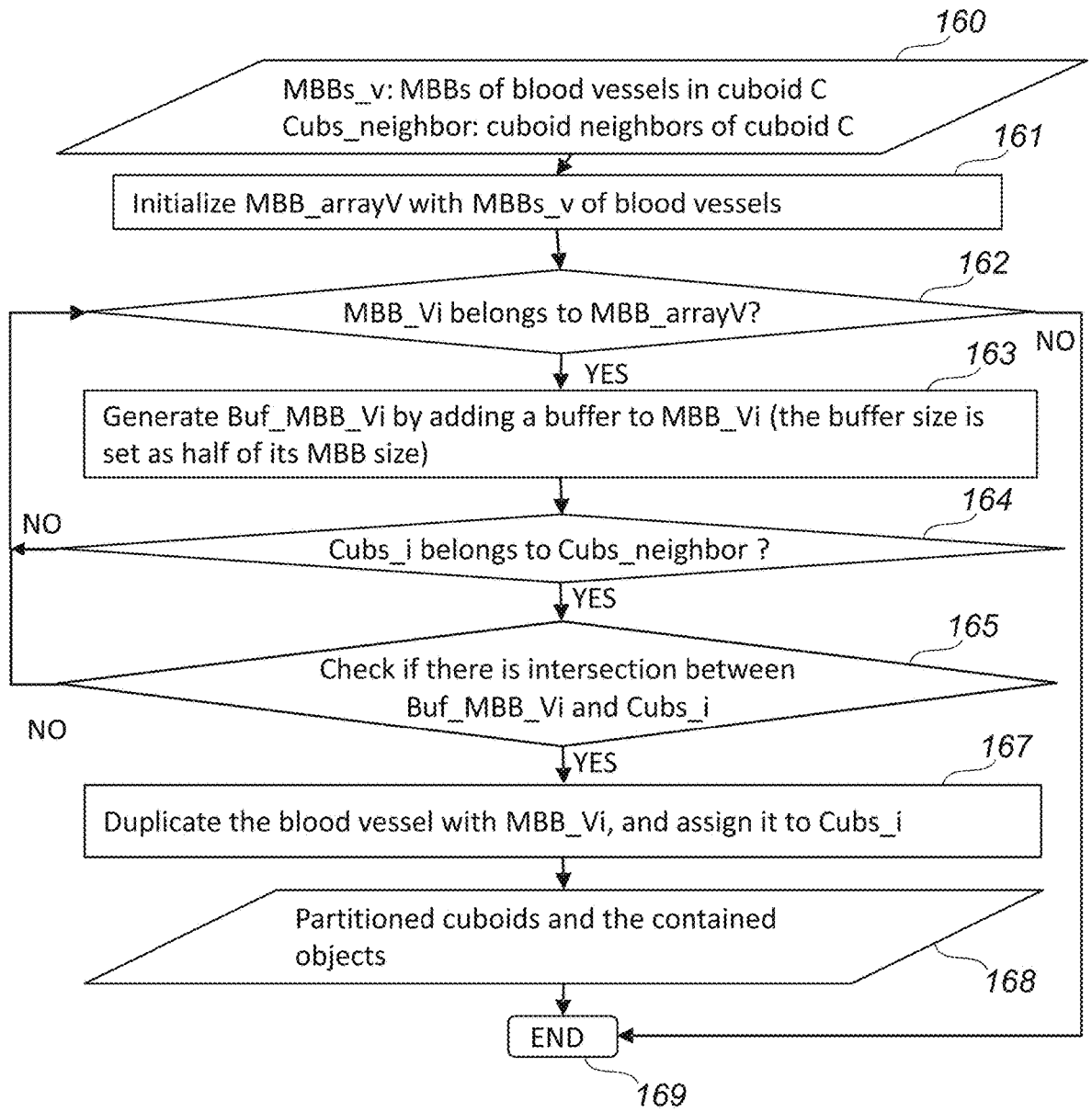
FIG. 13B is a flowchart illustrating the process of buffered boundary objects process associated with complex 3D structures, in accordance with an embodiment of the disclosed system and method.

Shown in FIG. 13B, is an example implementation of using buffered boundary objects query process, illustrated in a flowchart. Beginning with step 160, the example query system receives and processes an input of one or more MBBs (minimum bounding boxes) of any complex structures for example, blood vessels contained in cuboid C. Further received as input in step 160, and processed, is the value of Cubs_neighbor which is any of the cuboid neighbor(s) of cuboid C. The system proceeds to initialize an array, MBB_arrayV, with the values of MBBs_v for each of the respective blood vessels contained in cuboid C in step 161. Next in step 162, the system determines using an iterative process, whether MBB_Vi belongs to MBB_arrayV. If so, for the current (and later incremented value of Vi), the system next generates a buffer boundary Buf_MBB_Vi by adding a buffer to MBB_Vi in step 163 in order to generate buffer boundary Buf_MBB_Vi. The buffer size is set to half of its MBB size, in the example embodiment.

Proceeding to next step 164, a determination is made by the query system whether subject cuboid labeled Cubs_i belongs to neighboring cuboid, labeled as Cubs_neighbor. If the subject cuboid does not belong to a cuboid neighbor of cuboid C, then the system proceeds to step 162 to determine whether MBB_Vi belongs to MBB_arrayV, which checks whether the MBBs of the subject vessel Vi belong to the blood vessels contained within cuboid C. The system iteratively runs a check in steps 162-164 until the subject cuboid i is determined in step 164 to belong to cuboid neighbors of cuboid C (i.e., cubs_i). If so, the system next checks if there is an intersection between Buf_MBB_Vi and Cubs_i in step 165. This step determines if there is an intersection between the added buffered bounding box of subject vessel, and the cuboid in step 165. In this step 165, the system next determines if there is an intersection for subject MBB_Vi with neighboring cuboid, Cubs_i. If so, the system will next duplicate the blood vessels with the MBB_Vi and assign it to Cubs_i, in step 167. The partitioned cuboids and the contained objects are output in step 168. If there is no intersection between the buffer, buff MBB_Vi and the subject cuboid, Cubs_i, then the system will proceed back to step 162 and perform iteratively the steps of 162-164, until an intersection of the buffered boundary box of the subject vessel Vi (i.e. buff MCC_Vi) with subject neighboring cuboid i (i.e., Cubs_i), is determined in step 165.

In particular as shown in FIG. 13B, if the system indeed determines an intersection between buff_MBB_$v_i$ and Cubs_i in step 165, the system next duplicates the blood vessels with MBB_Vi, and assigns it to Cubs_i in step 167, and next outputs the partitioned cuboids and the contained objects in step 168. This process is further illustrated in FIG. 13A, in which blood vessel V is duplicated as $V_1$ and $V_2$. Cells (or nuclei)p and q (144, 145) remain in Cuboid $C_2$. $V_1$ remains in Cuboid C 150, and duplicate $V_2$ 153 is located proximate to or near but outside the boundary lines of Cuboid $C_2$ 151. This buffered boundary objects handling thereby permits a more accurate approximation of the distance between the subject vessel to its respective neighbor. This enhances pathological conclusions that can be derived from the quantitative results obtained from such analysis, specifically of the changes and relationships of cells structures to respective vessel structures and any respective changes over time. The above-described processes and/or methodologies associated with FIG. 13B for the disclosed 3D query system and method of buffered boundary objects handling, are contemplated to be performed in certain embodiments, by the computing system (300) described hereinbelow, and in greater detail with reference to FIG. 24.

Figure 14B:
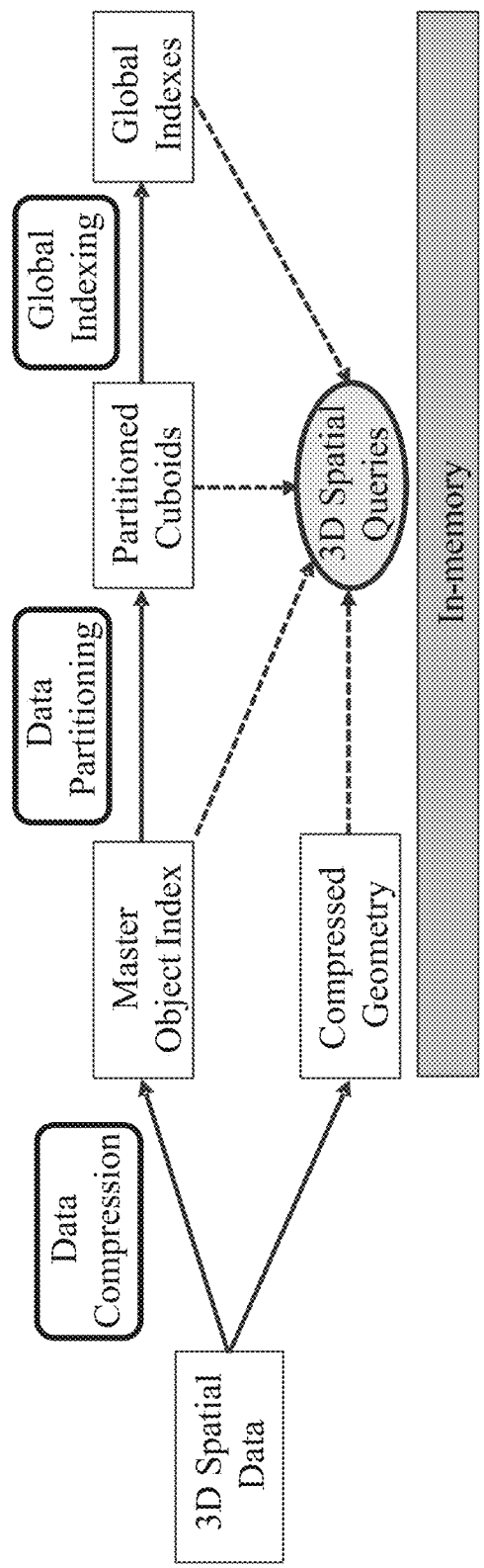
FIG. 14B provides an overview of the pre-processing step the 3D spatial query system implements as a one-time step of data processing of 3D spatial queries, in accordance with an embodiment of the disclosed system and method.

FIG. 14A provides an overview of the general framework of 3D spatial query data processing in accordance with a disclosed embodiment of the query system. The system commences with raw data staging. Data compression is accomplished via parallel processing and stored in-memory storage. The system performs spatial partitioning and indexing, which is also stored in-memory and provides for on-demand retrieval as needed by the query system. Next the system performs block based filtering using global indexes. For each cuboid in input-collection the system performs in parallel: 1) query task grouping based on cuboid indexes; 2) on-demand indexing for objects in the subject cuboid; and cuboid based spatial query processing as described for example in FIGS. 4, 6-7 and 14B. The next steps are boundary-crossing object handling; and respective storage of the query results.

In certain embodiments, the disclosed 3D spatial query system includes a core engine to support multiple types of spatial queries, including spatial join, spatial proximity estimation, nearest neighbor search, and others. The 3D spatial query system implements multi-level spatial indexes including subspace indexing, partitioned cuboid indexing, object-level indexing, and structural indexing. The disclosed system embodiment also handles boundary objects across partitions gracefully through multiple assignment approach. It retrieves and decompresses original 3D objects only when necessary and is highly memory efficient. The 3D spatial query system further provides query task parallelization using for example, MapReduce, and can be adapted to other distributed computing paradigms FIG. 14B provides an overview of the pre-processing step which in certain embodiments, the 3D spatial query system implements as a one-time step of data processing of 3D spatial queries. The dashed arrows in FIG. 14B represents the input for the spatial queries. The inputs to the 3D spatial query system include 3D spatial data which is compressed and/or indexed. The indexed 3D spatial data is stored in a master object index. In certain embodiments, the 3D spatial data is further partitioned into partitioned cuboids. Global indexing is further performed on the partitioned cuboids and global indexes are generated. The 3D spatial data in certain embodiments, is further processed by a computing device and generated as compressed geometry, which forms a part of the 3D spatial queries. The master object index, the compressed geometry, the partitioned cuboids, and global indexes, each forms part of the processed data for input into the 3D spatial query system. As shown in FIG. 14B, the 3D spatial query system is an in-memory based system in accordance with a disclosed embodiment.

The various components or modules that may be implemented by a system query processor, processing device, computing device or analogous structural devices and/or software modules can perform various operations. It is noted that the disclosed system and method can be implemented on cloud-based infrastructures and/or exchange information and communicate operations on known Internet protocols.

In a further embodiment, the disclosed system and method provides a one-time data pre-processing step for data compression, partitioning and global indexing. In such embodiment, original data is staged in a distributed file system such as for example, HDFS. Data compression is performed in parallel by a core engine of the 3D spatial query system. The original data is read from the distributed file system, compressed and combined in a binary format, and stored in a single memory segment that is replicated across all nodes. Thus, in the embodiment, the compressed data will be accessible by all processes in each node without the need of input/output (I/O) access. The compression can be implemented as a map only task for example, using MapReduce, for full parallelization, wherein each original 3D geometry object is in effect, a record for processing.

During compression, an embodiment of the disclosed system, extracts MBBs of each object, and creates a master object index which contains the MBB and memory location for the compressed object. Using a given unique ID of an object, the master object index expediently identifies the compressed data for retrieval and/or decompression. The 3D query spatial system, performs spatial partitioning using the master object index, which is based on the MBBs of the respective objects MBBs. A set of partitioned cuboids, is next generated, which become the processing unit for cuboid-based query tasks. Each partitioned cuboid is assigned with a unique "cuboid_id", and the partitioned cuboid index is created on the cuboid MBBs. Global subspace indexing is also created in certain embodiments, by grouping partitioned cuboids into large subspace(s) to support, for example, Windows® or other operating system-based query.

The on-demand in-memory based 3D spatial query engine implements multi-level indexing and data decompression for processing multiple types of spatial queries associated with complex 3D data structures. Compared to the pure disk based spatial query engine, it achieves superior results and better performance. The disclosed query system and method provides two types of structural indexing: skeleton based and hierarchical tree based, which significantly accelerate distance based queries as compared to the traditional MBB indexing. The spatial query system and method, provide a core spatial query engine to support multiple types of spatial queries, including spatial join, nearest neighbor search, and spatial proximity estimation. In addition the spatial queries can be easily extended to other types such as containment query.

The details of the various processes implemented by the 3D spatial query engine and the workflow in each spatial query pipeline are described in greater detail with respect to FIGS. 15A-17D, described further hereinbelow. Three 3D complex data spatial queries, specifically 3D spatial join, nearest neighbor and spatial proximity estimation, each will be discussed hereinbelow, as further example embodiments of the 3D spatial query system, as described with respect to FIGS. 15A-17D.

As further illustrated in FIG. 14B, the spatial query engine, in certain embodiments, provides a one-time data pre-processing step for data compression, spatial partitioning and global indexes creating. In such disclosed embodiment, data compression is performed in parallel. The original raw data is read from distributed file system such as for example, HDFS, compressed and combined into a single memory segment in binary format. The combined compressed data is replicated across all nodes, and cached in a shared memory segment (identified by a unique shared memory ID) on each node that is accessed by multiple processes with a pre-assigned shared memory ID.

The compression can be implemented as a Map specific only task in MapReduce for example, for improved efficiency. Each original 3D geometry object is used as a record for processing. The data compression process progressively generates successive levels of detail for each 3D object. Thus during spatial query processing, the 3D spatial query engine is able to dynamically decompress the 3D data at one or more specified level(s) of detail for the respective geometry computational extraction(s) (and related pathological or other real world applications).

As described hereinabove, during compression, the 3D spatial query system extracts MBBs of each object, and creates a master object index which contains the object ID, MBB coordinates, and the respective memory location for the compressed object. Using a given unique ID of an object, the master object index can expediently and more efficiently identify the compressed data for retrieval and decompression. Using the master object index, the 3D spatial query system performs more efficient and accurate spatial partitioning based on the object(s) respective MBBs, in order to generate a set of partitioned cuboids. The partitioned cuboids become essentially, the processing unit for cuboid based query tasks. Each partitioned cuboid is assigned a unique "cuboid_id", and the partitioned cuboid index is created based on the cuboid MBBs. Global subspace indexing is also created by grouping partitioned cuboids into large subspace(s) to support the system based 3D query.

Figure 15A:
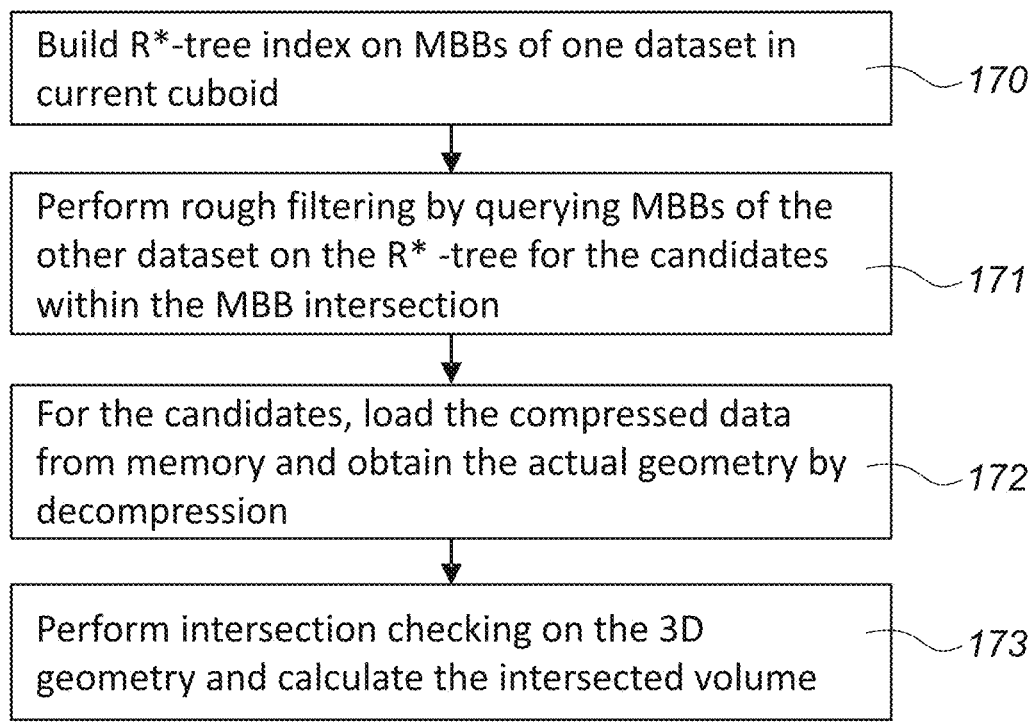
FIG. 15A is a flowchart illustrating the steps performed during 3D spatial join querying, in accordance with an embodiment of the disclosed system and method.

3D spatial join is a representative querying method implemented by the 3D spatial query system. FIG. 15A illustrates a flowchart that delineates the steps performed in accordance with an embodiment of the 3D spatial join querying method. In the first step 170, the system builds an R*-tree index on MBBS of one dataset in a subject cuboid. The system next performs in step 171, rough filtering by querying MBBs of the other dataset(s) on the R*-tree. The system uses only the candidates within the boundary lines of the MBB intersection in step 171. The system next loads the compressed data from memory and obtains the actual geometry by decompression in step 172. Finally, in step 173, the system performs intersection checking on the candidate 3D geometry and calculates the intersected volume, also as shown in FIG. 15B, darker shaded area 184.

3D spatial join is considered one of the more commonly used spatial queries, and various spatial join algorithms have been proposed in the past for various applications. In particular, in digital pathology use case, spatial queries are useful to find relationships of different types of biological objects such as containment relationships. Containment relationship is type of spatial relationship that exhibit features inside other features. Finding out whether a feature is inside or outside a boundary can be crucial to making decisions. One particular query type is spatial cross-matching, to compare or consolidate results of segmented and reconstructed 3D objects from different algorithms. The query identifies all intersecting polyhedron pairs between two 3D result sets from an image volume by use of different algorithms, thereby extracting intersecting volumes. Their overlap ratios (intersection-to-union ratios) are then computed.

Figure 15B:
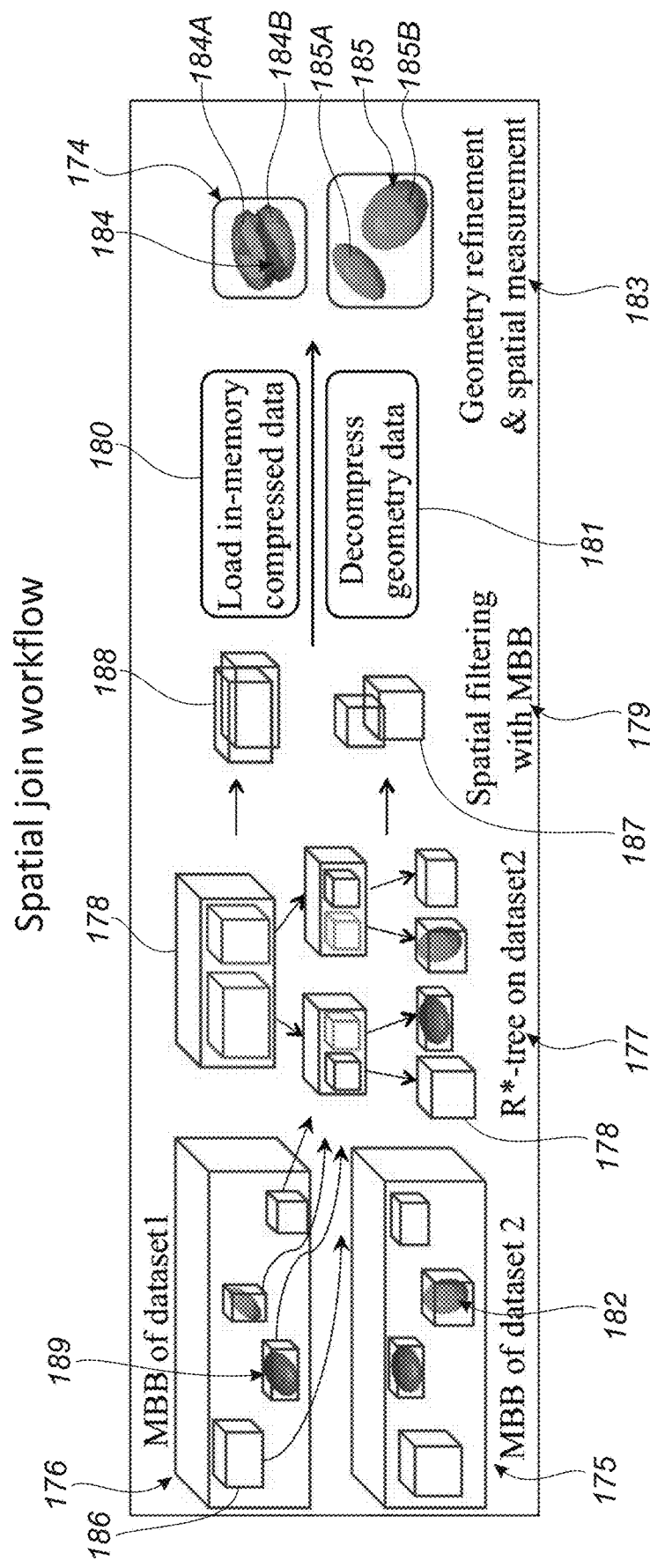
FIG. 15B illustrates the general workflow of an embodiment of the two-way 3D spatial join process, in accordance with an embodiment of the disclosed system and method.

Illustrated in FIG. 15B is the general workflow of an embodiment of the two-way 3D spatial join workflow. A filter-and-refine strategy is undertaken to reduce the computational costs and inefficiencies associated with spatial predicates on 3D geometries. After identifying the objects with the same "cuboid_id" from two datasets, the query system builds a spatial index in bulk on one dataset (for example, shown as dataset2 (175)) to generate an object-level index using a 3D R*-tree 177 for respective objects 189 of MBBs 186 of dataset1 (176). A Hilbert R-tree can also be used when the objects are in regular shapes and relatively homogenous distribution. The R*-tree index is built on object MBBs and is small enough in size, to be stored in memory. In order to perform spatial join query, for each given 3D object 189 in MBBs 186 dataset1 (176), a query is run on its respective MBB(s) 186 on the R*-tree 178. This is performed as a rough filtering step 177 (and next a spatial filtering step 179) in order to eliminate object pairs having no MBB intersection. For those candidate MBBs (187, 188) having MBB boundary intersection, the respective compressed data of those candidates are loaded from main memory 180, so that any candidates for geometry intersection can now be determined for the objects within the intersecting MBB candidates. Geometry decompression 181 of each respective geom1 (184A) and geom2 (184B) from dataset 1 and geom1 (185A) and geom2 (185B) from dataset 2, is next performed at specified level of detail to obtain their respective 3D geometry, for example, polyhedrons.

Next, the system performs a spatial refinement step 183 on the polyhedron pairs, for example, (geom1, geom2) (184A, 184B) and (geom1, geom2) (185A, 185B) through 3D geometric operations. Similar to predicate pushdown in traditional database query optimization, the spatial measurement step 183 is also performed on intersected polyhedron pairs in order to calculate and determine quantitative spatial results, such as intersecting volumes 184 and overlap ratios on respective geom pairs, geom1 (184A, 184B) and geom2 (185A, 185B) such that an intersecting volume between geom 1 and geom 2 pairs, for example volume 184A and 184B, is determined as volume 184, as shown in FIG. 15B. Intersecting volume between geom 1 and geom 2, for example, 185A and 185B, is also determined, and in the example embodiment is 0, since there is no intersecting volume as shown in geometry 185 bounding the geometry of objects, geom 1 and geom 2 (185A and 185B). Such spatial results are also required to be determined for the disclosed embodiment of the spatial join process. Other spatial operators such as overlaps and touches, can also be processed similarly. The detailed algorithm that is implemented during the spatial join process is illustrated in FIG. 15C.

Memory usage is more efficient in spatial join queries. As the workflow of FIG. 15B indicates, the filtering step works on object MBBs, and only the refinement step 183 is generally required to decompress the actual geometry into memory. The refinement step 183 is executed sequentially for a single task running on a single CPU core. One pair of geometries are retrieved from memory and decompressed in a specific time interval. Even with multiple parallel tasks on a single node, the disclosed 3D spatial query system, implements a small memory footprint during query processing. The memory usage is about 14 GB on each node in a typical cluster environment for spatial join queries operating on a dataset of 460 GB size.

Figure 15D:
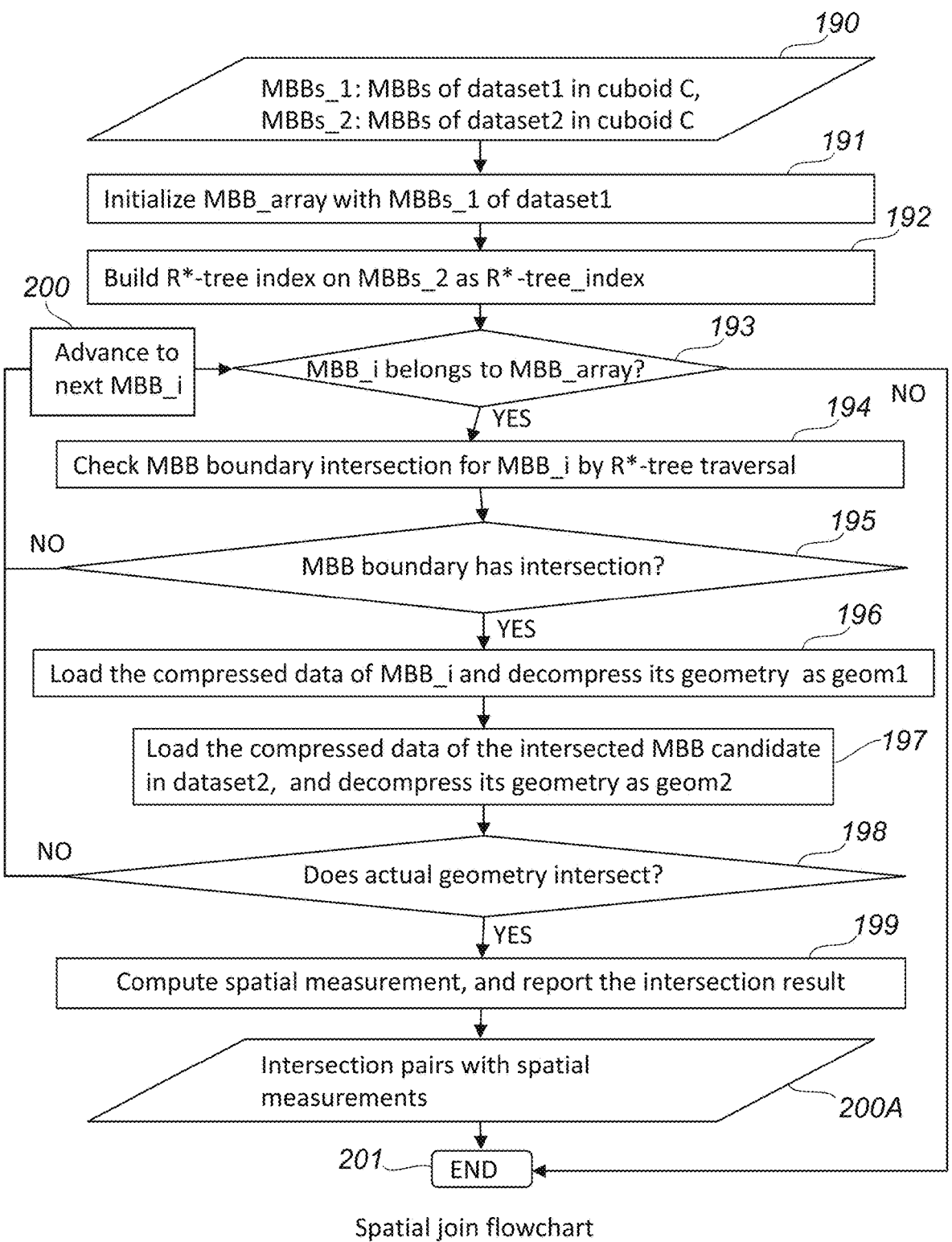
FIG. 15D is a flowchart illustration of an example spatial join query as shown in FIG. 15C, in accordance with an embodiment of the disclosed system and method.

FIG. 15C illustrates an example spatial join query algorithm. FIG. 15D is a flowchart illustration of an example spatial join query process.

In first step of the example spatial join query algorithm of FIG. 15D, the system receives as input and processes the minimum bounding boxes (MBBs) of dataset1 in cuboid C, shown in step 190. Also received as input and processed in step 190, are the MBBs of dataset2 in cuboid C. The algorithm can be implemented in n datasets. An example of the minimum bounding box of a cuboid that bound complex 3D objects, are received as system inputs, are the cuboid bounding boxes (175, 176) as shown in FIG. 15B. The MBBs and/or partitioned cuboids, are obtained from the data compression set, that were generated by a data compression module, located and retrieved from the master object index or the global index, as illustrated in the pre-processing flow in FIG. 14B. The example process proceeds to next step 191 in which the system generates an array formed by MBBs_1 from dataset 1, thereby initializing MBB_array of dataset1. The system next builds an R*-tree index on the MBBs_2 of dataset2 as an R*-tree_index in step 192 (also as shown in FIG. 15B, elements 175,177). Essentially it is determined if any of the objects have the same cuboid_ids from the two datasets to check for intersecting objects. The MBBs or cuboid_ids must intersect first, in order to determine if their respective objects (that they bound) also intersect. The system builds a spatial index in bulk on one data set, for example dataset2 in order to generate an object-level index using for example a 3D R*-tree or Hilbert R-tree (when objects are regular shapes and relatively homogenous distribution). The R*-tree_index is generated by the system based on object MBBs and is small enough in size to be stored in memory for later on-demand retrievals.

Objects contained in of dataset 1, within respective MBBs, are used to perform R*tree traversals on dataset 2 (177). This essentially accomplishes a check of any intersection of objects from dataset1 and dataset 2. At step 193, the system determines whether MBB_i belongs to MBB_array. If so, the system checks the MBB boundary intersection of MBB_i using R*-tree traversal in step 194. The MBB_dataset 1 determines if MBB intersected with any objects of dataset2 175. The system accomplishes this step 194 by using R*-tree traversal on dataset2. Otherwise, if the system determines that MBB_i does not belong to MBB_array in step 193, the system proceeds to step 201 and ends the process since no MBBs intersect, and hence, the system can necessarily conclude or deduce, that none of the inner objects residing in the respective MBBs intersect too.

Following step 194, the system next determines if an MBB boundary has an intersection in step 195. If so, the system loads the compressed data of MBB_i and decompresses its geometry as geom1 in step 196. The system next loads the compressed data of the intersected MBB candidate in dataset2 and decompresses its geometry as geom2 in step 197. This step 195 of determining geometry boundary intersections, essentially is the step shown in FIG. 15B, of spatial filtering of MBBs 179. In order to perform spatial join query, for each 3D object in dataset1, each of its MBBs on the R*-tree are queried as a filtering step as shown in 179, FIG. 15B, in order to eliminate object pairs having no intersections. However, for any candidates exhibiting MBB intersection, the system does load respective compressed data from main memory to generate its respective geometry (geom1, geom 2) by performing geometry decompression at a specified level of detail to obtain for example, geometry as polyhedrons as delineated in step 196. Essentially, the system in step 196 loads the compressed data of each MBB_i, the boundary intersection MBB_i, and decompresses its geometry as geom1. The system next loads the compressed data of respective intersected MBB candidate(s) in dataset 2, and decompresses its geometry as geom2 in step 197. Then the system next determines if the actual geometry of the respective datasets 1 and 2 intersects, for example, if geom1 intersects with geom2, from each dataset, by using 3D geometric computations in step 198.

If the MBB boundary has no intersection as determined in step 195, the system advances to analysis of next MBB_i, by advancing i with i=i+1 in step 200, and iteratively, performing the same operations of steps 193 to 195. Otherwise, in step 198, if the system determines that the actual geometry of the datasets1 and 2 (geom1 and geom 2) (for example, polyhedrons) intersects, the system proceeds to compute spatial measurements and report the intersection result in step 199. The intersection pairs with spatial measurements including the volume 184 of the intersecting region formed by the intersecting pairs of objects, are output in step 200A. The system essentially performs spatial refinement step as shown in FIG. 15B, on the respective 3D geometry such as for example polyhedron pairs (184A, 184B) and polyhedron pairs (185A, 185B) bounded by boundary geometry (174, 185) as associated with spatial join process performed on dataset1 and dataset2. Such spatial refinement step on the polyhedron pairs are performed using various 3D geometric operations. Similar to predicate pushdown in traditional database query optimizations, the spatial measurement step is also performed on intersected polyhedron pairs to calculate quantitative spatial results required, such as intersection volumes and overlap ratios. An example algorithm implemented to calculate such quantitative spatial results is shown in FIG. 15C. Such quantitative results can be implemented by using the Jaccard coefficient algorithm as described hereinbelow in equation (5).

The system ends the spatial join process at step 201. Such 3D spatial join process essentially identifies all intersecting polyhedron pairs between the two 3D result sets from an image volume and extract such intersecting volume(s) of respective polyhedron pairs, specifically shown as darker intersecting volume 184 of polyhedron 174, as shown in FIG. 15B. For a given single task running on a single CPU core engine, the refinement step can be executed sequentially and one pair of geometries are retrieved from memory and decompressed at a time. Even with multiple parallel tasks, the disclosed 3D spatial query system implements a small memory footprint during query processing. Memory usage is efficient using spatial join queries as the filtering step 179 works on object MBBs, and decompression of geometry needs to occur only at the refinement step 183 and loaded into memory. The above-described processes and/or methodologies associated with spatial join process as described in FIGS. 15A-15D for the disclosed 3D query system and method, are contemplated to be performed in certain embodiments, by the computing system (300) described hereinbelow, and in greater detail with reference to FIG. 24.

Figure 16A:
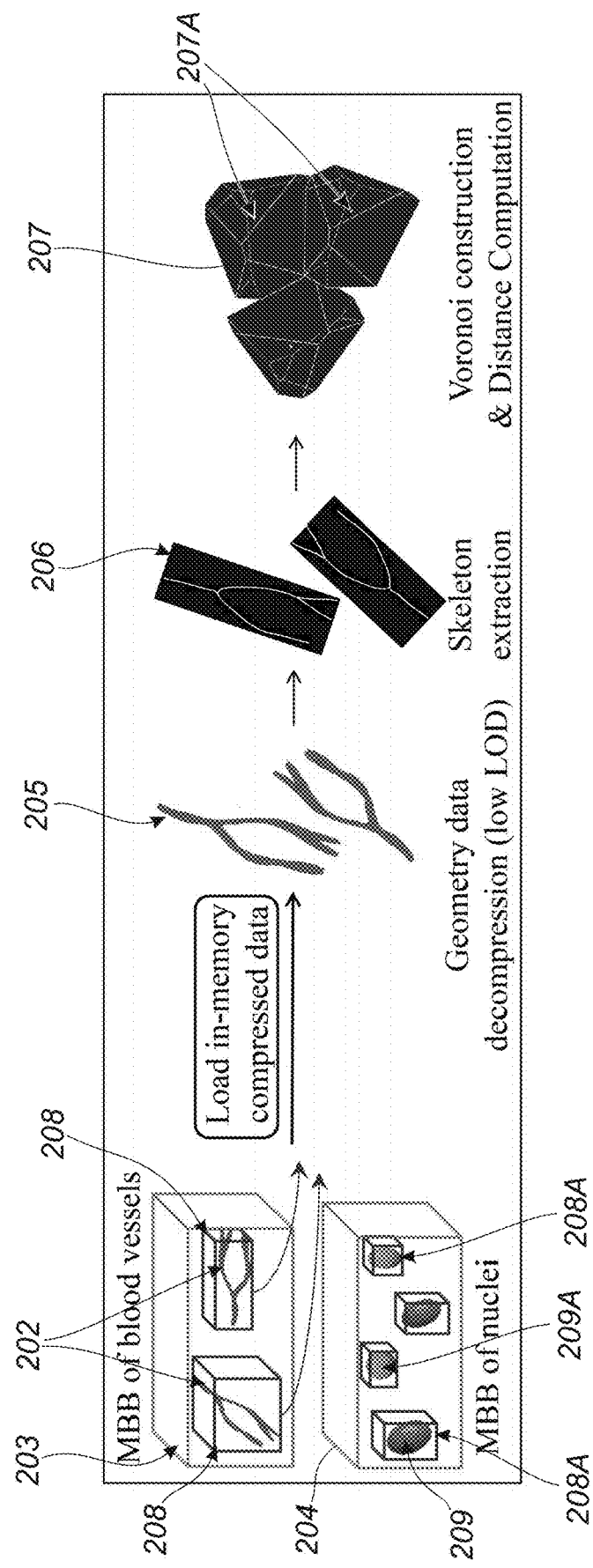
FIG. 16A illustrates the workflow of an example Voronoi-based 3D nearest neighbor (NN) spatial query analysis, in accordance with an embodiment of the disclosed system and method.

Another embodiment of spatial queries associated with analysis of complex 3D structures is the 3D Nearest Neighbor (NN) Query, as illustrated in FIG. 16A. Nearest Neighbor (NN) spatial query has broad applications in various domains. In 3D analytical pathology imaging, pathologists are interested in spatial queries such as for example, "for each 3D cell, return its nearest 3D blood vessel and the distance". These queries are essential for researchers and clinicians to better understand the correlations between spatial patterns and cell characteristics, and can be answered by Nearest Neighbor search algorithms.

Traditional spatial database systems may implement different nearest neighbor (NN) query approaches, but most of them are limited since they primarily deal with limited point data. These known methods may simplify the problems of managing and querying spatial data associated with complex structures and is applicable for certain queries where approximate results, rather than more precise results, are permissible. However, this type of simple point approximation approach is not suitable for nearest neighbor NN type queries implemented in 3D pathology, in which practitioners and/or researchers are more interested in 3D objects with complex structures such as 3D blood vessels that exhibit aberrant topological and other features that requires greater precision in query spatial analysis. In practice, 3D blood vessels with bifurcations and branches are reconstructed to better characterize their spatial properties. Thus using a simple point approximation of the 3D blood vessel structure results in critical loss of 3D spatial and structural information, and may produce erroneous results when implementing such nearest neighbor (NN) query. In order to more precisely characterize the structure of blood vessels, skeleton based structural indexing is implemented for each blood vessel structure as illustrated in FIGS. 11A-11C.

In order to support efficient spatial Nearest Neighbor NN querying, a large suit of algorithms for spatial access methods have been developed. An example embodiment implements, the Voronoi diagram approach which has been studied for nearest neighbor queries in various research domains. In such embodiment, given a set of input sites, typically 3D points in space for a particular 3D case, a Voronoi diagram is generated that partitions the space into disjoint polyhedrons based on distance to the query sites. Each given site has a corresponding polyhedron consisting of all 3D points closer to that site than to any other. In the example embodiment, we assume that $S=\{s_i\}_{i=1}^n$ is a set of given n sites. Its respective 3D Voronoi diagram is represented as: $V=\{V_i\}_{i=1}^n$ consisting of n polyhedron cells V formulated as indicated in Equation (1):

Equation (1) is reproduced hereinbelow as:

$$V_i = \{p \in \mathbb{R}^3, \|p-p_i\| \leq \|p-p_j\|, \forall j \neq i\}$$

Further illustrated in FIG. 16A, is the workflow of an example of Voronoi-based 3D nearest neighbor (NN) spatial query analysis, in accordance with an embodiment of the disclosed system and method. The system retrieves for each 3D blood vessel 202 contained within the MBB 208 within partitioned cuboid C 203, the respective compressed data and loads it in-memory. The respective geometry data (for example, the object such as vessel or nuclei) is decompressed as shown in 205 as geometry data with low LOD, and stored into memory for skeleton extraction 206 in accordance with the structural indexing process as shown for example in FIGS. 11A and 11F. Each vessel 202 is then represented with its skeleton vertices 106, as shown for example in FIG. 11A, and FIG. 16A, step 206 once the skeleton extraction indexing process occurs. Next all skeleton vertices of vessels 206 are collected by the system, and used as input sites to construct the Voronoi diagram. The system implements the constructed 3D Voronoi diagram to perform Nearest Neighbor (NN) search for every nucleus 209 contained within MBBs 208A within the same partitioned cuboid 204. Each 3D nucleus (209, 209A) is simplified as a 3D point, since it is relatively small in size as compared to a vessel structure 202. The system using the Nearest Neighbor (NN) query determines and outputs the nearest blood vessel for each nucleus as well as the distance. An example algorithm shown as Algorithm 4 illustrating an embodiment of nearest neighbor algorithmic steps, is listed in FIG. 16B.

Note that since the skeleton extraction algorithm used in Nearest Neighbor NN query, mainly relies on the shape and topology of 3D objects, rather than the mesh details, it is not necessary to specify in certain embodiments the highest LOD during geometry compression. Thus, the LOD may be set to 60% in certain embodiments, in order to improve the efficiency of geometry decompression and skeleton extraction for NN query acceleration. Since skeleton extraction generally requires geometry with lower LODs, and one Voronoi diagram is constructed for one respective partitioned cuboid, the usage of memory in NN query is considered small and insignificant.

Figure 16C:
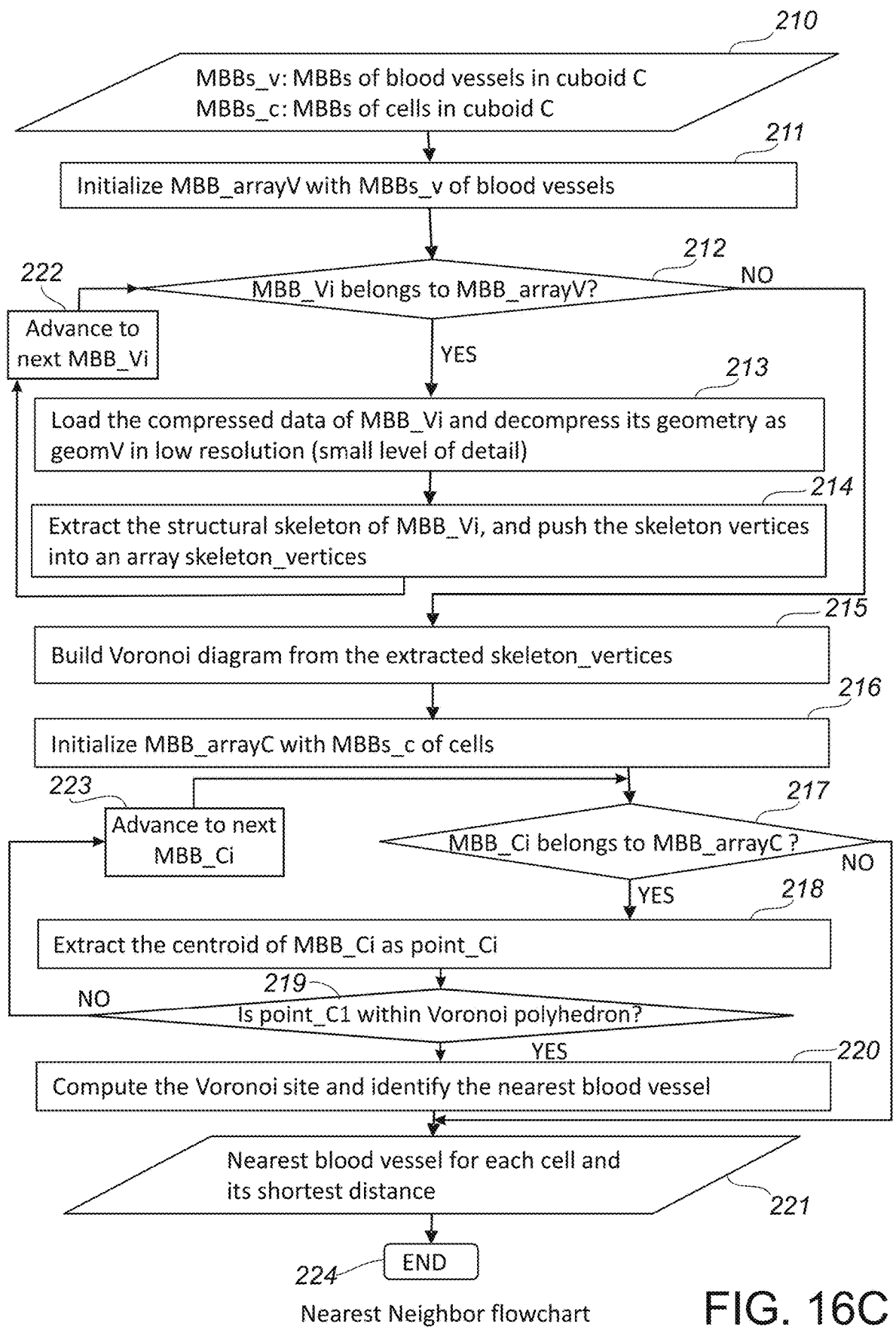
FIG. 16C is a flowchart illustration of an example nearest neighbor (NN) query as shown in FIG. 16A, in accordance with an embodiment of the disclosed system and method.

FIG. 16C is a flowchart illustration of an example nearest neighbor (NN) query as shown in FIG. 16A, in accordance with an embodiment of the disclosed system and method.

Beginning with step 210, the system receives as inputs MBBs of blood vessels contained within boundary of subject partitioned cuboid C (MBBs_v) and the MBBs of cells contained within the boundaries of cuboid C (MBBs_c). Since there may be multiple vessels within partitioned cuboid C, the system generates and uses an array to iteratively process each MMB for each vessel within cuboid C. Therefore, the system next initializes and generates an array, MBB_array based on the MBB for subject vessel, MBBs_v in step 211. Step 211 accomplishes forming an array for each minimum bounding box of each respective blood vessel(s) contained within the boundary of cuboid C, so that a determination can be made of the nearest blood vessel for every nucleus and/or cell as well as the actual distance between the blood vessel and respective nucleus or cell.

Proceeding to step 212, the system next determines whether MBB_Vi belongs to MBB_arrayV. This permits checking iteratively of whether the MBB_Vi belongs to MBB_arrayV in step 212 and performs steps 213-214 iteratively for each MBB_Vi as Vi advances to Vi=Vi+1 in step 222. Essentially this step 212 determines whether the MBB contains within its boundaries, a blood vessel from partitioned cuboid C. If it does, the system proceeds to load the compressed data of MBB_Vi and decompresses its geometry as geomV in low resolution (small level of detail) as shown in step 213. Therefore for each 3D blood vessel with the partitioned cuboid C, its respective compressive data is retrieved and further decompresses into its 3D geometry into memory for skeleton extraction. Next the system proceeds to step 214 to extract the structural skeleton of MBB_Vi, and pushes the skeleton vertices into an array skeleton_vertices. Each skeleton vertex is assigned its respective blood vessel ID. The system next proceeds to advance to the next MBB_Vi in step 222 with Vi=Vi+1, and iteratively checking the next MBB_Vi in step 212. If it is determined that MBB_Vi does not belong to the MBB_arrayV, the system next proceeds to build a Voronoi diagram from the extracted skeleton_vertices in step 215, based on the array of skeleton_vertices generated in step 214. All skeleton_vertices of the blood vessels are identified as inputs to construct the Voronoi diagram. The skeleton_vertices are generally (x, y, z) inputs. Example skeletal vertices are shown in FIG. 11A, element 106. The vertices are used as input to construct respective polyhedrons for each vessel within partitioned cuboid C. Using the 3D Voronoi diagram, the system performs NN searching for every nucleus within the same partitioned cuboid. Each 3D nucleus is simplified as a 3D point since considered small in size relative to the vessel structure.

Thus, in step 216, the system next initializes MBB_arrayC with MBBs_c of cells (or alternatively nuclei). The system iteratively checks whether the subject cell belongs to the array MBB_arrayC. If the cell does not belong to the array of the cuboid C, the process proceeds to advance to next MBB_Ci, by advancing counter Ci=Ci+1 in step 223. If the next MBB_Ci does not belong to MBB_arrayC the method ends in step 224. If the next MBB_Ci indeed belongs to the array in step 217, then the system extracts the centroid of MBB_Ci as point_Ci in step 218. The system in step 219 next determines if point_Ci, the extracted centroid of MBB_Ci (as generated in step 218) is within or intersects respective Voronoi polyhedron generated in step 215. If not, it proceeds to advance to next MBB_Ci in step 223 and iteratively checks if MBB_Ci belongs to MBB_arrayC in step 217 (and perform steps 218-220, iteratively for next MBB_Ci). Otherwise, if point_Ci indeed intersects and is within the boundary of respective Voronoi polyhedron in step 219, the system next proceeds to compute the Voronoi site for the intersecting centroid point_Ci, and identifies the nearest blood vessel, as shown in step 220. In steps 219-220, the system essentially determines which Voronoi polyhedron (as shown for example, in FIG. 16A, 207) contains the cell centroid point_C (as shown for example, in FIG. 16A, 207A). The corresponding Voronoi site (the skeleton vertex) that intersects the Voronoi polyhedron, is then determined as the nearest site, and the blood vessel with the same blood vessel ID is determined as the nearest blood vessel. The shortest distance is computed as the distance between cell centroid point_C and its Voronoi site (the nearest skeleton vertex). The output of the system is the determined nearest blood vessels to each cell and the respective, shortest computed distance in step 221, once all respective MBB_ci are processed that belong within MBB_arrayC in step 217, (and iteratively steps 218-220, described hereinabove). Hence, the nearest neighbor query process ends at step 224.

Spatial proximity estimation is another embodiment of the disclosed 3D spatial query system and method, that explores the distribution of target objects in 3D space given a set of basic objects. In 3D digital pathology, for instance, the spatial distribution of different types of vessels in liver organ is useful in providing a quantitative measurement of disease progression. 3D proximity estimation is a complex spatial query involving multiple objects. It is based on nearest neighbor search and demands accurate distance computation for global spatial pattern discovery. The above-described processes and/or methodologies associated with FIG. 16C for the disclosed 3D query system and method, are contemplated to be performed in certain embodiments, by the computing system (300) described hereinbelow, and in greater detail with reference to FIG. 24.

Figure 17A:
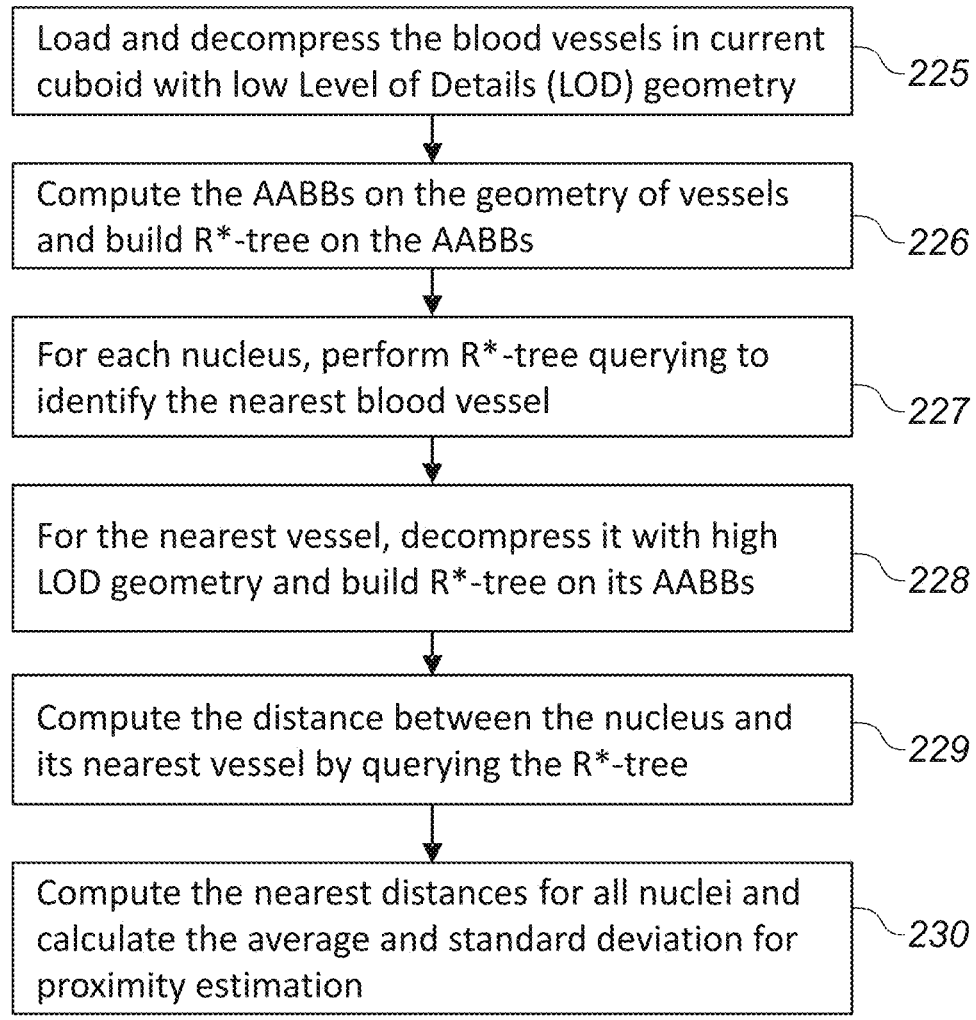
FIG. 17A is a flowchart illustration of spatial proximity estimation query in accordance with an embodiment of the disclosed system and method.

Shown in FIG. 17A is a workflow diagram providing an overview of the operations implemented in an example spatial query, implementing spatial proximity estimation. In the first step 225, the system loads and decompresses the blood vessels in current cuboid with low level of details (LOD) geometry. The system then computes the AABBs on the geometry of blood vessel structures and builds an R*-tree on the AABB in step 226. A process of R*-tree querying is next performed for each nucleus to identify the nearest blood vessel in step 227. For the nearest vessel as determined in step 227, the system next decompresses the blood vessel with high LOD geometry and builds R*-tree on its AABB in step 228. Next the system computes the distance between the nucleus and its nearest vessel by querying the R*-tree in step 229. Finally, the nearest distances for all respective nuclei are computed by the system. The system calculates for example, the average and standard deviation for proximity estimation in step 230.

Figure 17B:
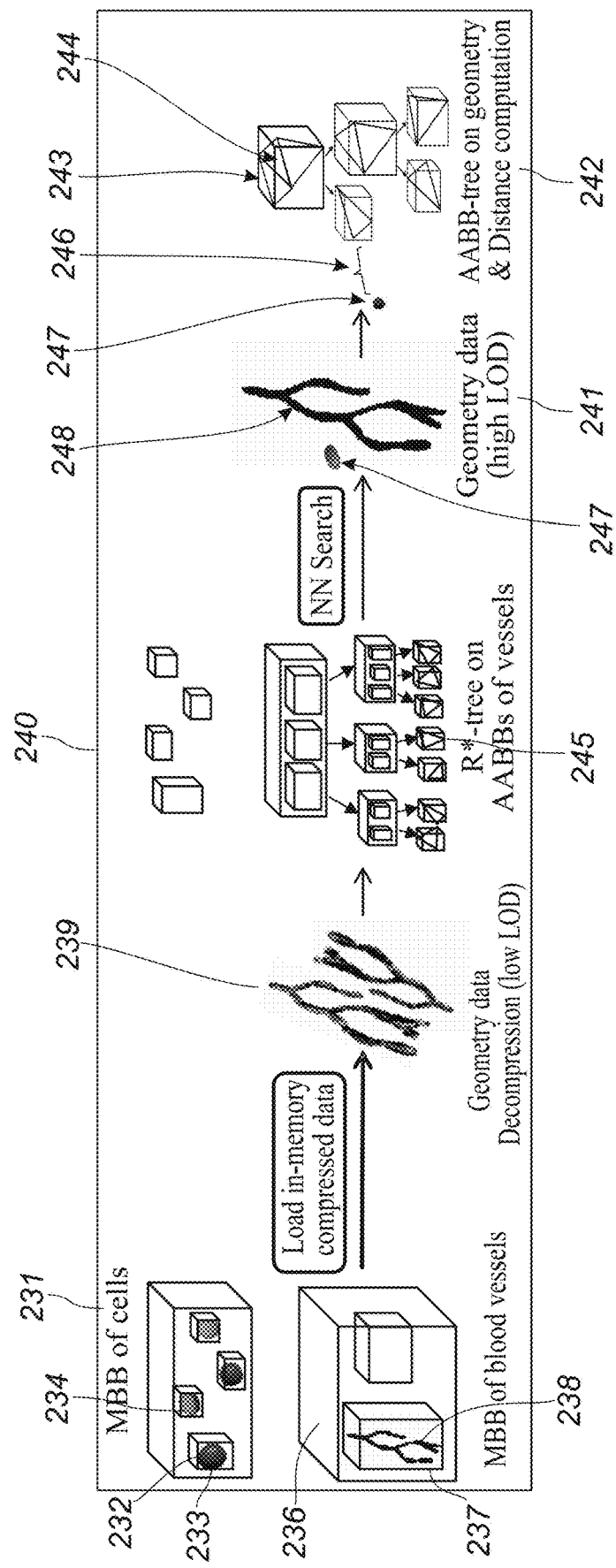
FIG. 17B illustrates the workflow of spatial proximity estimation query in accordance with an embodiment of the disclosed system and method.

The workflow of an embodiment of the spatial proximity estimation query is illustrated in FIG. 17B, The system creates a three-step query pipeline using R*-tree indexing and AABB-tree based structural indexing 240. After the nuclei 233, 234 and vessels 238 within one partitioned cuboid 236 (including further partitioned units of MBBs 232, 237) are identified as shown in portion 231 of FIG. 17B, the first step is to retrieve and decompress the geometry of vessels in low LOD 239, and compute Axis-Aligned Bounding Box (AABB) 245 on the mesh facets of subject vessels 238 in decompressed format 239 (also as shown in FIG. 8B, 87). Next in portion 240 of FIG. 17B, an R*-tree 245 is generated on the extracted AABBs of decompressed vessels 239 originally within cuboid 236 and MBB 237. For each nucleus 233, its nearest neighbor (AABB) 240 is found by R*-tree traversal, and the vessel with the identified AABB is identified as the nearest blood vessel 241 of the nucleus 247. The compressed data of the nearest vessel 248 is retrieved for high LOD geometry decompression. A structural AABB-tree_index 242 is created on the decompressed geometry, for example, polyhedrons 244 in respective MBBs 243 for accurate distance computation(s) 246. FIG. 17C illustrates an example algorithm providing detailed steps of the spatial proximity process shown in FIG. 17B, in accordance with another embodiment of the spatial proximity estimation query.

It is noted that in the application of for example, liver organ with artery and vein, the pipeline is applied to both types of blood vessels within the same partitioned cuboid for nearest distance computations. An aggregation step is further applied in certain embodiments, in order to collect the sums of nearest distances as performed over the entire 3D volume. The mean and standard deviation of the distance sums are computed for spatial proximity estimation of vascular patterns in liver.

In certain embodiments of the disclosed spatial proximity estimation query, the step of AABB-tree based structural indexing for all vessels is performed using smaller sized resolution (low LODs) 239. The step of generating geometry data 241 as shown in FIG. 17B, for nearest vessel objects is implemented with higher resolutions (high LODs). Thus, the usage of memory in such example embodiments, is thereby more efficient.

Figure 17D:
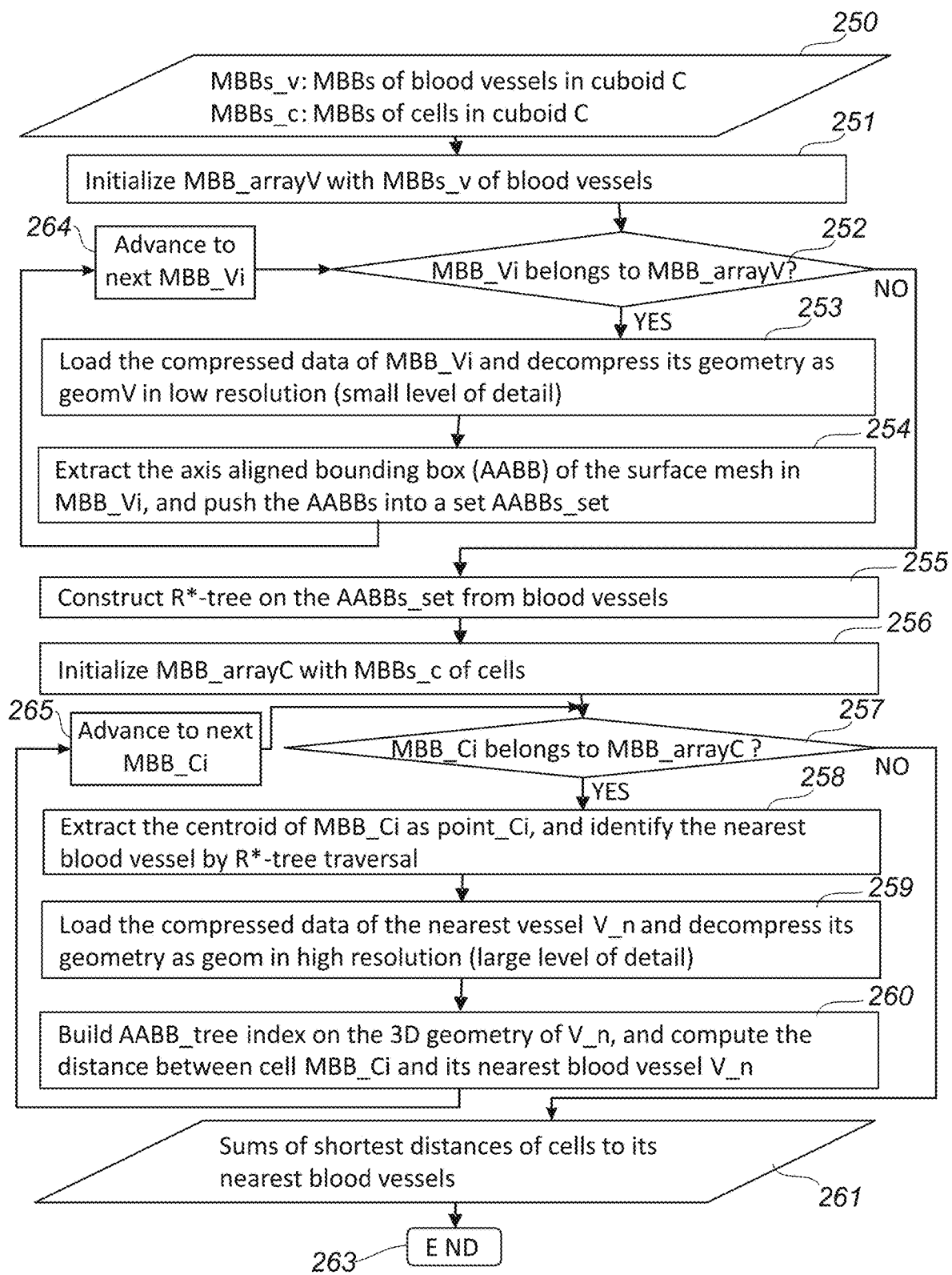
FIG. 17D is a flowchart illustration of an example spatial proximity estimation query in accordance with an embodiment of the disclosed system and method.

In another illustration of the spatial proximity estimation query, shown in FIG. 17D is a flowchart illustration of an example spatial proximity estimation query in accordance with an embodiment of the disclosed system and method. Beginning with step 250, similar to nearest neighbor spatial query, the system aims to estimate the spatial distribution of different types of vessels, for example, artery 20 and vein 21 as shown in FIG. 2. Spatial proximity estimation aims to explore inter-objects distribution in 3D space, based on distances between neighboring objects. In 3D digital pathology, spatial proximity estimation provides the quantitative expression of vascular spatial patterns for disease progression assessment. For example, in one embodiment, the disclosed system and method determines at the behest of a liver pathologist, that for each cell in liver tissue, the shortest path of the cell 23 to its neighboring artery vessel 20 is desired and the shortest path to its neighboring vein vessel 21, as particularly shown in FIG. 2.

In step 250, MBBs of blood vessels in cuboid C (MBBs_v) and MBBs of cells (or alternatively nuclei) in cuboid C (MBBs_c) are received as inputs to the spatial query engine. The system next initializes and generates an array MBB_arrayV in step 251 with received inputs of MBBs_v of blood vessels in cuboid C in step 250. The system in step 252 determines if the MBB_Vi belongs to MBB_arrayV. If so, the subject MBB includes an object vessel. Therefore the system next proceeds to load the compressed data of MBB_Vi and decompress its geometry as geomV in low resolution (small level of detail) in step 253. Next the system extracts the axis aligned bounding box (AABB) of the surface mesh in MBB_Vi, and pushes the AABBs into a set AABBs_set in step 254. Essentially the system computes all AABBs in step 254 and places them in a data structure, for example a Queue or array. This is applied to all blood vessels. All respective AABBs are processed for each blood vessel within partitioned cuboid C and stored for later extraction by the system described hereinbelow, in steps 258-260. As shown for example, in FIG. 17B, the system loads the geometry data, for example, of subject blood vessels 239, once decompressed, and generates F*-tree on AABBs of respective vessels of subject cuboids 236, in step 240. The system essentially performs a Nearest Neighbor (NN) query analysis described in FIG. 16A-C, for respective cells 247 to blood vessels 248, as shown in FIG. 17B.

The system in step 264 advances to the next MBB_Vi, by advancing counter Vi=Vi+1. The system iteratively checks in step 252, whether MBB_Vi belongs to MBB_arrayV. If so, the same processes 253 and 254 described above, are performed for current MBB_Vi. If not, the system proceeds to step 255 to construct an R*-tree on the AABBs_set generated from all processed blood vessels in respective MBB_Vi. Essentially in step 255 the system identifies the nearest blood vessel (using neighbor analysis) by an R*-tree traversal, for example. In step 256 the system initializes an MBB_arrayC with MBBs_c of cells. In step 257 the system determines if MBB_Ci belongs to MBB_arrayC, in order to determine whether the subject MBB includes cell object. If so, the system extracts the centroid of MBB_Ci as point_Ci and identifies the nearest blood vessel by R*-tree traversal in step 258. Next the system loads the compressed data of nearest blood vessel, V_n and decompresses its 3D geometry as geom generally in higher resolution (larger level of detail) in step 259 (also as shown in FIG. 17B, step 241). Essentially, once the system identifies its nearest blood vessel, it decompresses it to its 3D geometry in step 259.

The system next builds and generates an AABB_tree index on the 3D geometry of V_n and further computes the distance between cell MBB_Ci and its nearest blood vessel V_n in step 260 (also as shown in FIG. 17B, step 242). The system creates an AABB_tree on the surface map on the 3D geometry of V_n in order to computer accurate distances between respective cell MBB_Ci and its nearest blood vessel V_n. The system next advances the counter Ci=Ci+1 in step 265, to process the next MBB_Ci to iteratively process same steps 258-260, described hereinabove, for any remaining cells within MBB_arrayC. In steps 259-260, higher resolution is required when decompressing nearest vessel V_n because computation of distance requires higher resolution for greater accuracy in distance measurements. Hence, the sums of shortest distances of all respective cell(s) to nearest blood vessel(s) in step 261 are then determined with greater levels of accuracy, once each respective MBB_Ci is processed. Once it is determined that MBB_Ci is not part of the MBB_arrayC, the process proceeds to output the result of sums of shortest distances of all processed cells (within respective MBBs) to each of their nearest blood vessels in step 261. Hence, the spatial proximity estimation query process ends for subject cuboid C (i.e. MBB_Ci) at step 263.

It is noted that in the above-described steps of proximity estimation query in FIG. 17D, the step associated with AABB-tree based structural indexing for all queried vessels implements very small sizes (low LOD). The final phase is associated with computing distances between cells and only nearest vessel objects using higher resolution(s). Hence, the implementation of memory resources is accomplished with greater efficiencies and greater computational distance determinations. In addition, the above-described processes and/or methodologies associated with FIG. 17D for the disclosed 3D query system and method, are contemplated to be performed in certain embodiments, by the computing system (300) described hereinbelow, and in greater detail with reference to FIG. 24.

In accordance with another embodiment of the disclosed 3D query system and method, it is noted that the 3D query system provide parallel querying pipelines for the various described query workflows (for example, spatial join query, nearest neighbor query, spatial proximity estimation query) in order to achieve greater efficiency and scalability. Using partitioned cuboids, an embodiment of the 3D query system and method implements multiple query tasks through distributed computing paradigms such as for example, Hadoop or Spark on commodity clusters. In another implementation, MapReduce is used for the query task parallelization.

Figure 18:
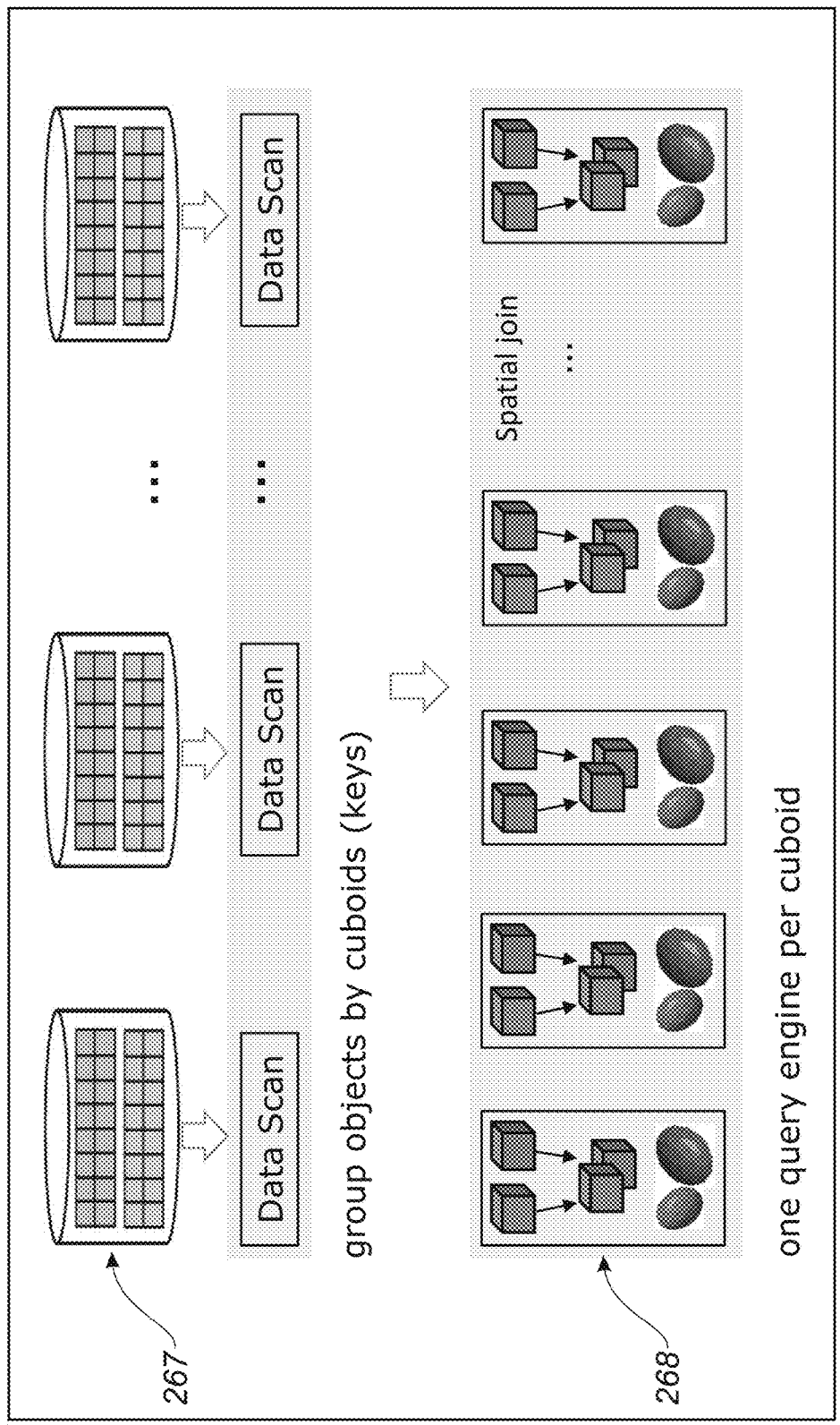
FIG. 18 illustrates an example implementation of spatial join query, in accordance with an embodiment of the disclosed system and method.

An example implementation of spatial join is shown in FIG. 18. It is noted that objects within the same cuboid are grouped by the Map function 267, and the cuboids are taken by Reducers for parallel spatial join execution 268.

The partitioned cuboid based query processing is parallelized using for example, a MapReduce programming model that includes three main steps, as described hereinbelow:

Map phase. In the Map phase, each Map task scans a portion of data from the master object index, performs R*-tree search on the partitioned cuboid index, and emits each record as an output value and its respective cuboid_id as the key.

Shuffle phase. All records with the same cuboid_id are sorted and prepared for reducer operations. Spatial objects from different datasets that belong to the same cuboid end up in the same partition to be processed by the same reducer.

Reduce phase. Each reducer performs the cuboid based spatial queries by executing the corresponding query workflow. If boundary objects need to be corrected for spatial join query, an additional result using a normalization function will be invoked for any removal of duplicates.

Evaluation of Compression: Since the data compression algorithm implemented in certain embodiments of the disclosed 3D spatial query system and method, is not lossless, high compression rates can incur potential structure distortion. In order to quantitatively measure the actual geometric difference between the original and the compressed 3D meshes, an approximate distance based metric is implemented as an evaluation approach.

For example, if $p=(x,y,z)$ is a 3D point; and S' is a surface, then the distance between p and S' is defined as Equation (2) reproduced hereinbelow.

Equation (2) is defined as:

$$d(p, S') = \min_{p' \in S'} e(p, p') = \min_{p' \in S'} \sqrt{(x-x')^2 + (y-y')^2 + (z-z')^2}$$

wherein, $p'=(x',y',z')$ is a point on surface S', and $e(;)$ is the Euclidean distance between two points p and p'. Given the distance between a point and a surface defined in the Equation (2) listed hereinabove, the Hausdorff distance is implemented to define the distance between two surfaces S and S'• using Equation (3) reproduced hereinbelow.

Equation (3) is defined as:

$$D(S, S') = \max\{d(p, S'), d(p', S)\}$$
$$= \max\{\sup_{p \in S} \inf_{p' \in S'} e(p, p'), \sup_{p' \in S'} \inf_{p \in S} e(p, p')\}$$

wherein sup and inf represent the supremum and the infimum, respectively. Given a set of uniformly sampled distances, the system defines the mean distance $D_m$ between two surfaces as the average of the surface integral of the distance divided by the area of the surface as defined by Equation (4) reproduced hereinbelow.

Equation (4) is defined as:

$$D_m(S, S') = \frac{1}{2} * \left( \frac{1}{|S|} \int_S d(p, S') ds + \frac{1}{|S'|} \int_{S'} d(p', S) ds' \right)$$

In such compression evaluation, the original 3D mesh is defined as surface S, and the compressed mesh with highest LOD is defined as S'. The vertexes of the compressed mesh are used as sampled points p'. So for each respective point p' over the compressed mesh, the system determines its closest point p on the original mesh S. The mean and RMSE (root-mean-squared error) are identified as the metric of geometric distance. Based on experimental analysis on blood vessel dataset, it has been determined that the mean and RMSE of geometric distance between the original mesh and the compressed mesh with highest LOD is in the range of 0.073 and 0.9%, respectively.

In addition to geometric difference computations, another evaluation metric is implemented based on spatial query results. For example, using spatial join query as a representative query, spatial join is performed on both the compressed data and the raw data. The query results are then compared by using the Jaccard coefficient defined by Equation (5) which is reproduced hereinbelow.

Equation (5) is defined as:

$$Jac(A, B) = \frac{A_{vol} \cap B_{vol}}{A_{vol} \cup B_{vol}} = \frac{A_{vol} \cap B_{vol}}{A_{vol} + B_{vol} - A_{vol} \cap B_{vol}}$$

Further defined are variables, A and B, which are defined as two spatial objects such as 3D cells; $A_{vol}$ and $B_{vol}$ are defined as their volumes, respectively. In order to evaluate how the compressed mesh affect the final query results, the system first compares the Jaccard coefficient of spatial objects with the original mesh, and further compares it to the results on the compressed mesh with the highest LOD. The mean and standard deviation of the Jaccard coefficient difference on one 3D dataset is about 0.03±0.21% for the join query. As spatial data is generated from image analysis algorithms which themselves result in errors, and spatial queries involve massive number of 3D objects, for statistical purposes such precision loss is considered negligible in practice.

In order to evaluate the loss of 3D data compression, the system uses Hausdorff distance to quantitatively compute the geometric difference between the original and the compressed 3D meshes. Specifically, for the 3D objects in for example, three datasets, the system randomly selects one partitioned cuboid with about 2500 nuclei and 200 vessels for validation with Hausdorff distance metric. As shown in Table 7.1 in FIG. 19B, the Hausdorff distances resulting for vessels and cells, are small enough to be considered negligible in practice.

In order to evaluate the effect of data compression on respective spatial queries, the system may implement in certain embodiments, spatial join as a representative benchmark query and use Jaccard coefficient as the corresponding validation metric. The system randomly selects one partitioned cuboid from each of the three nuclei test datasets (about 2500 nuclei), and computes the Jaccard coefficient of spatial joins on the original mesh ($J_o$); and the compressed mesh $J_c$.

The mean and standard deviation of their difference ($|J_o-J_c|$) are 0.035±0.43%, 0.057±0.27%, and 0.047±0.33% for 1×, 3× and 5× datasets, respectively. The results of Jaccard coefficient also reveal a minor loss of the compressed data in spatial queries.

Therefore, the details of 3D data compression can be significant in certain disclosed embodiments of the 3D spatial query system and method, and the corresponding ability to evaluate its effectiveness with multiple datasets. Once such errors are identified by the evaluation system, the 3D spatial query system and method can progressively increase or progressively decrease the requisite level of detail (LOD resolution) required for spatial query processes that implement progressive compression. Such ability to fine-tune LOD resolution during progressive compressive process, can impact the 3D spatial query results.

Data compression is proposed to fit the large-scale 3D spatial data into memory for low I/O and communication cost during query processing. By implementing progressive data compression, the data size is significantly reduced and such data can be stored in memory at very low footprint. The compressed data consists of multiple level of details, and on-demand decompression can be invoked to satisfy the requirements of different resolutions in various applications. Data compression can be implemented as a one-time step and the compressed data can be effectively implemented in different spatial queries with greater levels of accuracy in resultant outcomes of the various disclosed 3D spatial queries.

Figure 19A:
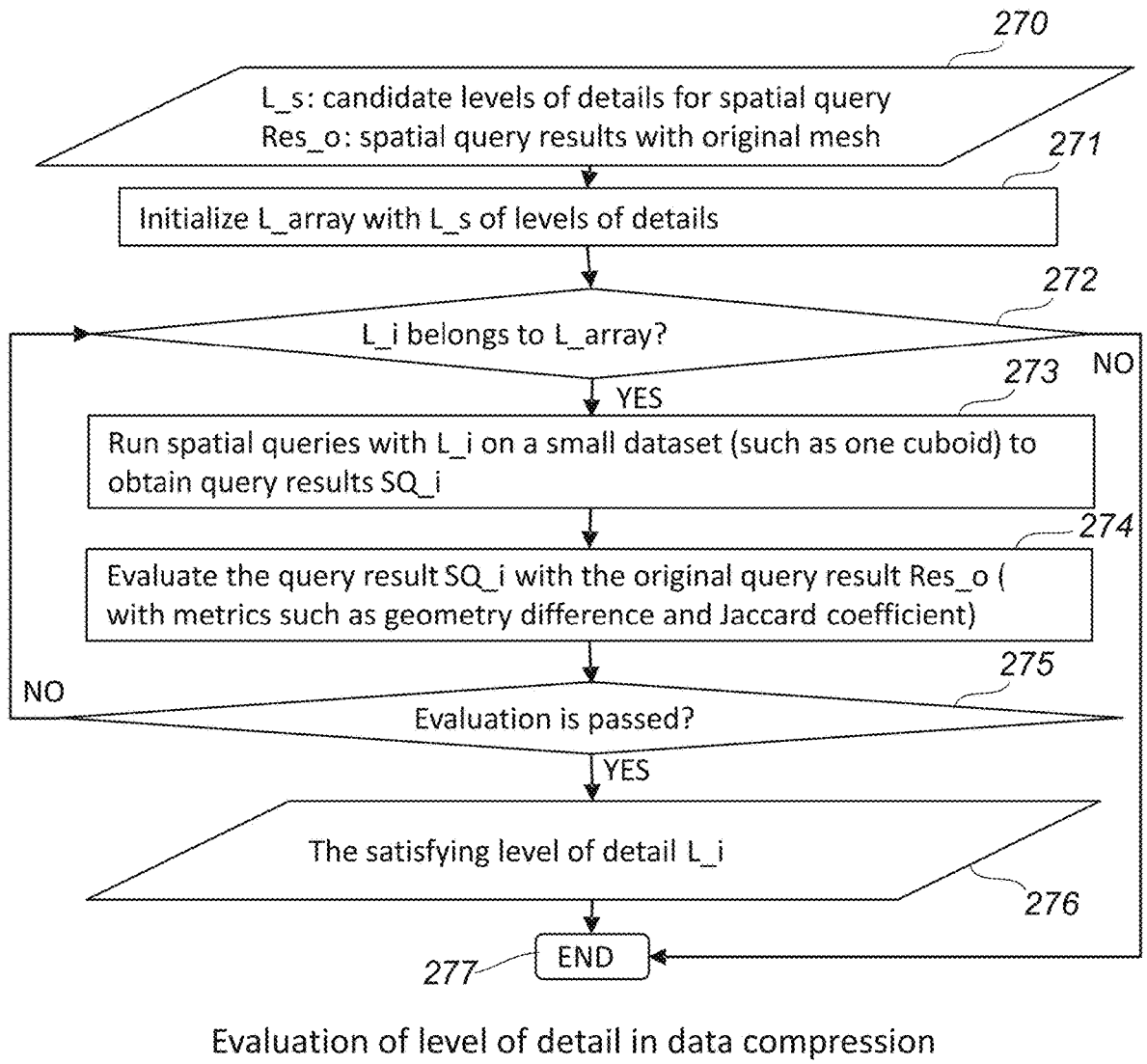
FIG. 19A is a flowchart illustration of the evaluation of level of detail in data compression, in accordance with an embodiment of the disclosed system and method.
Figure 22:
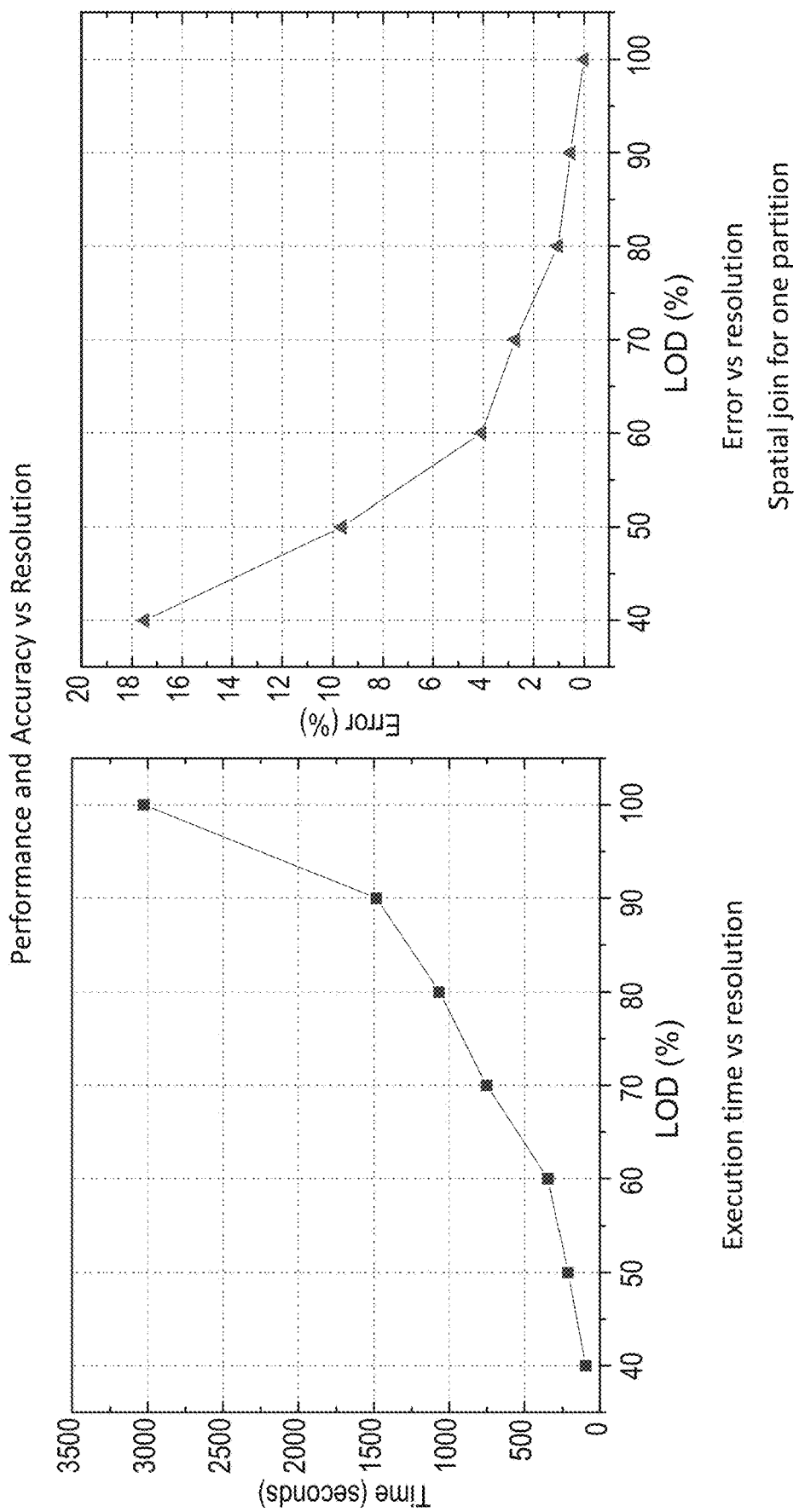
FIG. 22 is a side-by side graphical representation of execution performance and accuracy of results associated with varying LOD resolution values, in accordance with an embodiment of the disclosed system and method, as further illustrated individually in FIGS. 22A-22B.

Shown in FIG. 19A is a flowchart illustration of the evaluation process of the accuracy of query results for particular level(s) of detail (LOD) implemented during data compression, in accordance with an embodiment of the disclosed system and method (and as also described hereinbelow in connection with FIGS. 22-22B). By way of background, as 3D objects are often represented with multiple level of details (LODs) in accordance with an embodiment of the disclosed Evaluation of Compression System, the effect of different LOD representations on various spatial query performance are hence, evaluated.

Hence, disclosed Evaluation of Compression System tests and determines the effect of different LOD representations on spatial query performance. Spatial join query for example, is implemented as a representative benchmark query in order to evaluate the execution time and error rate for quantitative spatial measurement of intersection volumes, as shown in FIG. 22.

The Evaluation of Compression System first runs spatial join query on one small partitioned cuboid containing for example, 871 objects with seven levels of detail ranging from 40% to 100%. In the test of spatial join query processing, for each pair of objects, the evaluation system first performs MBB filtering. Then for the candidate pairs with MBB intersection, the evaluation system decompresses their geometries with specified LOD, performs geometry intersection testing, and computes the intersection of volume(s) individually for each pair.

Figure 22A:
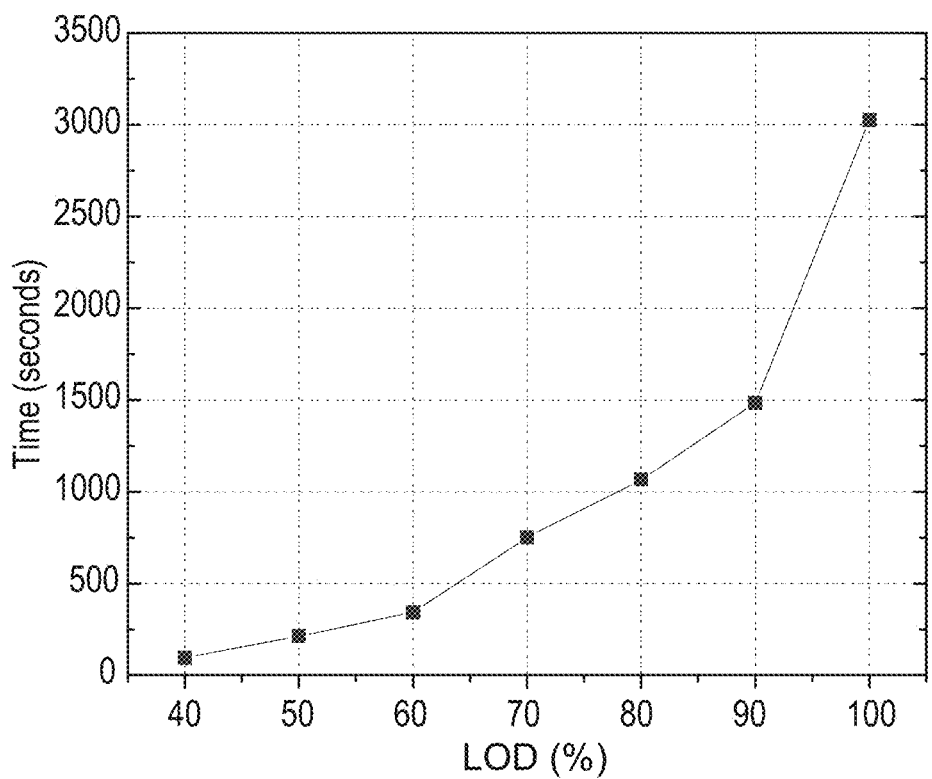
FIG. 22A is a graphical representation of execution performance time associated with varying LOD resolution values, in accordance with an embodiment of the disclosed system and method.
Figure 22B:
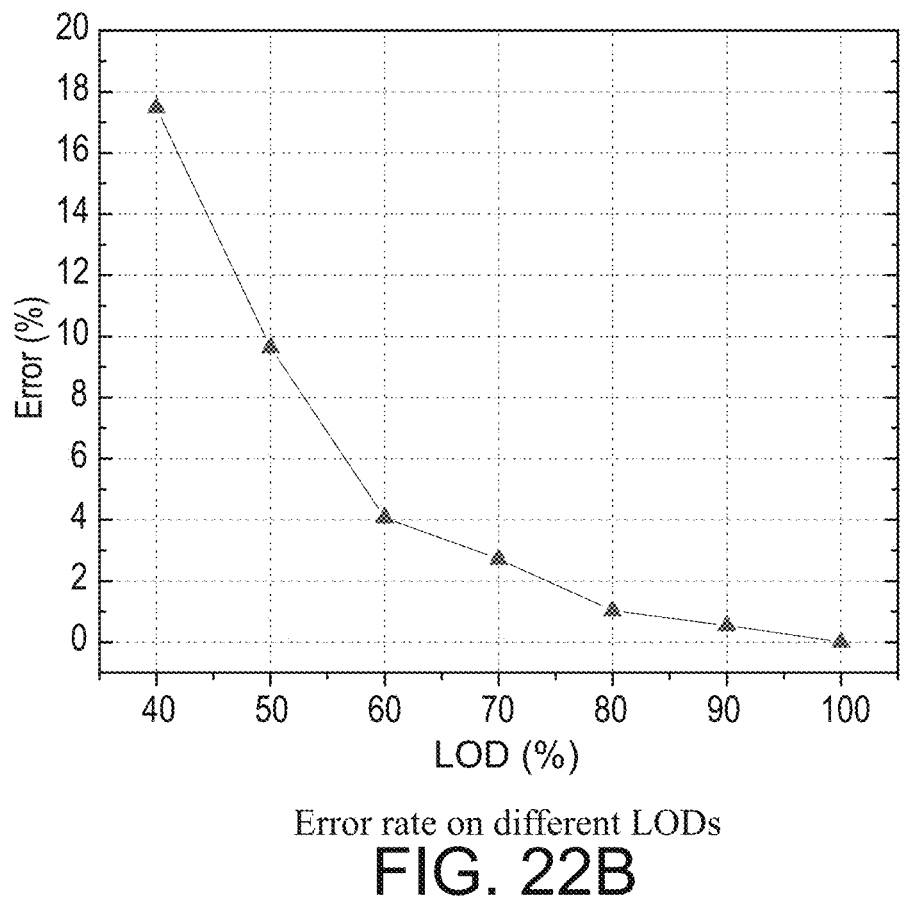
FIG. 22B is a graphical representation of error rates and accuracy of performance associated with varying LOD resolution values, in accordance with an embodiment of the disclosed system and method.

As the graph in FIG. 22A shows, the execution time increases dramatically with increasing LODs. For LOD with 50%, it only takes 213 seconds. However the time increases to 3,026 seconds for 100% LOD, a fourteen (14) times increase in time. The reason for such significant increase of execution time is that objects with larger LOD have more complex geometries, and the respective 3D geometry computation dominates the cost of the spatial join query.

The geometry simplification of objects leads to precision loss in the query results. The error rates of resulting intersection volume across different LODs is presented in the graph shown in FIG. 22B. Compared to the 100% LOD, the error rate for 50% is 9.64%. For a LOD with 70%, the error rate is only 2.72% with query time of 750 seconds, a quarter of the time from 100% LOD. Shown in FIG. 22B is an error rate of 0.54% using 90% LOD. However, the query runs twice faster (i.e. ~1484 seconds) at 94% LOD, than if set at 100% LOD (~3000 seconds) as shown in FIG. 22A. Thus, there is a trade-off between query time and respective error rates for queries on objects implementing different LODs. In an embodiment of the disclosed 3D spatial query system and method, users can specify the LOD for spatial queries to balance query efficiency and results for precision, based on the specific application requirements.

In flowchart shown in FIG. 19A, beginning with step 270, the evaluation of compression system inputs candidate levels of details for spatial query (L_s) and spatial query results including original mesh geometry (Res_o). The system initializes L_array with L_s candidate LOD level of details in step 271. In step 272, the system checks whether the candidate levels of details L_i belongs to L_array. If not, the system ends the process in step 277. If so, in step 273, the system runs spatial queries with L_i on a small dataset (such as one cuboid) to obtain query results SQ_i. The system next evaluations the query result SQ_i with the original query result Res_o (with metrics such as geometry difference and Jaccard coefficient) in step 274. The system next determines if the evaluation is passed in step 275 in terms of error rates, time rates for respective L_i. If not, the system increments the counter for L_i, i=i+1, and proceeds to step 272 to iteratively perform same operations on next L_i, in steps 272-274, respectively. If the evaluation is indeed passed in step 275, the evaluation system outputs the satisfying level of detail L_i, at which point, the evaluation process ends in step 277.

FIG. 19A illustrates an embodiment in which the system and/or user computing device can specify a level of detail (LOD) during spatial query processing by selection of the LOD that meets the specific requirements in terms of respective speed and error rates for a particular LOD i. As shown in FIG. 22B, which details results, the error rates at 90-100% LOD is significantly decreased to approximately <0%-0.54% but, with execution times increasing from approximately 1500-3026 seconds, in same range of LODs. The above-described processes and/or methodologies associated with any of the Figures described hereinabove including FIG. 19A, in connection with the disclosed 3D query system and method, are contemplated to be performed in certain embodiments, by the computing system (300) described hereinbelow, and in greater detail with reference to FIG. 24.

Figures 19B, 20A:
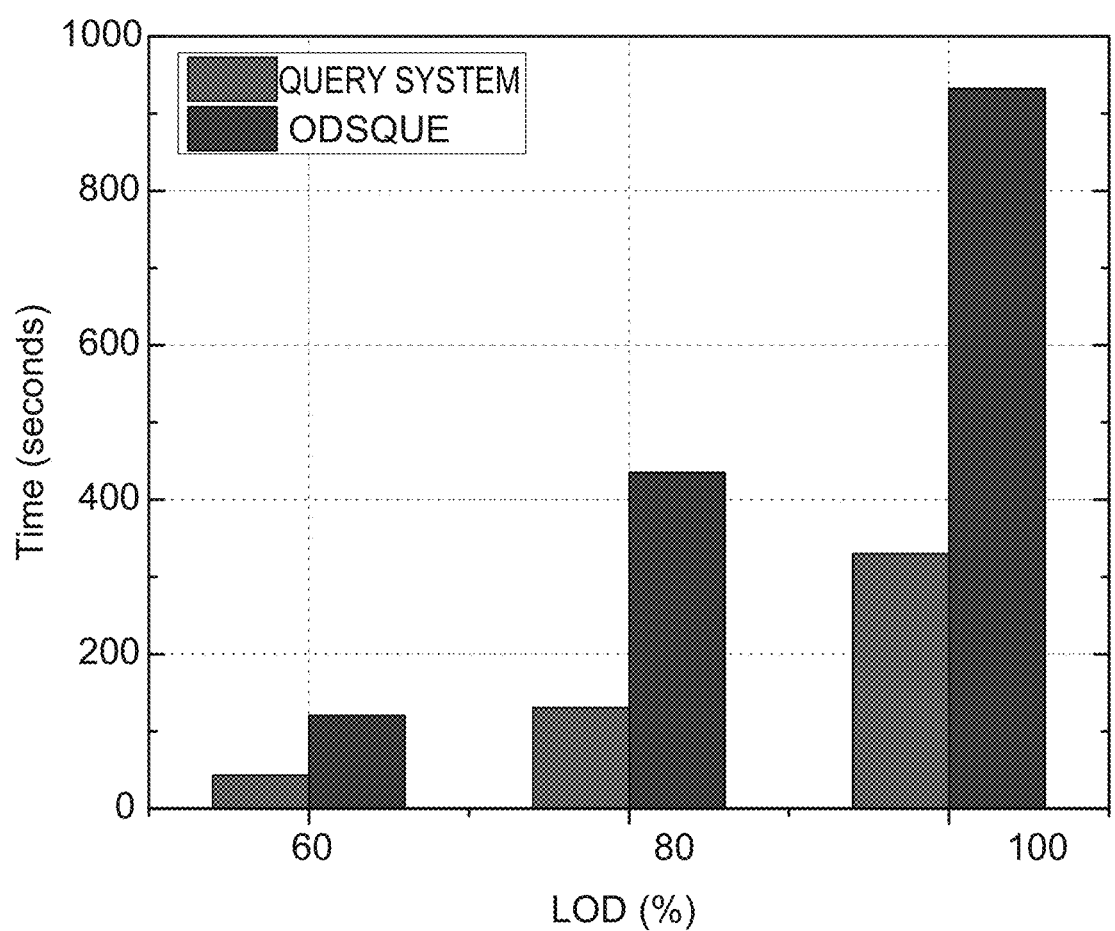
FIG. 19B is a table representing the evaluation results using Hausdorff distance metric.
FIG. 20A is a graphical representation of the performance comparison between the 3D query system and other known system, in accordance with an embodiment of the disclosed system and method.
Figures 20B, 20C:
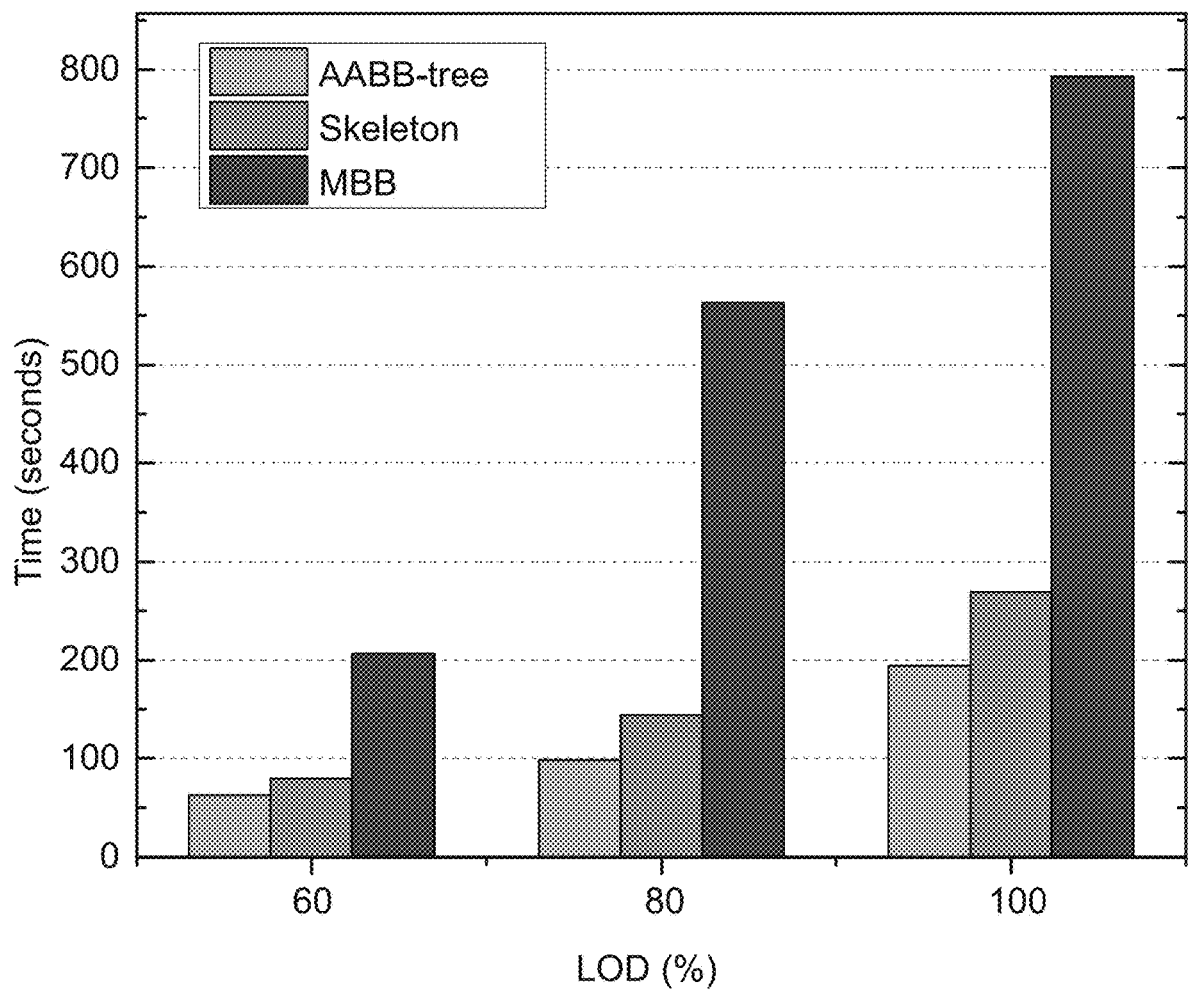
FIG. 20B is a graphical representation of the effect of structural indexing on distance-based spatial queries for complex structures, in accordance with an embodiment of the disclosed system and method.
FIG. 20C is a table representing results associated with 3D data performance studies using respective data sets of 1X, 3X, and 5X, in accordance with an embodiment of the disclosed system and method.

Evaluation of 3D Spatial Query System: In order to evaluate the 3D spatial query engine, spatial join is used as a representative benchmark query to test its standalone performance, and validate the effect of structural indexing by nearest neighbor search and spatial proximity estimation. For the performance test, the spatial query is executed on a cluster node as a single thread application. The test data is from two 3D result sets (2476 vs 2503 nuclei) within one partitioned cuboid, with 202 blood vessels in the same cuboid. FIGS. 20A and 20B present the query execution time versus multiple LODs of the dataset.

An embodiment of the disclosed 3D query system is executed in a single thread on the test dataset and its execution time is compared with that of ODSQUE, the query engine of Hadoop-GIS 3D [76]. FIG. 20A shows the spatial join performance comparison for the two engines. The disclosed system performs significantly better than ODSQUE at all LODs. Specifically, for the original data with 100% LOD, the disclosed system takes 5 minutes 30 seconds, while ODSQUE uses 15 minutes 32 seconds, about 3 times slower. Such difference can be mainly attributed to ODSQUE's extensive I/O cost as it needs to read all the data from HDFS for geometric intersection testing, which is eliminated in the disclosed system with in-memory based approach.

When profiling the 3D query system for the data and computation intensive spatial join for cross-matching, it is observed that the cost of reading and parsing MBB data from memory is 0.61%; R*-tree construction cost is 0.02%; MBB filtering cost is 0.33%; on-demand data decompression is 2.03%; and spatial refinement and measurement cost is 97.01%. With fast development of CPU speed, spatial index construction takes very little time during the query process, which encourages development of the index-on-demand approach to support spatial queries. It is further observed that 3D geometric computation dominates the cost, which can be accelerated through parallel computation on a cluster.

As shown in FIG. 20B, structural indexing significantly boosts distance-based spatial queries for complex structures. The effect of structural indexing by running skeleton and AABB-tree based nearest neighbor search on the test dataset with 3D blood vessels is tested. An MBB based indexing without any structural indexing is used for comparison. As the MBB approach computes the distance between nuclei and vessels by checking all the vessel facets in a brute-force nested loop manner, it takes much longer time across all LODs as compared to the two structural indexing approaches.

Shown in FIG. 20B, for the dataset with 60% LOD, the time for AABB-tree indexing and skeleton indexing is less than 100 seconds. Whereas MBB indexing takes about 200 seconds. Also shown in FIG. 20B, for the datasets with 80% and 100% LOD, the two structural indexing are about 4 to 5 times faster, than the traditional MBB indexing. Note that AABB-tree indexing performs slightly better than skeleton based indexing, as the cost of tree creation and traversal is less than that of skeleton extraction and Voronoi diagram construction for complex objects.

Hence, the on-demand in-memory based 3D spatial query engine exhibits significant advantages over known systems. It fully takes advantage of multi-level indexing and data decompression for processing multiple types of spatial queries. Compared to the pure disk based spatial query engine, it achieves much better performance. The disclosed 3D spatial query system among other improvements, provides two types of structural indexing: skeleton based and hierarchical tree based, which significantly accelerate distance based queries as compared to the traditional MBB indexing.

Other Experimental Results: Three datasets from analytical pathology imaging are used for system performance evaluation. The 3D objects including nuclei (cells) and blood vessels derived from 3D image volumes with different number of slides, which have been validated and represented in OFF format. The respective dataset sizes are at 1×, 3×, and 5×, as shown in Table 9.1, FIG. 20C.

The performance of an embodiment of the disclosed 3D spatial query system and method, is tested on a cluster environment. The cluster has five nodes with 124 cores (Intel® Xeon® CPU E5-2650 v3 at 2.30 GHz). Each node in example test includes 5 TB hard drive at 7200 rmp and 128 GB memory. Cluster nodes are connected via a 1 Gb network and the OS for each node is CentOS 6.7 (64 bit). The example implements Apache Hadoop 2.7.1 as MapReduce platform for distributed parallel computing, and adopt Boost 1.57.0 and libraries for 3D structural indexing, geometric computation and spatial measurement. The SpatialIndex library is extended for 3D R*-tree_index creation. The original 3D datasets are uploaded in HDFS and the replication factor is set as 3 for each data node.

Figures 20D, 20E:
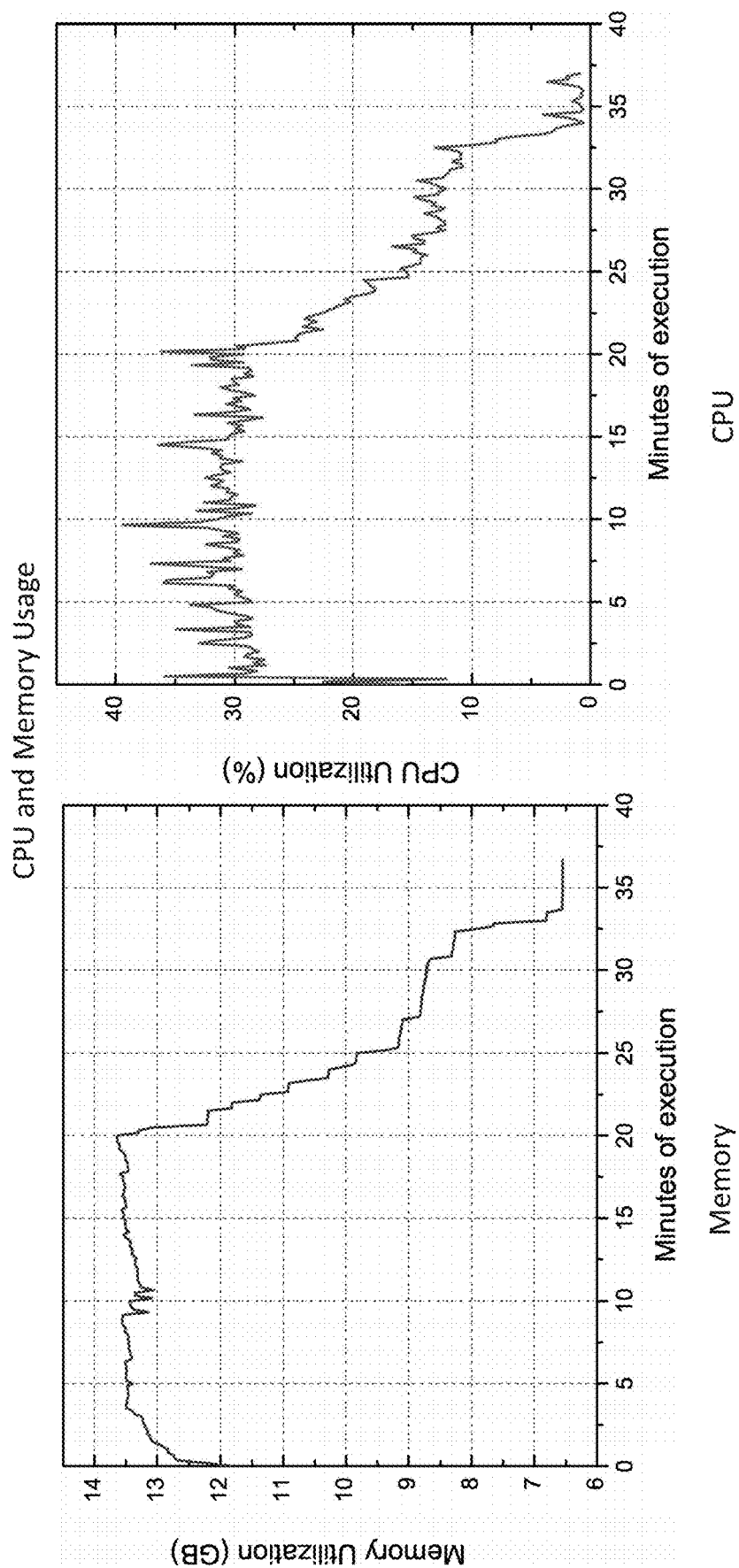
FIG. 20D is a graphical representation of the memory utilization associated with spatial join query execution, in accordance with an embodiment of the disclosed system and method, as also shown in FIG. 20F.
FIG. 20E is a graphical representation the CPU utilization associated with spatial join query execution, in accordance with an embodiment of the disclosed system and method, as also shown in FIG. 20G.

In order to evaluate the resource utilization of the disclosed 3D query system and method, the memory and CPU usage is tested for a single node with spatial join query on the largest dataset 5×, and the results are shown in graphs shown in FIGS. 20D and 20E.

Figure 20F:
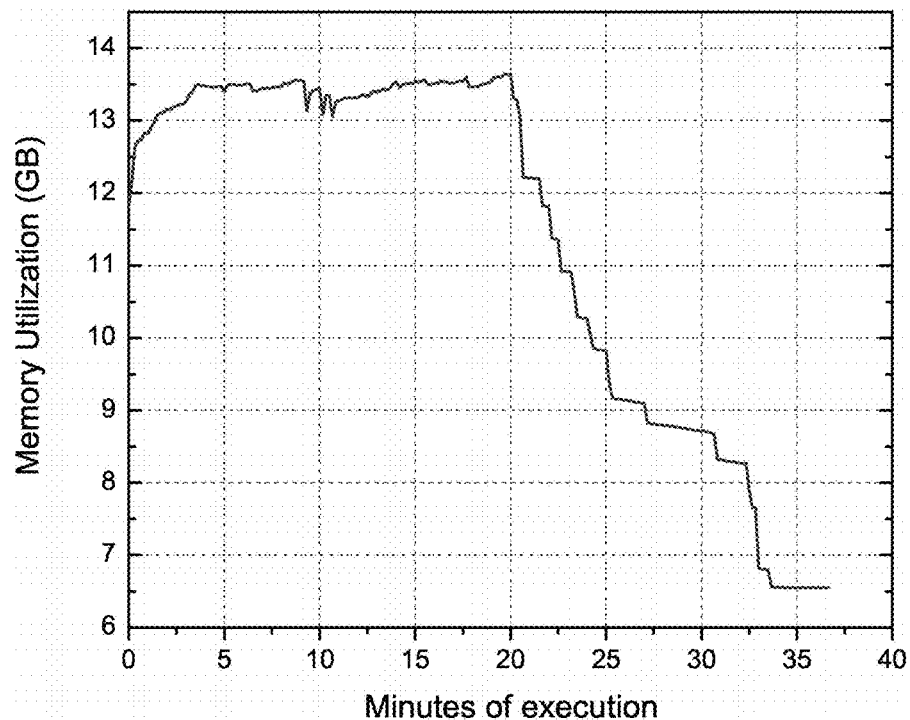
FIG. 20F is a graphical representation of the memory utilization associated with spatial join query execution, in accordance with an embodiment of the disclosed system and method, as also shown in FIG. 20D.
Figure 20G:
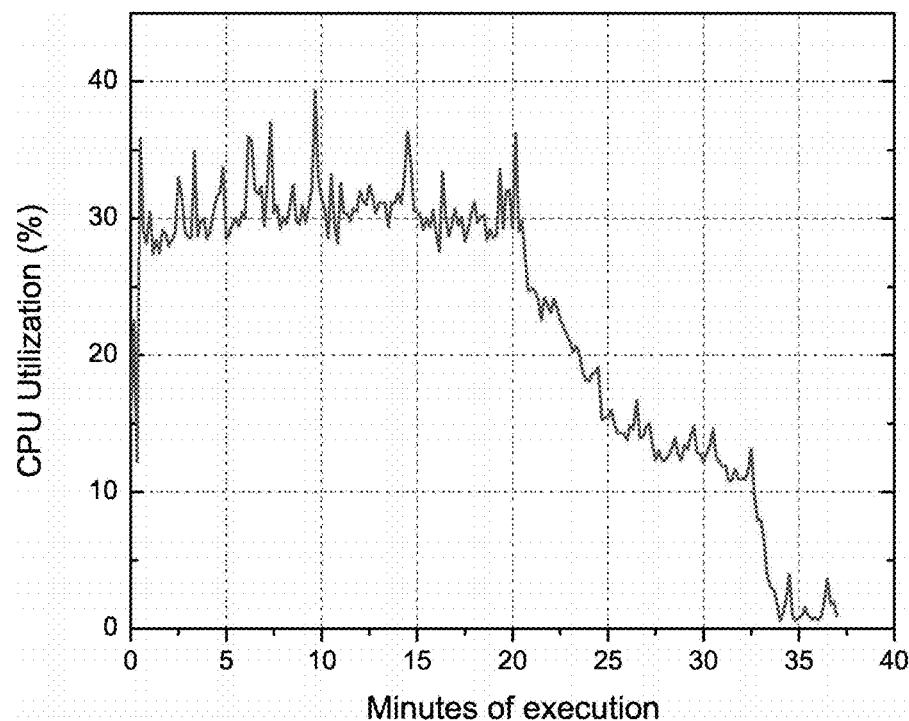
FIG. 20G is a graphical representation the CPU utilization associated with spatial join query execution, in accordance with an embodiment of the disclosed system and method, as also shown in FIG. 20E.

FIGS. 20D and 20F illustrate the memory usage of the 3D spatial query system. When implementing the 5× dataset with size of 460 GB, the stages of data compression and spatial join querying implement maximal memory usage, which is still less than 14 GB. The reason for such low memory usage is due to the disclosed 3D spatial query on-demand decompression, which occurs at the refinement step during a spatial join query. In such spatial join query only one pair of 3D objects at a time, are decompressed into memory for geometric computation. The sequential execution in a task of such geometry operations, leads to more efficient memory utilization. Note that in FIGS. 20D and 20F, about 6 GB memory is pre-allocated for query task parallelization before the actual execution of queries. The CPU utilization is shown in FIG. 20E and FIG. 20G, with 20 physical cores on the node. As shown, for spatial join query, the CPU usage is about 30%.

Figure 21:
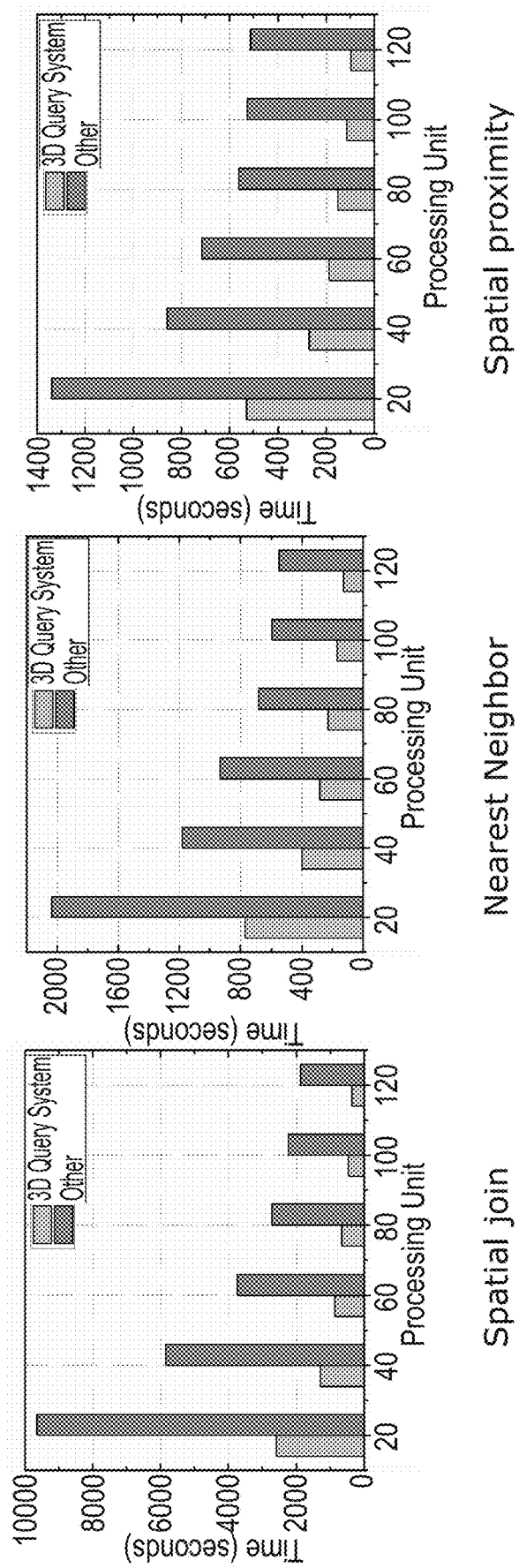
FIG. 21 is a side-by-side graphical representation of performance comparisons between the 3D query system and other systems, in accordance with an embodiment of the disclosed system and method, as further illustrated individually in FIGS. 21A-21C.
Figure 21A:
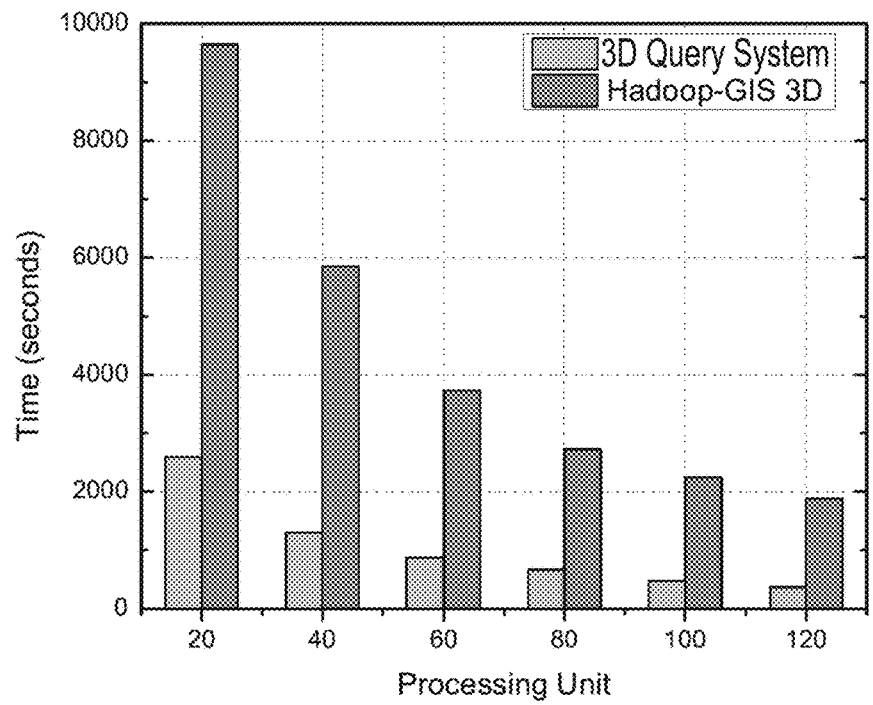
FIG. 21A is a graphical representation of execution performance associated with spatial join query, in accordance with an embodiment of the disclosed system and method.
Figure 21B:
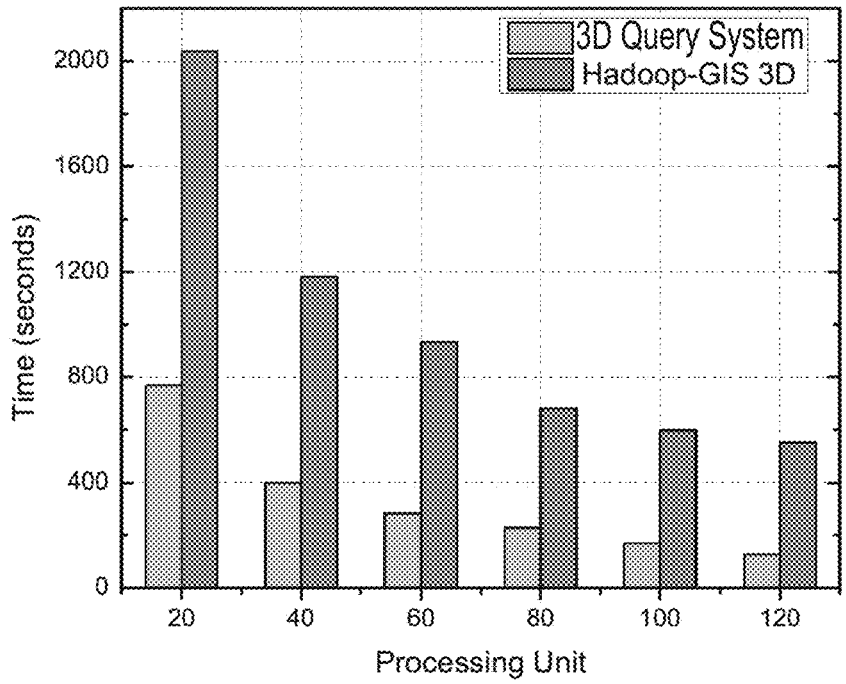
FIG. 21B is a graphical representation of execution performance associated with nearest neighbor query, in accordance with an embodiment of the disclosed system and method.
Figure 21C:
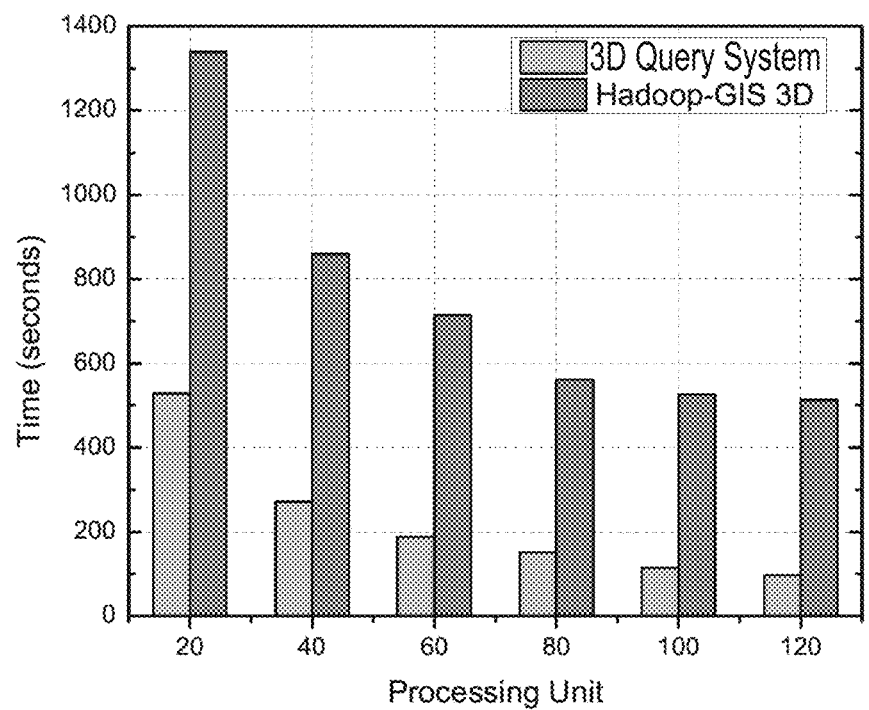
FIG. 21C is a graphical representation of execution performance associated with spatial proximity estimation, in accordance with an embodiment of the disclosed system and method.

For the purpose of comparison, we run the three spatial queries on both the 3D spatial query system and Hadoop-GIS 3D on the dataset at the 3×3D image volume with 168 slides, and present the results in FIGS. 21-21C, respectively. FIG. 21 is a side-by-side comparison of performance comparison between 3D query system and other systems.

The results shown in FIG. 21 illustrate the query execution time versus the number of parallel processing units (PPU). Using the MapReduce implementation, the number of PPU corresponds to the number of mapper and reducer tasks in our system. Both systems exhibit good scalability for the three types of spatial queries. However, the disclosed 3D query system outperforms Hadoop-GIS 3D significantly with a speedup of from 2.31 to 3.02 for spatial join query across different number of PPUs. As the disclosed 3D query system uses all data in memory (as stored in all nodes), it significantly reduces data scanning from HDFS, and minimizes data shuffling between cluster nodes. Even 3D objects are stored in a compressed form in the disclosed 3D spatial query system, with multi-level spatial index based filtering and on-demand decompression. The extra cost for compression is small and the overall gained efficiency is significant.

Figure 23:
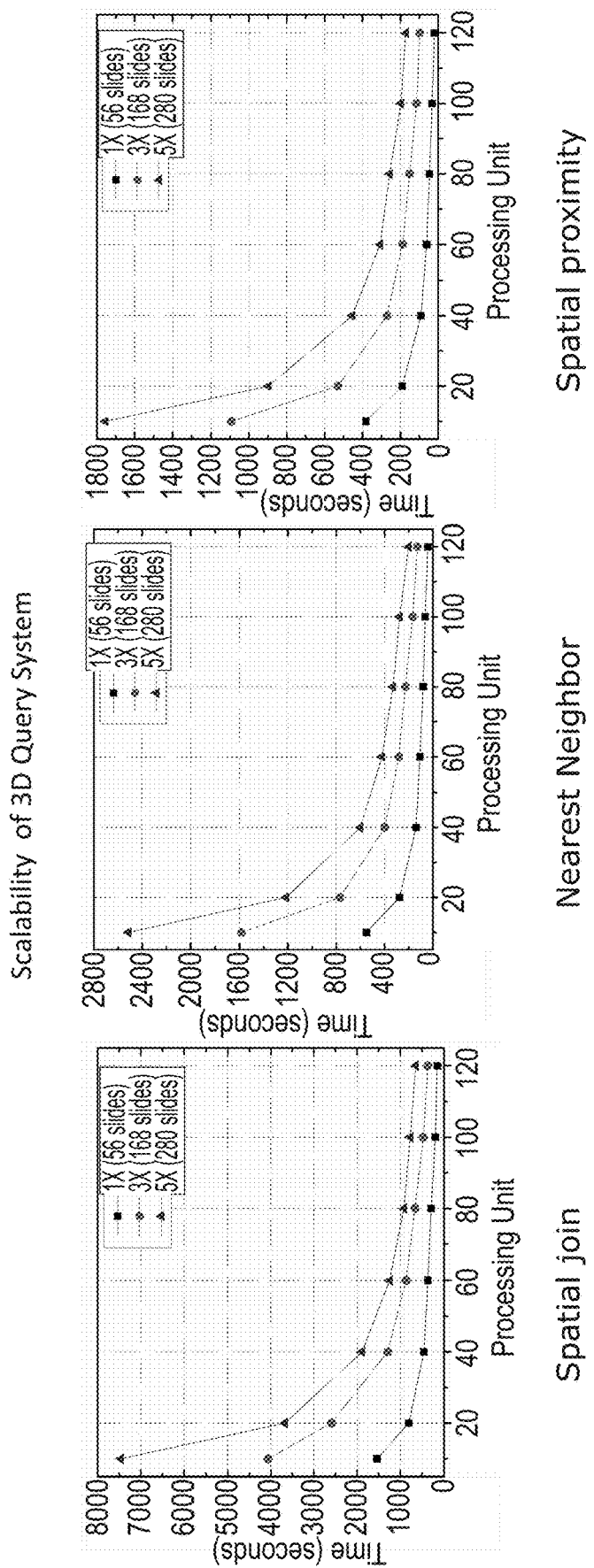
FIG. 23 is a side-by side graphical representation of performance outcomes associated with scalability of the 3D spatial query system as compared using varying number of processing units, in accordance with an embodiment of the disclosed system and method, as further illustrated individually in FIGS. 23A-23C.
Figure 23A:
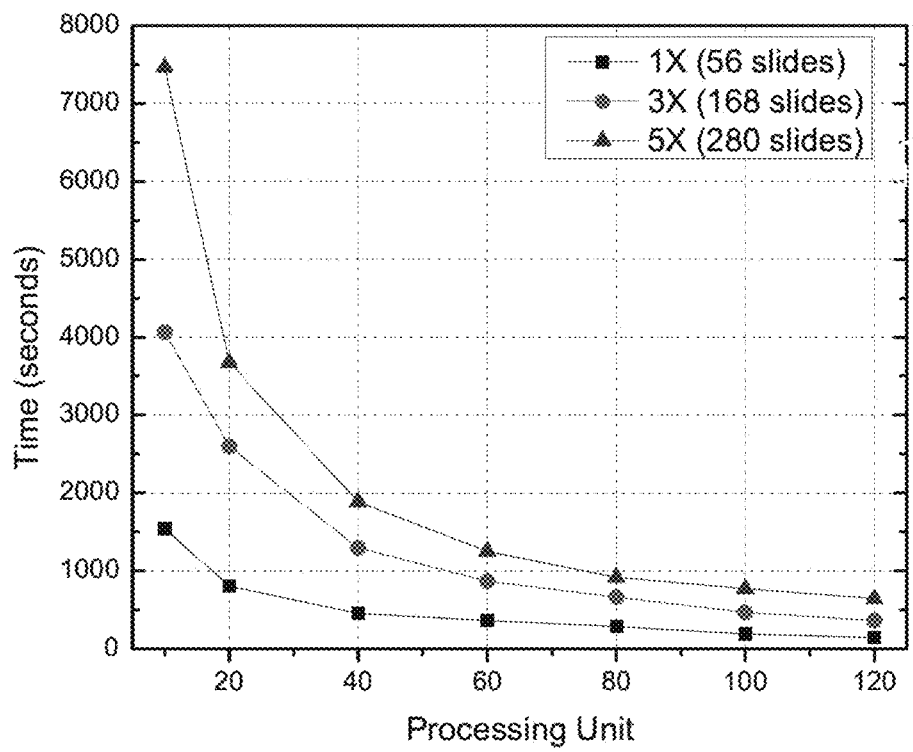
FIG. 23A is a graphical representation of performance related to scalability of 3D query system using spatial join, as associated with varying number of processing units, in accordance with an embodiment of the disclosed system and method.
Figure 23B:
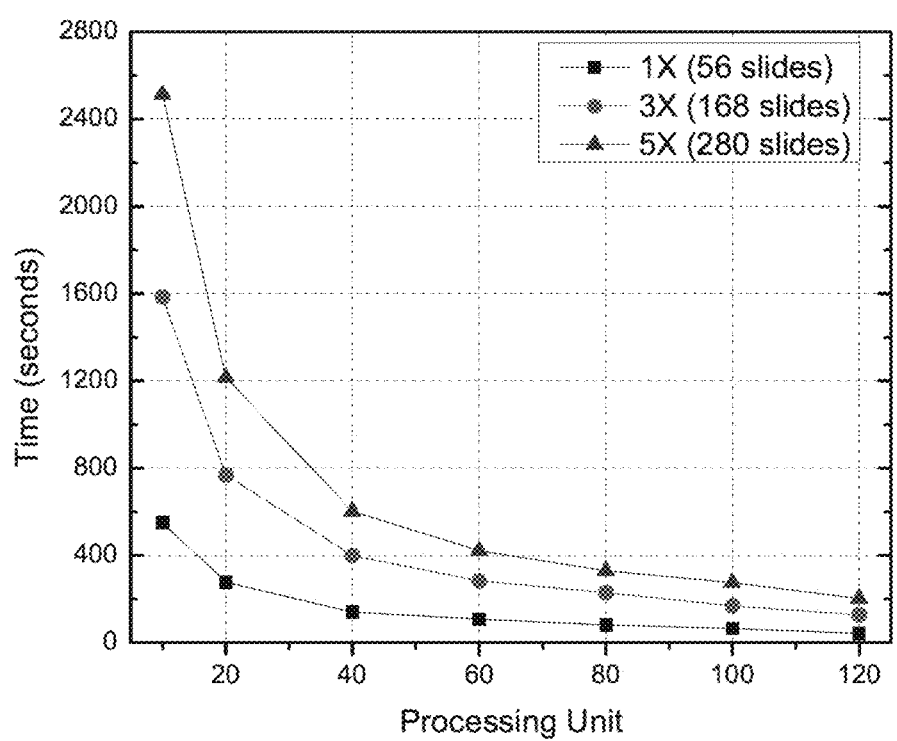
FIG. 23B is a graphical representation of performance related to scalability of 3D query system using nearest neighbor, as associated with varying number of processing units, in accordance with an embodiment of the disclosed system and method.
Figure 23C:
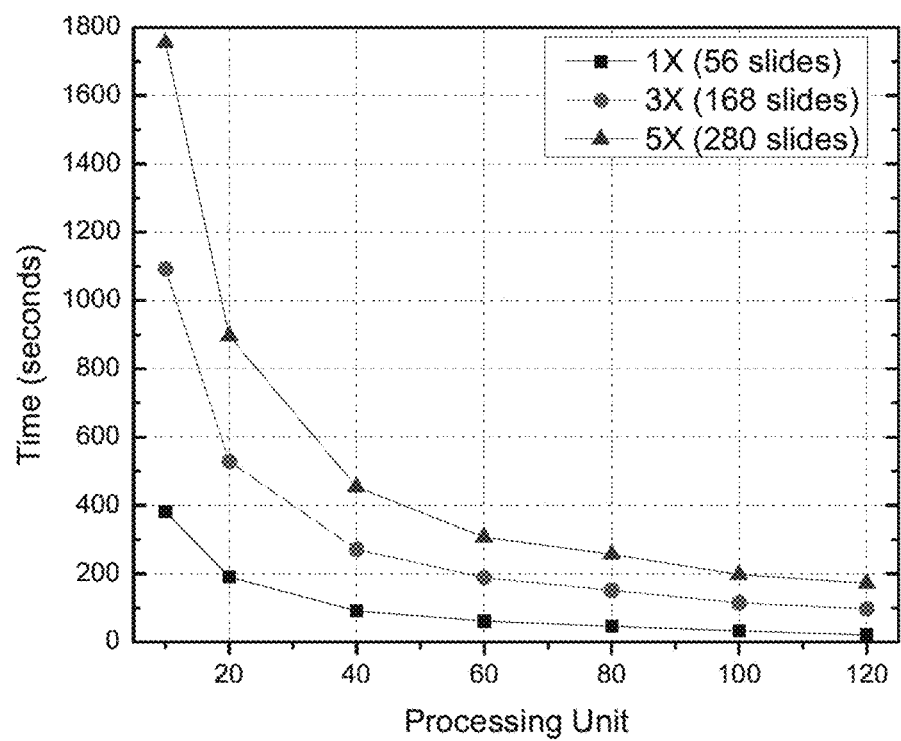
FIG. 23C is a graphical representation of performance related to scalability of 3D query system using spatial proximity estimation, as associated with varying number of processing units, in accordance with an embodiment of the disclosed system and method.

The scalability of the system with the above described types of spatial queries in FIGS. 23-23C, respectively. Datasets include 1×, 3×, and 5× datasets on 100% LOD geometry, with varying number of PPUs. A continuous decline of query time is shown in FIGS. 23-23C by increasing the number of reducers. This achieves a nearly linear speedup in spatial join query, e.g., the time is reduced by half when the number of reducers is increased from 10 to 20.

The system also exhibits an improved scale up. For example, with 40 processing units, the time for spatial join query on the 5× dataset is about 5 times of that for spatial join query on the 1× dataset.

Hence, in conclusion observed is that the 3D spatial query system framework provides a basic blueprint for implementing an in-memory based spatial query system with distributed computing paradigms such as for example, MapReduce. Through the development and deployment of known query processing systems, the disclosed system provides scalable query support with cost effective architecture. The example 3D query system is based on a decoupled architecture in which the in-memory based spatial query engine provides essential spatial query processing capability, and known systems enable running partition based spatial queries on a massive scale.

In the disclosed example system, several fundamental problems for in-memory based spatial query data compression, spatial data partition, and multi-level indexes supported query processing are addressed. The example system is memory efficient with one-time data compression and on-demand data decompression during query processing. Further, the example system provides tradeoffs between execution time and accuracy with multiple levels of detail representations. Experiments indicate that the disclosed 3D query system is significantly faster than the pure disk based approaches for computationally-intensive complex queries.

Any of the above-described processes and/or methodologies associated with the disclosed 3D query system and method, are contemplated to be performed in certain embodiments, by the computing system (300) described hereinbelow, and in greater detail with reference to FIG. 24.

In addition, as described in greater detail below in connection with FIGS. 24-27, an example 3D query system may embody, include, or may otherwise be communicatively coupled to, a computing system, such as computing system 300, computing system 350 or computing system 400.

Figure 25:
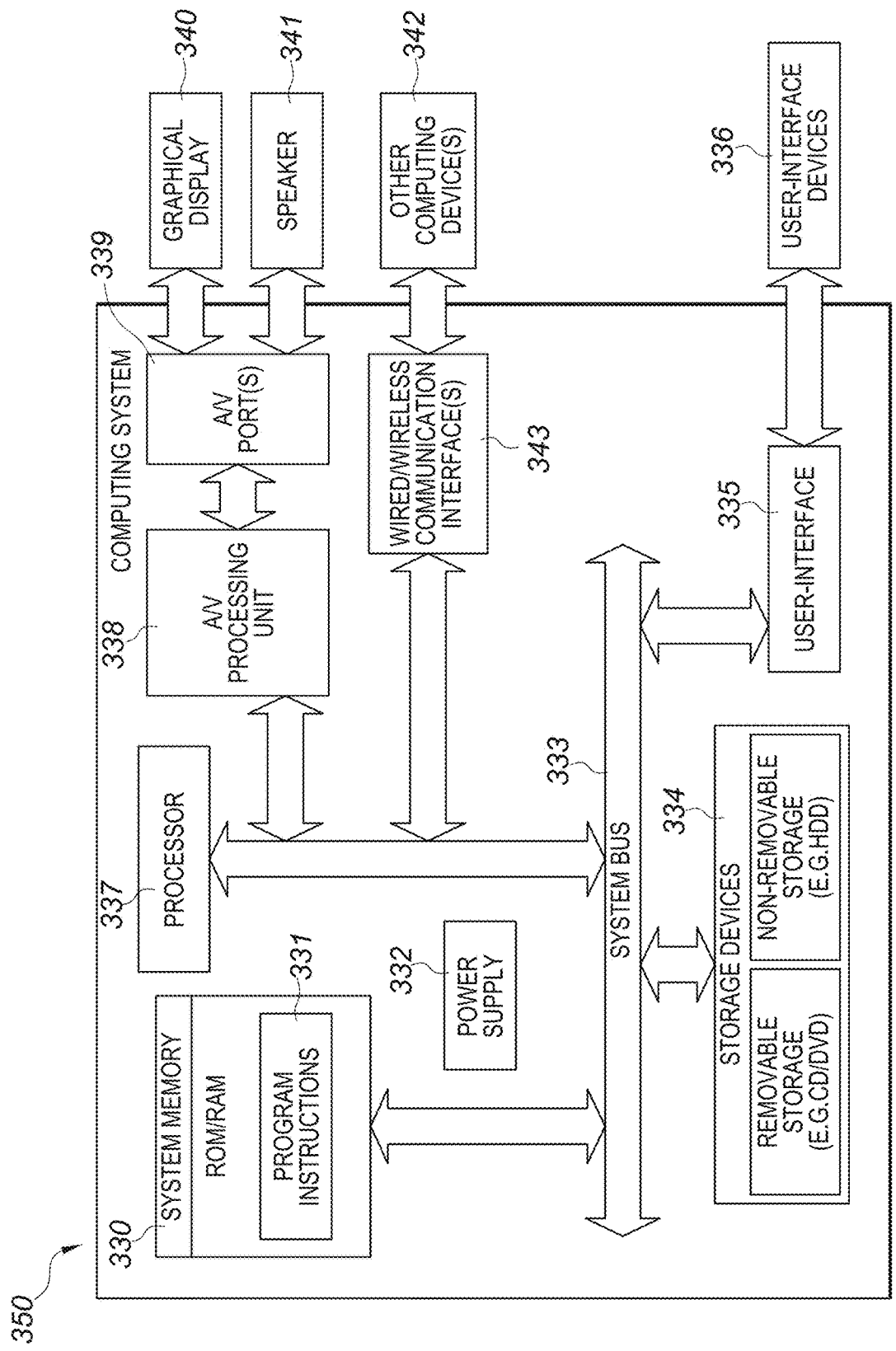
FIG. 25 illustrates a system block diagram in accordance with an embodiment of the 3D spatial query system, including an example computing system.

Shown in FIG. 25 is computing system 350 which may include at least one processor 337 and system memory 330. In an example embodiment, computing system 350 may include a system bus 333 that communicatively connects processor 337 and system memory 330, as well as other components of computing system 350. Depending on the desired configuration, processor 337 can be any type of processor including, but not limited to, a microprocessor (μP), a microcontroller (μC), a digital signal processor (DSP), or any combination thereof. Furthermore, system memory 330 can be of any type of memory now known or later developed including but not limited to volatile memory (such as RAM), non-volatile memory (such as ROM, flash memory, etc.) or any combination thereof.

An example computing system 350 may include various other components as well. For example, computing system 350 includes an A/V processing unit 338 for controlling graphical display 340 and speaker 341 (via A/V port 339), one or more communication interfaces 343 for connecting to other computing systems 342, and a power supply 332. Graphical display 340 may be arranged to provide a visual depiction of various input regions provided by user-interface module 335. For example, user-interface module 335 may be configured to provide a user-interface and graphical display 340 may be configured to provide a visual depiction of the user-interface.

Figure 26:
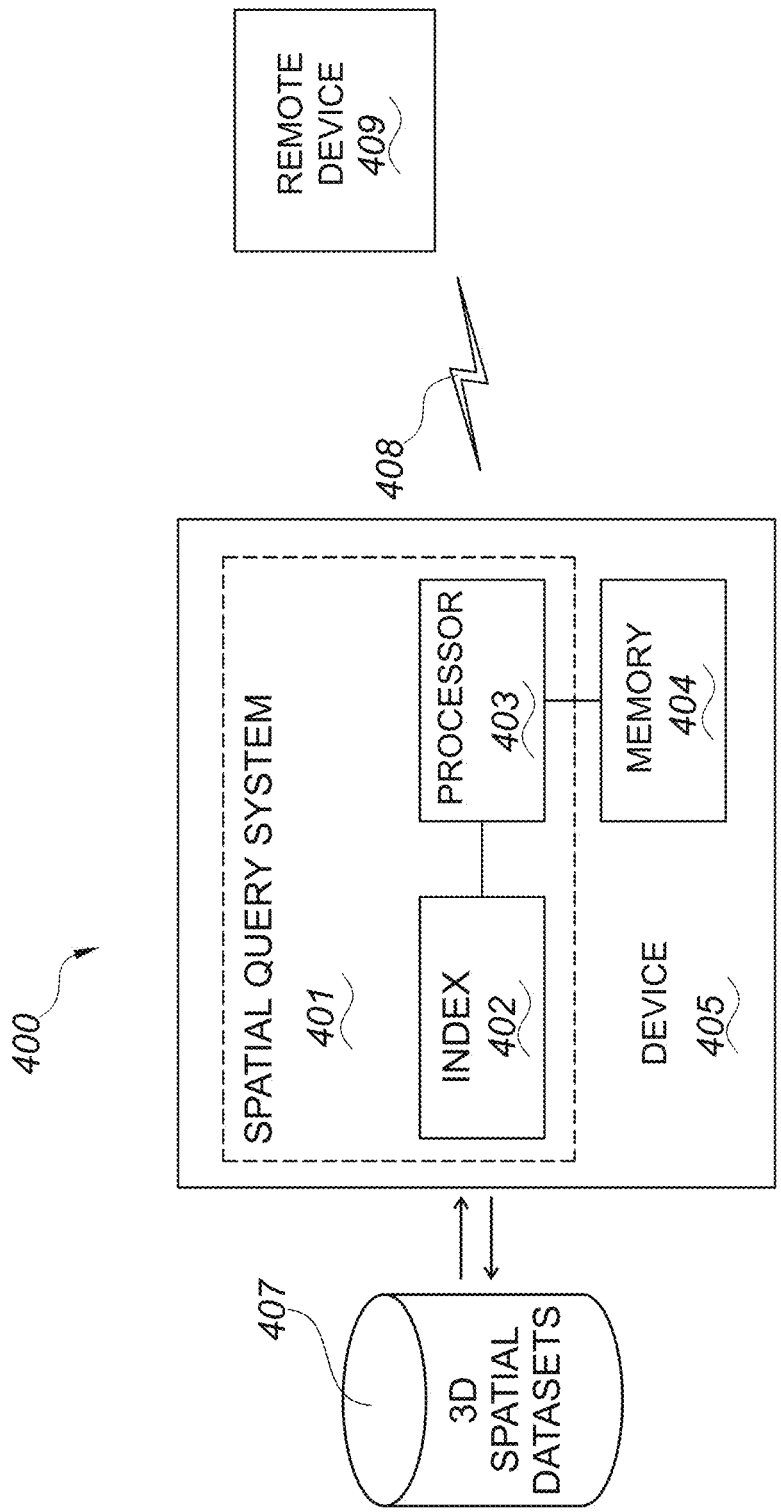
FIG. 26 illustrates a system block diagram including an example computer network infrastructure in accordance with an embodiment of the 3D spatial query system.

FIG. 26 is a simplified block diagram illustrating example components of an example computing system, according to an exemplary embodiment. One or both of the devices 405 and the remote device 409 of FIG. 26, may take the form of computing system 350 shown in FIG. 25. In particular, FIG. 26 illustrates a simplified block diagram illustrating an example computer network infrastructure, according to an exemplary embodiment. In system 400, a device 405 communicates using a communication link 408 (e.g., a wired or wireless connection) to a remote device 409. The device 405 may be any type of device that can receive data and display information corresponding to or associated with the data. For example, the device 405 may be a user computing device, a display or a 3D spatial query engine that communicates with the spatial query system 401.

Thus, the device 405 may include a 3D spatial query system 401 comprising a processor 403, a spatial index 402, and a display that interfaces with stored 3D spatial datasets 407. The display may be, for example, an optical see-through display, an optical see-around display, or a video see-through display. The processor 403 may receive data from the remote device 409, and configure the data for display on the display device. The processor 403 may be any type of processor, such as a micro-processor or a digital signal processor, for example.

The device 405 may further include on-board data storage, such as memory 404 coupled to the processor 403. The memory 404 may store software that can be accessed and executed by the processor 403, for example.

The remote device 409 may be any type of computing system or transmitter including a laptop computer, a mobile telephone, or tablet computing system, etc., that is configured to transmit data to the device 405. The remote device 409 and the device 405 may contain hardware to enable the communication link 408, such as processors, transmitters, receivers, antennas, etc.

In FIG. 26, the communication link 408 is illustrated as a wireless connection; however, wired connections may also be used. For example, the communication link 408 may be a wired serial bus such as a universal serial bus or a parallel bus, among other connections. The communication link 408 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), and/or Zigbee, among other possibilities. Either of such a wired and/or wireless connection may be a proprietary connection as well. The remote device 408 may be accessible via the Internet and may include a computing cluster associated with a particular web service (e.g., social-networking, photo sharing, address book, etc.).

Figure 24:
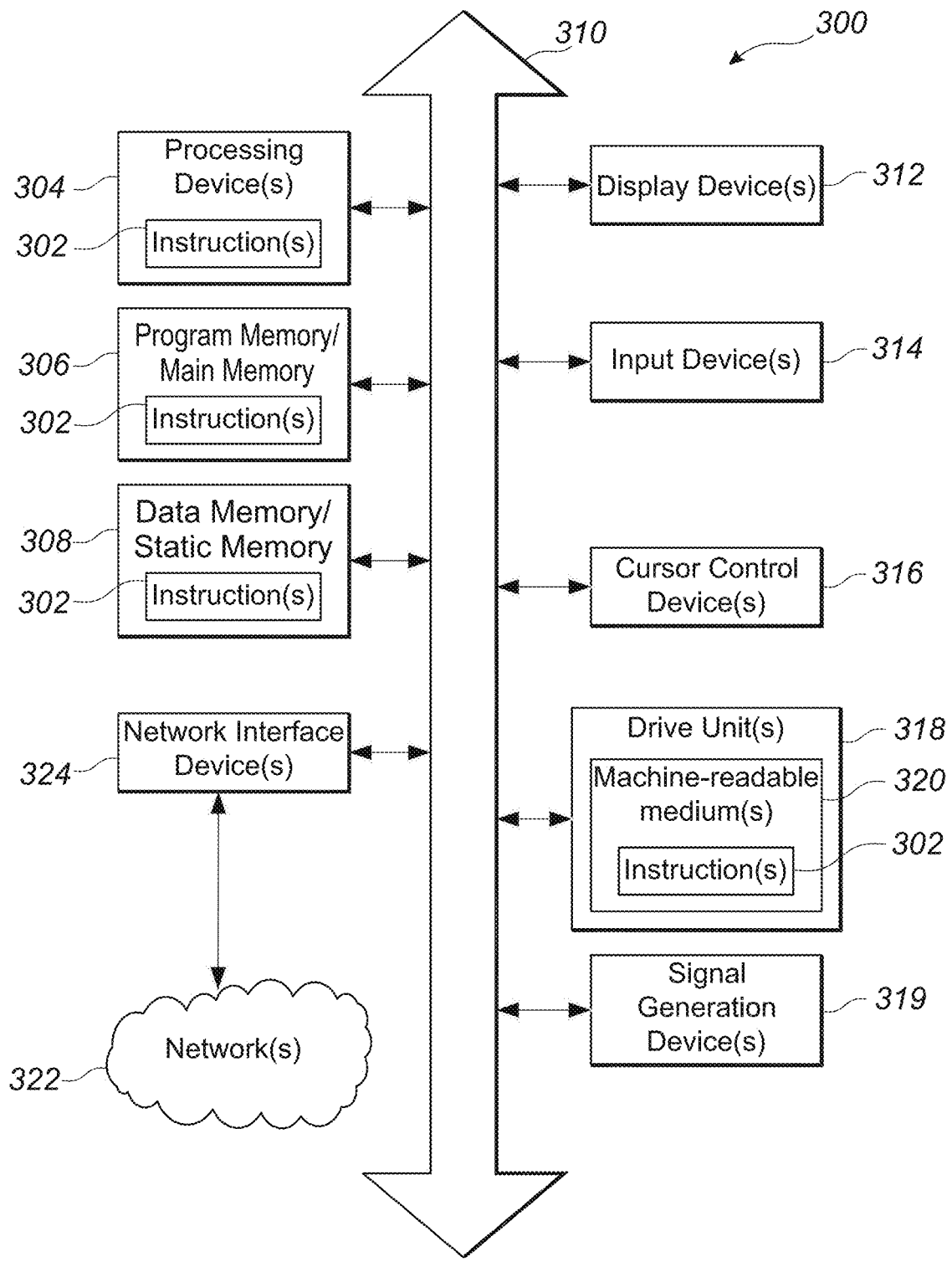
FIG. 24 is a block diagram showing a portion of an exemplary machine in the form of a computing system that performs methods according to one or more embodiments.

FIG. 24 is a block diagram of an illustrative embodiment of a general computing system 300. The computing system 300 can include a set of instructions that can be executed to cause the computing system 300 to perform any one or more of the methods or computer based functions disclosed herein. The computing system 300, or any portion thereof, may operate as a standalone device or may be connected, e.g., using a network 322 or other connection, to other computing systems or peripheral devices.

The computing system 300 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computing system 300 is illustrated, the term "system" shall also be taken to include any collection of systems or sub-systems that individually or jointly execute a set, or multiple sets, of instructions to perform one or more computer functions.

As illustrated in FIG. 24, the computing system 300 may include a processor 304, e.g., a central processing unit (CPU), a graphics-processing unit (GPU), or both. Moreover, the computing system 300 may include a main memory and/or program memory 306 and a static memory and/or data memory 308 that can communicate with each other via a bus 310. As shown, the computing system 300 may further include a video display unit 312, such as a liquid crystal display (LCD), an organic light emitting diode (OLED), a flat panel display, a solid state display, or a cathode ray tube (CRT). Additionally, the computing system 300 may include an input device 314, such as a keyboard, and a cursor control device 316, such as a mouse. The computing system 300 can also include a disk drive unit 318, a signal generation device 319, such as a speaker or remote control, and a network interface device 324.

In a particular embodiment or aspect, as depicted in FIG. 24, the disk drive unit 318 may include a machine-readable or computer-readable medium 320 in which one or more sets of instructions 302, e.g., software, can be embedded, encoded or stored. Further, the instructions 302 may embody one or more of the methods or logic as described herein. In a particular embodiment or aspect, the instructions 302 may reside completely, or at least partially, within the main memory 306, the static memory 308, and/or within the processor 304 during execution by the computing system 300. The main memory 306 and the processor 304 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computing systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computing system processing can be constructed to implement one or more of the methods or functionality as described herein.

It is also contemplated that a computer-readable medium includes instructions 302 or receives and executes instructions 302 responsive to a propagated signal, so that a device connected to a network 322 can communicate voice, video or data over the network 322. Further, the instructions 302 may be transmitted or received over the network 322 via the network interface device 324.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any tangible medium that is capable of storing or encoding a set of instructions for execution by a processor or that cause a computing system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture and store carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method to define and implement various spatial queries related to complex structures such as vessels and/or cells, that is memory based, on-demand and user-definable with respect to LODs, and operates on large-scale prodigious 3D data, has been described herein. Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" or "embodiment" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

Although the present specification describes components and functions implemented in the embodiments with reference to particular standards and protocols, the disclosed embodiment are not limited to such standards and protocols.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "embodiment" merely for convenience and without intending to voluntarily limit the scope of this application to any single embodiment or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 31 C.F.R. § 1.12(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Those skilled in the relevant art will appreciate that aspects of the invention can be practiced with other computer system configurations, including Internet appliances, hand-held devices, cellular or mobile phones, multi-processor systems, microprocessor-based or programmable consumer electronics, network PCs, client-server environments including thin clients, mini-computers, mainframe computers and the like. Aspects of the invention can be embodied in a special purpose computer or data processor that is specifically programmed, configured or constructed to perform one or more of the computer-executable instructions or modules explained in detail below. Indeed, the term "computer" as used herein refers to any data processing platform or device.

Aspects of the invention can also be practiced in distributed computing environments, where tasks or modules are performed by remote processing devices, which are linked through a communications network. In a distributed computing environment, program modules or sub-routines may be located in both local and remote memory storage devices, such as with respect to a wearable and/or mobile computer and/or a fixed-location computer. Aspects of the invention described below may be stored and distributed on computer-readable media, including magnetic and optically readable and removable computer disks, as well as distributed electronically over the Internet or over other networks (including wireless networks). Those skilled in the relevant art will recognize that portions of the invention may reside on a server computer or server platform, while corresponding portions reside on a client computer. For example, such a client server architecture may be employed within a single mobile computing device, among several computers of several users, and between a mobile computer and a fixed-location computer. Data structures and transmission of data particular to aspects of the invention are also encompassed within the scope of the invention.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "embodiment" merely for convenience and without intending to voluntarily limit the scope of this application to any single embodiment or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate example embodiment.

Although preferred embodiments have been described herein with reference to the accompanying drawings, it is to be understood that the disclosure is not limited to those precise embodiments and that various other changes and modifications may be affected herein by one skilled in the art without departing from the scope or spirit of the embodiments, and that it is intended to claim all such changes and modifications that fall within the scope of this disclosure.

What is claimed is:

1. A system associated with progressive spatial analysis of prodigious 3D data including complex structures, the system comprising:
   a 3D spatial query engine including a computing device that performs the following operations:
      receiving minimum boundary information related to a first data object;
      receiving minimum boundary information related to a second data object, the first data object and the second data object being proximate neighbors;
      determining whether boundary data associated with the first data object is within an area delineated by minimum boundary information of first data objects;
      generating a first geometric structure associated with the first data object based on respective decompressed data associated with the first data object;
      determining a structural skeleton using the first geometric structure associated with the first data object in order to identify its respective skeleton vertices;
      generating a geometric representation based on the skeleton vertices associated the first geometric structure;
      determining whether boundary data associated with the second data object is within the area delineated by minimum boundary information of the first data object;
      identifying whether a centroid point of the second data object intersects the geometric representation associated with the first object; and
      determining a location of the centroid point of the second data object with respect to the first data object in order to identify a minimum distance between the first data object and the second data object.

2. The system as recited in claim 1, which further comprises iteratively receiving and processing minimum boundary information related to multiple first data objects and multiple second data objects.

3. The system as recited in claim 1, wherein the first data object is a blood vessel and the second data object is one of a cell and a nucleus.

4. The system as recited in claim 1, wherein the first data object is a first biological structure and the second data object is a second biological structure.

5. The system as recited in claim 3, in which the progressive spatial analysis further comprises a determination of a nearest distance between at least one nucleus and a nearest blood vessel.

6. The system as recited in claim 1, in which generating a first geometric structure associated with the first data object based on its decompressed data further comprises compressing the first data object according to a specified level of detail (LOD).

7. The system as recited in claim 6, which further comprises the specified level of detail (LOD) being varied to refine determination of minimum distance, based on an evaluation of compression of the first data object as associated with the progressive spatial analysis thereof.

8. A system associated with progressive spatial analysis of prodigious 3D data including complex structures, the system comprising:
   a 3D spatial query engine including a computing device that performs the following operations:
      receiving minimum boundary information related to first data objects;
      receiving minimum boundary information related to second data objects;
      initializing an array with the minimum boundary information related to the first data objects;
      determining whether minimum boundary information associated with one of the first data objects is related to an area delineated by the minimum boundary information in the array;
      determining whether a first area delineated by the minimum boundary information associated with the one of the first data objects intersects an area delineated by a second area delineated by the minimum boundary information associated with one of the second data objects;
      generating a first geometric structure associated with the one of the first data objects based on respective decompressed data associated with the one of the first data objects;
      generating a second geometric structure object associated with the one of the second data objects based on respective decompressed data associated with the one of the second data objects;

determining whether a first geometric region defined by the first geometric structure intersects a second geometric region defined by the second geometric structure;

determining a spatial measurement of an intersecting region defined by an intersection of the first geometric region with the second geometric region; and identifying a first intersecting object and a second intersecting object associated with the intersecting region and respective volume information associated with the intersecting region.

9. The system as recited in claim 8, in which the progressive spatial analysis further comprises determining a minimum distance between the one of the first data objects and a nearest second data object based on a tree-based analysis of their respective minimum bounding information.

10. The system as recited in claim 8, in which the progressive spatial analysis further comprises determining nearest distances between the first objects and the second objects based on a spatial proximity estimation distance analysis associated with extracted bounding geometries of a surface mesh of first data objects with respect to nearest second data objects.

11. The system as recited in claim 8, in which the progressive spatial analysis further comprises:

defining a first polygon based on the minimum boundary information associated with a first object;

defining a second polygon based on minimum boundary information associated with one or more of nearest second objects of the first object;

generating a buffered boundary that surrounds the first polygon determined by the minimum boundary information associated with the first object;

determining an intersection between respective first polygon of the first data object and the second polygon associated with the one or more of nearest second objects;

duplicating the first object so that a first duplicate of the first data object resides within the first polygon; and the second duplicate resides outside a boundary of the second polygon associated with the one or more of the nearest neighbor objects; and determining a minimum distance between the first duplicate of the first data object and the one or more of the nearest neighbor second objects.

12. A method associated with progressive spatial analysis of prodigious 3D data including complex structures, the method comprising:

a 3D spatial query engine including a computing device that performs the following operations:

receiving minimum boundary information related to a first data object;

receiving minimum boundary information related to a second data object, the first data object and the second data object being proximate neighbors;

determining whether boundary data associated with the first data object is within an area delineated by minimum boundary information of first data objects;

generating a first geometric structure associated with the first data object based on respective decompressed data associated with the first data object;

determining a structural skeleton using the first geometric structure associated with the first data object in order to identify its respective skeleton vertices;

generating a geometric representation based on the skeleton vertices associated the first geometric structure;

determining whether boundary data associated with the second data object is within the area delineated by minimum boundary information of the first data object;

identifying whether a centroid point of the second data object intersects the geometric representation associated with the first object; and determining a location of the centroid point of the second data object with respect to the first data object, in order to identify a minimum distance between the first data object and the second data object.

13. The method as recited in claim 12, which further comprises iteratively receiving and processing minimum boundary information related to multiple first data objects and multiple second data objects.

14. The method as recited in claim 12, wherein the first data object is a blood vessel; and the second data object is one of a cell and nucleus.

15. The method as recited in claim 12, wherein the first data object is a first biological structure and the second data object is a second biological structure.

16. The method as recited in claim 14, in which the progressive spatial analysis further comprises a determination of a nearest distance between at least one nucleus and a nearest blood vessel.

17. The method as recited in claim 12, in which generating a first geometric structure associated with the first data object based on its decompressed data further comprises compressing the first data object according to a specified level of detail (LOD).

18. The method as recited in claim 17, which further comprises the specified level of detail (LOD) being varied to refine determination of minimum distance, based on an evaluation of compression of the first data object as associated with the progressive spatial analysis thereof.

19. A method associated with progressive spatial analysis of prodigious 3D data including complex structures, the method comprising:

a 3D spatial query engine including a computing device that performs the following operations:

receiving minimum boundary information related to first data objects;

receiving minimum boundary information related to second data objects;

initializing an array with the minimum boundary information related to the first data objects;

determining whether minimum boundary information associated with one of the first data objects is related to an area delineated by the minimum boundary information in the array;

determining whether a first area delineated by the minimum boundary information associated with the one of the first data objects intersects an area delineated by a second area delineated by the minimum boundary information associated with one of the second data objects;

generating a first geometric structure associated with the one of the first data objects based on respective decompressed data associated with the one of the first data objects;

generating a second geometric structure associated with the one of the second data objects based on respective decompressed data associated with the one of the second data objects;

determining whether a first geometric region defined by the first geometric structure intersects a second geometric region defined by the second geometric structure;

determining a spatial measurement of an intersecting region defined by an intersection of the first geometric region with the second geometric region; and identifying a first intersecting object and a second intersecting object associated with the intersecting region and respective volume information associated with the intersecting region.

20. The method as recited in claim 19, in which the progressive spatial analysis further comprises determining a minimum distance between the one of the first data objects and a nearest second data object based on a tree-based analysis of their respective minimum bounding information.

21. The method as recited in claim 19, in which the progressive spatial analysis further comprises determining nearest distances between the first objects and the second objects based on a spatial proximity estimation distance analysis associated with extracted bounding geometries of a surface mesh of first data objects with respect to nearest second data objects.

22. The method as recited in claim 19, in which the progressive spatial analysis further comprises:

defining a first polygon based on the minimum boundary information associated with a first object;

defining a second polygon based on minimum boundary information associated with one or more of nearest second objects of the first object;

generating a buffered boundary that surrounds the first polygon determined by the minimum boundary information associated with the first object;

determining an intersection between respective first polygon of the first data object and the second polygon associated with the one or more of nearest second objects;

duplicating the first object so that a first duplicate of the first data object resides within the first polygon; and the second duplicate resides outside a boundary of the second polygon associated with the one or more of the nearest neighbor objects; and determining a minimum distance between the first duplicate of the first data object and the one or more of the nearest neighbor second objects.

23. A non-transitory computer-readable device storing instructions that, when executed by a processing device, perform operations comprising:

receiving minimum boundary information related to a first data object;

receiving minimum boundary information related to a second data object, the first data object and the second data object being proximate neighbors;

determining whether boundary data associated with the first data object is within an area delineated by minimum boundary information of first data objects;

generating a first geometric structure associated with the first data object based on respective decompressed data associated with the first data object;

determining a structural skeleton using the first geometric structure associated with the first data object in order to identify its respective skeleton vertices;

generating a geometric representation based on the skeleton vertices associated with the first geometric structure;

determining whether boundary data associated with the second data object is within the area delineated by minimum boundary information of the first data object;

identifying whether a centroid point of the second data object intersects the geometric representation associated with the first object; and determining a location of the centroid point of the second data object with respect to the first data object in order to identify a minimum distance between the first data object and the second data object.

24. A non-transitory computer-readable device storing instructions that, when executed by a processing device, perform operations comprising:

receiving minimum boundary information related to first data objects;

receiving minimum boundary information related to second data objects;

initializing an array with the minimum boundary information related to the first data objects;

determining whether minimum boundary information associated with one of the first data objects is related to an area delineated by the minimum boundary information in the array;

determining whether a first area delineated by the minimum boundary information associated with the one of the first data objects intersects an area delineated by a second area delineated by the minimum boundary information associated with one of the second data objects;

generating a first geometric structure associated with the one of the first data objects based on respective decompressed data associated with the one of the first data objects;

generating a second geometric structure associated with the one of the second data objects based on respective decompressed data associated with the one of the second data objects;

determining whether a first geometric region defined by the first geometric structure intersects a second geometric region defined by the second geometric structure;

determining a spatial measurement of an intersecting region defined by an intersection of the first geometric region with the second geometric region; and identifying a first intersecting object and a second intersecting object associated with the intersecting region and respective volume information associated with the intersecting region.

25. The non-transitory computer-readable device as recited in claim 24, further comprising the following operations:

defining a first polygon based on the minimum boundary information associated with a first object;

defining a second polygon based on minimum boundary information associated with one or more of nearest second objects of the first object;

generating a buffered boundary that surrounds the first polygon determined by the minimum boundary information associated with the first object;

determining an intersection between respective first polygon of the first data object and the second polygon associated with the one or more of nearest second objects;

duplicating the first object so that a first duplicate of the first data object resides within the first polygon, and the second duplicate resides outside a boundary of the second polygon associated with the one or more of the nearest neighbor objects; and determining a minimum distance between the first duplicate of the first data object and the one or more of the nearest neighbor second objects.

26. The system as recited in claim 1, wherein the computing device in the 3D spatial query engine further performs:
   executing a progressive polyhedron mesh compression algorithm for compressing individual 3D objects; and
   indexing the individual 3D objects into memory after executing the compression algorithm;
   wherein compressing the individual 3D objects comprises generating successive levels of detail for a 3D mesh to meet different accuracy requirements.

27. The system as recited in claim 1, wherein the computing device in the 3D spatial query engine further performs:
   partitioning the 3D data into one or more partitioned cuboids; and
   on-demand object-level spatial indexing configured to index all objects in each of the partitioned cuboids for supporting index based spatial queries.

28. The system as recited in claim 27, wherein the computing device in the 3D spatial query engine further performs structural indexing for supporting individual complex objects.

29. The system as recited in claim 1, wherein the computing device in the 3D spatial query engine further performs:
   dynamically decompressing, at run-time, a subset of required 3D objects in the 3D data at a specified level of detail; and
   creating, at run-time, necessary spatial indexes in-memory to accelerate query processing.

30. The system as recited in claim 29, wherein creating the spatial indexes comprises performing at least topological skeleton based indexing and hierarchical axis-aligned bounding box tree based indexing to accelerate distance based spatial queries.

* * * * *

UNITED STATES PATENT AND TRADEMARK OFFICE
CERTIFICATE OF CORRECTION

| | |
|---|---|
| PATENT NO. | : 11,188,738 B2 |
| APPLICATION NO. | : 16/481744 |
| DATED | : November 30, 2021 |
| INVENTOR(S) | : Yanhui Liang, Fusheng Wang and Hoang Vo |

It is certified that error appears in the above-identified patent and that said Letters Patent is hereby corrected as shown below:

In the Specification

Column 19, Line 46: now reads "indicates as L" should read -- indicates as $L^i$ --

Column 42, Line 45: now reads "LOD i" should read -- LOD_i --

Signed and Sealed this
Eighth Day of November, 2022

Katherine Kelly Vidal
*Director of the United States Patent and Trademark Office*